(12) United States Patent
Hughes et al.

(10) Patent No.: US 6,506,560 B1
(45) Date of Patent: *Jan. 14, 2003

(54) CLONED DNA POLYMERASES FROM THERMOTOGA AND MUTANTS THEREOF

(75) Inventors: A. John Hughes, Germantown, MD (US); Deb K. Chatterjee, Gaithersburg, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/238,471

(22) Filed: Jan. 28, 1999

Related U.S. Application Data

(60) Division of application No. 08/706,706, filed on Sep. 6, 1996, now Pat. No. 6,015,668, which is a continuation-in-part of application No. 08/689,818, filed on Aug. 14, 1996, now abandoned, which is a continuation-in-part of application No. 08/537,400, filed on Oct. 2, 1995, now Pat. No. 5,939,301, which is a continuation-in-part of application No. 08/370,190, filed on Jan. 9, 1995, now Pat. No. 5,912,155, which is a continuation-in-part of application No. 08/316,423, filed on Sep. 30, 1994, now abandoned, said application No. 08/706,706, is a continuation-in-part of application No. 08/576,759, filed on Dec. 21, 1995, now abandoned, which is a continuation of application No. 08/537,397, filed on Oct. 2, 1995, now abandoned, which is a continuation-in-part of application No. 08/525,057, filed on Sep. 8, 1995, now abandoned.

(51) Int. Cl.$^7$ .............................. C12Q 1/68; C12N 9/12; C12P 19/34
(52) U.S. Cl. .............................. 435/6; 435/194; 435/15; 435/320.1; 435/252.3; 435/254.11; 435/325; 435/91.1; 435/91.2; 435/91.5; 435/91.51; 536/23.1; 536/23.2
(58) Field of Search .............................. 435/6, 15, 194, 435/320.1, 252.3, 254.11, 325, 91.1, 91.2, 91.5, 91.51; 53/23.1, 23.2

(56) References Cited

U.S. PATENT DOCUMENTS

| | | | |
|---|---|---|---|
| 5,420,029 A | | 5/1995 | Gelfand et al. .............. 435/194 |
| 5,912,155 A | * | 6/1999 | Chatterjee et al. ........... 435/194 |
| 5,939,301 A | * | 8/1999 | Hughes, Jr. et al. ......... 435/194 |
| 6,001,645 A | | 12/1999 | Slater et al. .............. 435/320.1 |
| 6,015,668 A | * | 1/2000 | Hughes et al. ................. 435/6 |

FOREIGN PATENT DOCUMENTS

| | | |
|---|---|---|
| WO | WO 96/10640 A1 | 4/1996 |

OTHER PUBLICATIONS

Barnes, W.M., "The fidelity of *Taq* polymerase catalyzing PCR is improved by an N–terminal deletion," *Gene* 112:29–35, Elsevier Science Publishers B.V. (1992).
Ishino, Y., et al., "Amino Acid Sequence Motifs Essential to 3'→ 5' Exonuclease Activity of *Escherichia coli* DNA Polymerase II," *J. Biol. Chem.* 269:14655–14660, The American Society of Biochemistry and Molecular Biology, Inc. (May 1994).
Reeve, M.A., and Fuller, C.W., "A novel thermostable polymerase for DNA sequencing," *Nature* 376:796–797, Macmillan Journals Ltd. (Aug. 1995).
Supplementary Partial European Search Report for Application No. 96933753.4, dated Jun. 18, 2002.

* cited by examiner

*Primary Examiner*—Rebecca E. Prouty
*Assistant Examiner*—Richard G. Hutson
(74) *Attorney, Agent, or Firm*—Sterne, Kessler, Goldstein & Fox P.L.L.C.

(57) ABSTRACT

The invention relates to a substantially pure thermostable DNA polymerase from Thermotoga (Tne and Tma) and mutants thereof. The Tne DNA polymerase has a molecular weight of about 100 kilodaltons and is more thermostable than Taq DNA polymerase. The mutant DNA polymerase has at least one mutation selected from the group consisting of (1) a first mutation that substantially reduces or eliminates 3'→5' exonuclease activity of said DNA polymerase; (2) a second mutation that substantially reduces or eliminates 5'→3' exonuclease activity of said DNA polymerase; (3) a third mutation in the O helix of said DNA polymerase resulting in said DNA polymerase becoming non-discriminating against dideoxynucleotides. The present invention also relates to the cloning and expression of the wild type or mutant DNA polymerases in *E. coli*, to DNA molecules containing the cloned gene, and to host cells which express said genes. The DNA polymerases of the invention may be used in well-known DNA sequencing and amplification reactions.

17 Claims, 30 Drawing Sheets

```
          BamHI
   1 GGATCCAGAC TGGTGGATCG TCAGTGCGGA TTATTCCCAA ATAGAACTCA GAATCCTCGC
       G  S  R   L  V  D    R  Q  C  G   L  F  P  N   R  T  Q  N   P  R
      → D  P  D   W  W  I    V  S  A  D   Y  S  Q  I   E  L  R  I   L
         I  Q     T  G  G    S  V  R      I  I  P  K  -  N  S  E   S  S

61 TCATCTCAGT GGTGATGAGA ACCTTGTGAA GGCCTTCGAG GAGGGCATCG ATGTGCACAC
       S  S  Q   W  -  -    E  P  C  E    G  L  R  G    G  H  R  C   A  H
      → A  H  L   S  G  D    E  N  L  V    K  A  F  E    E  G  I  D   V  H
         L  I  S   V  V  M    R  T  L  -    R  P  S  R    R  A  S  M   C  T

121 CTTGACTGCC TCCAGGATCT ACAACGTAAA GCCAGAAGAA GTGAACGAAG AAATGCGACG
       L  D  C   L  Q  D    L  Q  R  K    A  R  R  S    E  R  R  N   A  T
      → T  L  T   A  S  R    I  Y  N  V    K  P  E  E    V  N  E  M   R
         P  -  L   P  P  G    S  T  T  -    S  Q  K  K    -  T  K  K   C  D

181 GGTTGGAAAG ATGGTGAACT TCTCTATAAT ATACGGTGTC ACACCGTACG GTCTTTCTGT
       G  W  K   D  G  E    L  L  Y  N    I  R  C  H    T  V  R  S   F  C
      → R  V  G   K  M  V  N (F) S  I    I  Y  G  V    T  P  Y  G   L  S
         G  L  E   R  W  -    T  S  L  -    Y  T  V  S    H  R  T  V   F  L

241 GAGACTTGGA ATACCGGTTA AAGAAGCAGA AAAGATGATT ATCAGCTATT TCACACTGTA
       E  T  W   N  T  G    -  R  S  R    K  D  D  Y    Q  L  F  H   T  V
      → V  R  L   G  I  P    V  K  E  A    E  K  M  I    I  S  Y  F   T  L
         -  D  L   E  Y  R    L  K  K  Q    K  R  -  L    S  A  I  S   H  C

301 TCCAAAGGTG CGAAGCTACA TCCAGCAGGT TGTTGCAGAG GCAAAAGAGA AGGGCTACGT
       S  K  G   A  K  L    H  P  A  G    C  C  R  G    K  R  E  G   L  R
      → Y  P  K   V  R  S  Y  I  Q  Q    V  V  A  E    A  K  E  K   G  Y
         I  Q  R   C  E  A    T  S  S  R    L  L  Q  R    Q  K  R  R   A  T

361 CAGGACTCTC TTTGGAAGAA AAAGAGATAT TCCCCAGCTC ATGGCAAGGG ACAAGAACAC
       Q  D  S   L  W  K    K  K  R  Y    S  P  A  H    G  K  G  Q   E  H
      → V  R  T   L  F  G    R  K  R  I    P  Q  L  M    A  R  D  K   N
         S  G  L   S  L  E    E  K  E  I    F  P  S  W    Q  G  T  R   T

421 CCAGTCCGAA GGCGAAAGAA TCGCAATAAA CACCCCCATT CAGGGAACTG CGGCAGATAT
       P  V  R   R  R  K    N  R  N  K    H  P  H  S    G  N  C  G   R  Y
      → T  Q  S   E  G  E    R  I  A  I    N  T  P  I    Q  G  T  A   A  D
         P  S  P   K  A  K    E  S  Q  -    T  P  P  F    R  E  L  R   Q  I
```

FIG.5A

```
481  AATAAAATTG GCTATGATAG ATATAGACGA GGAGCTGAGA AAAAGAAACA TGAAATCCAG
       N  K  I    G  Y  D    R  Y  R  R    G  A  E    K  K  K    H  E  I  Q
   →  I  I  K  L    A  M  I    D  I  D    E  E  L  R    K  R  N    M  K  S
       -  -  N    W  L  -    -  I  -    T  R  S  -    E  K  E  T    -  N  P

541  AATGATCATT CAGGTTCATG ACGAACTGGT CTTCGAGGTT CCCGATGAGG AAAAAGAAGA
       N  D  H    S  G  S    -  R  T  G    L  R  G    S  R  -    G  K  R  R
   →  R  M  I  I    Q  V  H    D  E  L    V  F  E  V    P  D  E    E  K  E
       E  -  S    F  R  F  M    T  N  W    S  S  R    F  P  M  R    K  K  K

601  ACTAGTTGAT CTGGTGAAGA ACAAAATGAC AAATGTGGTG AAACTCTCTG TGCCTCTTGA
       T  S  -    S  G  E    E  Q  N  D    K  C  G    E  T  L    C  A  S  -
   →  E  L  V  D    L  V  K    N  K  M    T  N  V  V    K  L  S    V  P  L
       N  -  L    I  W  -    R  T  K  -    Q  M  W.    -  N  S  L    C  L  L

661  GGTTGACATA AGCATCGGAA AAAGCTGGTC TTGA
       G  -  H    K  H  R    K  K  L  V  L
   →  E  V  D  I    S  I  G    K  S  W  S    -
       R  L  T    -  A  S  E    K  A  G  L
```

FIG.5B

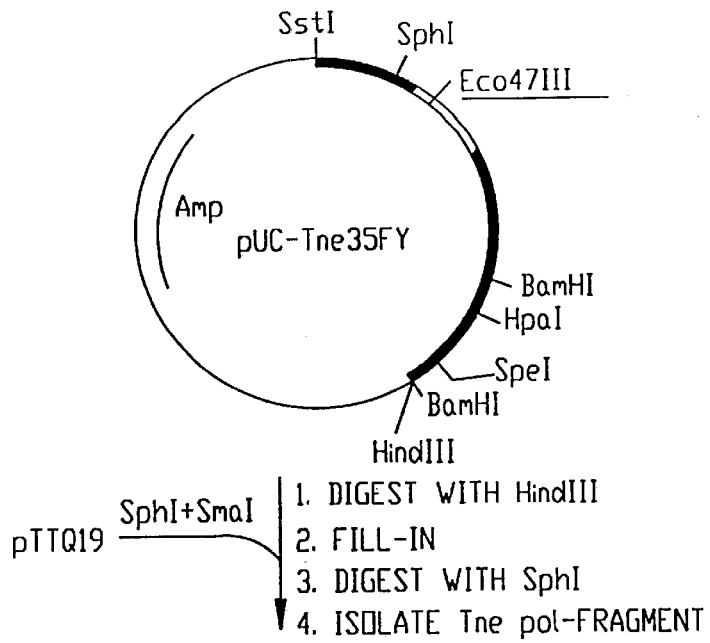
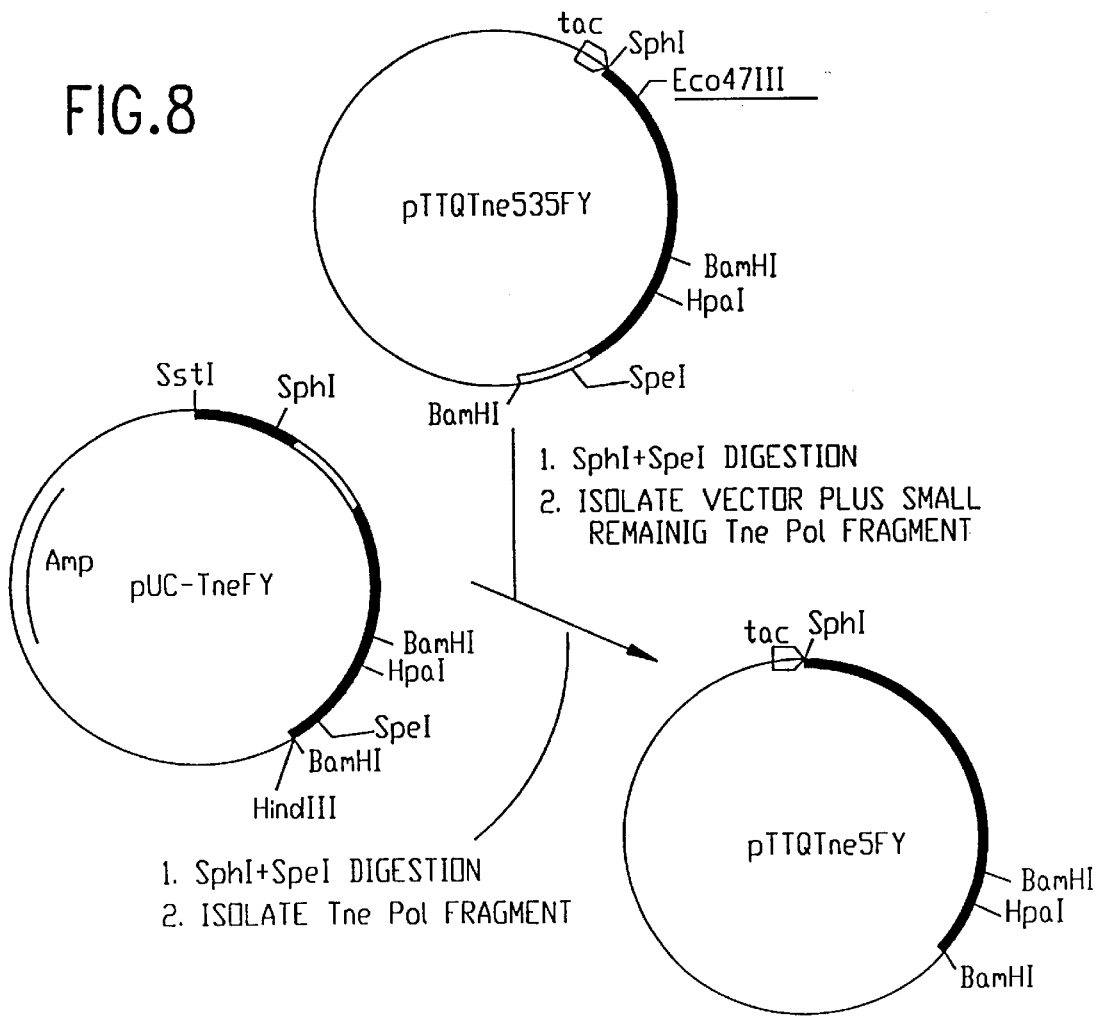
FIG.8

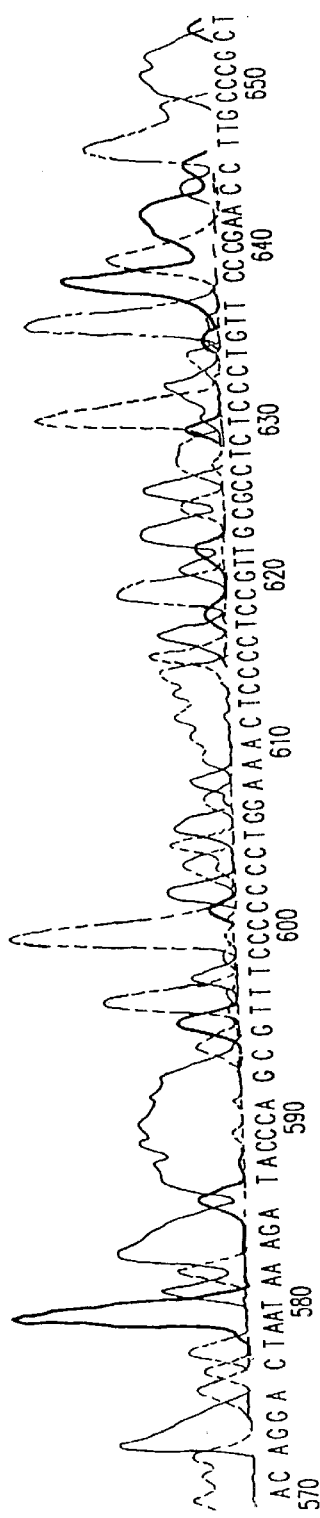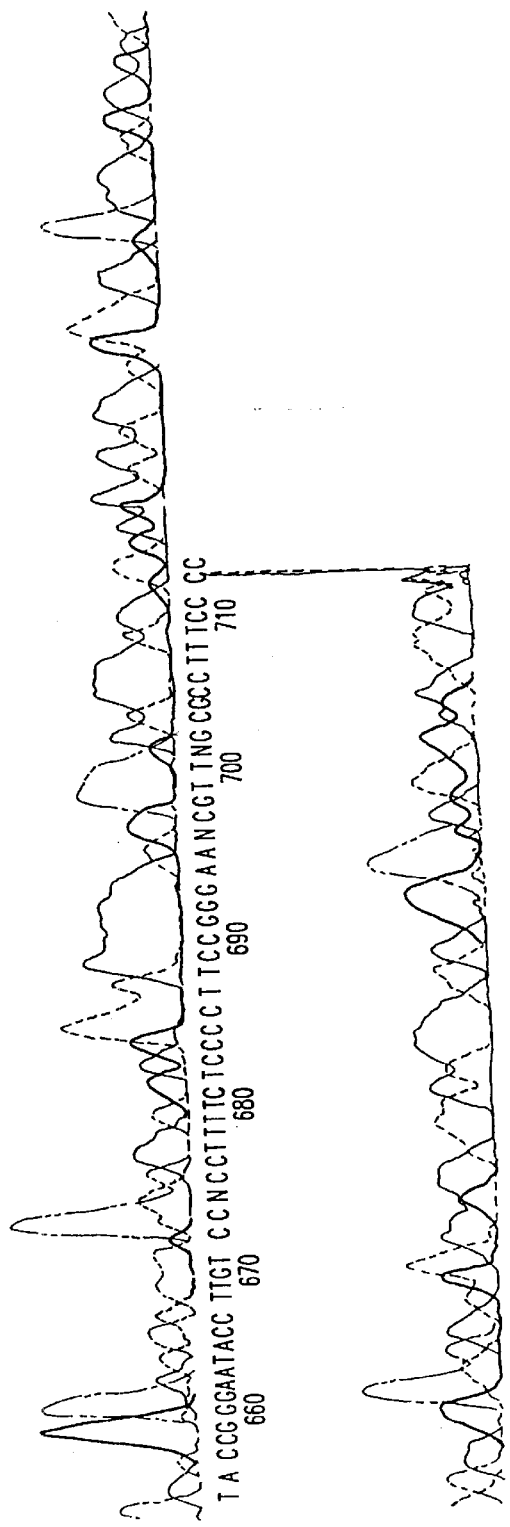
FIG. 17F

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 14 amino acids
      (B) TYPE: amino acid (C) STRANDEDNESS: Not Relevant
        (D) TOPOLOGY: Not Relevant (ii) MOLECULE TYPE: peptide (xi) SEQUENCE DESCRIPTION: SEQ ID NO: 1:

Arg Xaa Xaa Xaa Lys Xaa Xaa Xaa Phe Xaa Xaa Xaa Tyr Xaa
 1               5                   10

(2) INFORMATION FOR SEQ ID NO: 2:

(i) SEQUENCE CHARACTERISTICS:
        (A) LENGTH: 2682 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..2679

(xi) SEQUENCE DESCRIPTION: SEQ ID NO: 2:

```
ATG GCG AGA CTA TTT CTC TTT GAT GGC ACA GCC CTG GCC TAC AGG GCA        48
Met Ala Arg Leu Phe Leu Phe Asp Gly Thr Ala Leu Ala Tyr Arg Ala
 1               5                   10                  15

TAT TAC GCC CTC GAC AGA TCC CTT TCC ACA TCC ACA GGA ATT CCA ACG        96
Tyr Tyr Ala Leu Asp Arg Ser Leu Ser Thr Ser Thr Gly Ile Pro Thr
                20                  25                  30

AAC GCC GTC TAT GGC GTT GCC AGG ATG CTC GTT AAA TTC ATT AAG GAA       144
Asn Ala Val Tyr Gly Val Ala Arg Met Leu Val Lys Phe Ile Lys Glu
             35                  40                  45

CAC ATT ATA CCC GAA AAG GAC TAC GCG GCT GTG GCC TTC GAC AAG AAG       192
His Ile Ile Pro Glu Lys Asp Tyr Ala Ala Val Ala Phe Asp Lys Lys
         50                  55                  60

GCA GCG ACG TTC AGA CAC AAA CTG CTC GTA AGC GAC AAG GCG CAA AGG       240
Ala Ala Thr Phe Arg His Lys Leu Leu Val Ser Asp Lys Ala Gln Arg
 65                  70                  75                  80

CCA AAG ACT CCG GCT CTT CTA GTT CAG CAG CTA CCT TAC ATC AAG CGG       288
Pro Lys Thr Pro Ala Leu Leu Val Gln Gln Leu Pro Tyr Ile Lys Arg
                 85                  90                  95

CTG ATA GAA GCT CTT GGT TTC AAA GTG CTG GAG CTG GAG GGA TAC GAA       336
Leu Ile Glu Ala Leu Gly Phe Lys Val Leu Glu Leu Glu Gly Tyr Glu
                100                 105                 110

GCA GAC GAT ATC ATC GCC ACG CTT GCA GTC AGG GCT GCA CGT TTT TTG       384
Ala Asp Asp Ile Ile Ala Thr Leu Ala Val Arg Ala Ala Arg Phe Leu
            115                 120                 125

ATG AGA TTT TCA TTA ATA ACC GGT GAC AAG GAT ATG CTT CAA CTT GTA       432
Met Arg Phe Ser Leu Ile Thr Gly Asp Lys Asp Met Leu Gln Leu Val
130                 135                 140

AAC GAG AAG ATA AAG GTC TGG AGA ATC GTC AAG GGG ATA TCG GAT CTT       480
Asn Glu Lys Ile Lys Val Trp Arg Ile Val Lys Gly Ile Ser Asp Leu
145                 150                 155                 160

GAG CTT TAC GAT TCG AAA AAG GTG AAA GAA AGA TAC GGT GTG GAA CCA       528
Glu Leu Tyr Asp Ser Lys Lys Val Lys Glu Arg Tyr Gly Val Glu Pro
                165                 170                 175

CAT CAG ATA CCG GAT CTT CTA GCA CTG ACG GGA GAC GAC ATA GAC AAC       576
His Gln Ile Pro Asp Leu Leu Ala Leu Thr Gly Asp Asp Ile Asp Asn
            180                 185                 190

ATT CCC GGT GTA ACG GGA ATA GGT GAA AAG ACC GCT GTA CAG CTT CTC       624
Ile Pro Gly Val Thr Gly Ile Gly Glu Lys Thr Ala Val Gln Leu Leu
        195                 200                 205
```

```
GGC AAG TAT AGA AAT CTT GAA TAC ATT CTG GAG CAT GCC CGT GAA CTC      672
Gly Lys Tyr Arg Asn Leu Glu Tyr Ile Leu Glu His Ala Arg Glu Leu
    210                 215                 220

CCC CAG AGA GTG AGA AAG GCT CTC TTG AGA GAC AGG GAA GTT GCC ATC      720
Pro Gln Arg Val Arg Lys Ala Leu Leu Arg Asp Arg Glu Val Ala Ile
225                 230                 235                 240

CTC AGT AAA AAA CTT GCA ACT CTG GTG ACG AAC GCA CCT GTT GAA GTG      768
Leu Ser Lys Lys Leu Ala Thr Leu Val Thr Asn Ala Pro Val Glu Val
                245                 250                 255

GAC TGG GAA GAG ATG AAA TAC AGA GGA TAC GAC AAG AGA AAA CTA CTT      816
Asp Trp Glu Glu Met Lys Tyr Arg Gly Tyr Asp Lys Arg Lys Leu Leu
            260                 265                 270

CCG ATA TTG AAA GAA CTG GAG TTT GCT TCC ATC ATG AAG GAA CTT CAA      864
Pro Ile Leu Lys Glu Leu Glu Phe Ala Ser Ile Met Lys Glu Leu Gln
        275                 280                 285

CTG TAC GAA GAA GCA GAA CCC ACC GGA TAC GAA ATC GTG AAG GAT CAT      912
Leu Tyr Glu Glu Ala Glu Pro Thr Gly Tyr Glu Ile Val Lys Asp His
    290                 295                 300

AAG ACC TTC GAA GAT CTC ATC GAA AAG CTG AAG GAG GTT CCA TCT TTT      960
Lys Thr Phe Glu Asp Leu Ile Glu Lys Leu Lys Glu Val Pro Ser Phe
305                 310                 315                 320

GCC CTG GAC CTT GAA ACG TCC TCC TTG GAC CCG TTC AAC TGT GAG ATA     1008
Ala Leu Asp Leu Glu Thr Ser Ser Leu Asp Pro Phe Asn Cys Glu Ile
                325                 330                 335

GTC GGC ATC TCC GTG TCG TTC AAA CCG AAA ACA GCT TAT TAC ATT CCA     1056
Val Gly Ile Ser Val Ser Phe Lys Pro Lys Thr Ala Tyr Tyr Ile Pro
            340                 345                 350

CTT CAT CAC AGA AAC GCC CAC AAT CTT GAT GAA ACA CTG GTG CTG TCG     1104
Leu His His Arg Asn Ala His Asn Leu Asp Glu Thr Leu Val Leu Ser
        355                 360                 365

AAG TTG AAA GAG ATC CTC GAA GAC CCG TCT TCG AAG ATT GTG GGT CAG     1152
Lys Leu Lys Glu Ile Leu Glu Asp Pro Ser Ser Lys Ile Val Gly Gln
    370                 375                 380

AAC CTG AAG TAC GAC TAC AAG GTT CTT ATG GTA AAG GGT ATA TCG CCA     1200
Asn Leu Lys Tyr Asp Tyr Lys Val Leu Met Val Lys Gly Ile Ser Pro
385                 390                 395                 400

GTT TAT CCG CAT TTT GAC ACG ATG ATA GCT GCA TAT TTG CTG GAG CCA     1248
Val Tyr Pro His Phe Asp Thr Met Ile Ala Ala Tyr Leu Leu Glu Pro
                405                 410                 415

AAC GAG AAA AAA TTC AAT CTC GAA GAT CTG TCT TTG AAA TTT CTC GGA     1296
Asn Glu Lys Lys Phe Asn Leu Glu Asp Leu Ser Leu Lys Phe Leu Gly
            420                 425                 430

TAC AAA ATG ACG TCT TAT CAG GAA CTG ATG TCG TTT TCC TCA CCA CTT     1344
Tyr Lys Met Thr Ser Tyr Gln Glu Leu Met Ser Phe Ser Ser Pro Leu
        435                 440                 445

TTT GGT TTC AGC TTT GCG GAT GTT CCG GTA GAC AAG GCT GCC GAA TAC     1392
Phe Gly Phe Ser Phe Ala Asp Val Pro Val Asp Lys Ala Ala Glu Tyr
    450                 455                 460

TCC TGC GAG GAT GCA GAC ATC ACT TAT AGG CTC TAC AAG ATA CTC AGC     1440
Ser Cys Glu Asp Ala Asp Ile Thr Tyr Arg Leu Tyr Lys Ile Leu Ser
465                 470                 475                 480

ATG AAG CTC CAT GAA GCG GAA CTT GAG AAC GTC TTC TAC AGG ATA GAG     1488
Met Lys Leu His Glu Ala Glu Leu Glu Asn Val Phe Tyr Arg Ile Glu
                485                 490                 495

ATG CCG TTG GTG AAC GTC TTG GCA CGA ATG GAA TTC AAC TGG GTG TAT     1536
Met Pro Leu Val Asn Val Leu Ala Arg Met Glu Phe Asn Trp Val Tyr
            500                 505                 510

GTT GAC ACA GAA TTC CTG AAA AAG CTC TCG GAG GAG TAC GGC AAA AAG     1584
Val Asp Thr Glu Phe Leu Lys Lys Leu Ser Glu Glu Tyr Gly Lys Lys
        515                 520                 525
```

```
CTC GAG GAA CTG GCC GAA AAA ATC TAC CAG ATA GCA GGT GAG CCC TTC         1632
Leu Glu Glu Leu Ala Glu Lys Ile Tyr Gln Ile Ala Gly Glu Pro Phe
        530                 535                 540

AAC ATC AAT TCT CCA AAA CAG GTT TCA AAC ATC CTT TTT GAG AAG CTG         1680
Asn Ile Asn Ser Pro Lys Gln Val Ser Asn Ile Leu Phe Glu Lys Leu
545                 550                 555                 560

GGA ATA AAA CCC CGT GGA AAA ACG ACA AAA ACA GGA GAT TAC TCT ACC         1728
Gly Ile Lys Pro Arg Gly Lys Thr Thr Lys Thr Gly Asp Tyr Ser Thr
                    565                 570                 575

AGG ATA GAG GTG TTG GAA GAG ATA GCG AAT GAG CAC GAG ATA GTA CCC         1776
Arg Ile Glu Val Leu Glu Glu Ile Ala Asn Glu His Glu Ile Val Pro
            580                 585                 590

CTC ATT CTC GAG TTC AGA AAG ATC CTG AAA CTG AAA TCG ACC TAC ATA         1824
Leu Ile Leu Glu Phe Arg Lys Ile Leu Lys Leu Lys Ser Thr Tyr Ile
        595                 600                 605

GAC ACC CTT CCG AAA CTT GTG AAC CCG AAA ACC GGA AGA TTT CAT GCA         1872
Asp Thr Leu Pro Lys Leu Val Asn Pro Lys Thr Gly Arg Phe His Ala
610                 615                 620

TCT TTC CAC CAG ACG GGT ACC GCC ACT GGC AGG TTG AGT AGC AGT GAT         1920
Ser Phe His Gln Thr Gly Thr Ala Thr Gly Arg Leu Ser Ser Ser Asp
625                 630                 635                 640

CCA AAT CTT CAG AAT CTT CCG ACA AAG AGC GAA GAG GGA AAA GAA ATT         1968
Pro Asn Leu Gln Asn Leu Pro Thr Lys Ser Glu Glu Gly Lys Glu Ile
                    645                 650                 655

AGA AAA GCG ATT GTG CCC CAG GAT CCA GAC TGG TGG ATC GTC AGT GCG         2016
Arg Lys Ala Ile Val Pro Gln Asp Pro Asp Trp Trp Ile Val Ser Ala
            660                 665                 670

GAT TAT TCC CAA ATA GAA CTC AGA ATC CTC GCT CAT CTC AGT GGT GAT         2064
Asp Tyr Ser Gln Ile Glu Leu Arg Ile Leu Ala His Leu Ser Gly Asp
        675                 680                 685

GAG AAC CTT GTG AAG GCC TTC GAG GAG GGC ATC GAT GTG CAC ACC TTG         2112
Glu Asn Leu Val Lys Ala Phe Glu Glu Gly Ile Asp Val His Thr Leu
690                 695                 700

ACT GCC TCC AGG ATC TAC AAC GTA AAG CCA GAA GAA GTG AAC GAA GAA         2160
Thr Ala Ser Arg Ile Tyr Asn Val Lys Pro Glu Glu Val Asn Glu Glu
705                 710                 715                 720

ATG CGA CGG GTT GGA AAG ATG GTG AAC TTC TCT ATA ATA TAC GGT GTC         2208
Met Arg Arg Val Gly Lys Met Val Asn Phe Ser Ile Ile Tyr Gly Val
                    725                 730                 735

ACA CCG TAC GGT CTT TCT GTG AGA CTT GGA ATA CCG GTT AAA GAA GCA         2256
Thr Pro Tyr Gly Leu Ser Val Arg Leu Gly Ile Pro Val Lys Glu Ala
            740                 745                 750

GAA AAG ATG ATT ATC AGC TAT TTC ACA CTG TAT CCA AAG GTG CGA AGC         2304
Glu Lys Met Ile Ile Ser Tyr Phe Thr Leu Tyr Pro Lys Val Arg Ser
        755                 760                 765

TAC ATC CAG CAG GTT GTT GCA GAG GCA AAA GAG AAG GGC TAC GTC AGG         2352
Tyr Ile Gln Gln Val Val Ala Glu Ala Lys Glu Lys Gly Tyr Val Arg
770                 775                 780

ACT CTC TTT GGA AGA AAA AGA GAT ATT CCC CAG CTC ATG GCA AGG GAC         2400
Thr Leu Phe Gly Arg Lys Arg Asp Ile Pro Gln Leu Met Ala Arg Asp
785                 790                 795                 800

AAG AAC ACC CAG TCC GAA GGC GAA AGA ATC GCG ATA AAC ACC CCC ATT         2448
Lys Asn Thr Gln Ser Glu Gly Glu Arg Ile Ala Ile Asn Thr Pro Ile
                    805                 810                 815

CAG GGA ACT GCG GCA GAT ATA ATA AAA TTG GCT ATG ATA GAT ATA GAC         2496
Gln Gly Thr Ala Ala Asp Ile Ile Lys Leu Ala Met Ile Asp Ile Asp
            820                 825                 830
```

```
GAG GAG CTG AGA AAA AGA AAC ATG AAA TCC AGA ATG ATC ATT CAG GTT          2544
Glu Glu Leu Arg Lys Arg Asn Met Lys Ser Arg Met Ile Ile Gln Val
            835                 840                 845

CAT GAC GAA CTG GTC TTC GAG GTT CCC GAT GAG GAA AAA GAA GAA CTA          2592
His Asp Glu Leu Val Phe Glu Val Pro Asp Glu Glu Lys Glu Glu Leu
        850                 855                 860

GTT GAT CTG GTG AAG AAC AAA ATG ACA AAT GTG GTG AAA CTC TCT GTG          2640
Val Asp Leu Val Lys Asn Lys Met Thr Asn Val Val Lys Leu Ser Val
865                 870                 875                 880

CCT CTT GAG GTT GAC ATA AGC ATC GGA AAA AGC TGG TCT TGA                  2682
Pro Leu Glu Val Asp Ile Ser Ile Gly Lys Ser Trp Ser
                885                 890
```

(2) INFORMATION FOR SEQ ID NO: 3:

(i) SEQUENCE CHARACTERISTICS:
       (A) LENGTH: 893 amino acids
       (B) TYPE: amino acid
       (D) TOPOLOGY: linear (ii) MOLECULE TYPE: protein (xi) SEQUENCE DESCRIPTION: SEQ ID NO: 3:

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Val Tyr Gly Val Ala Arg Met Leu Val Lys Phe Ile Lys Glu
        35                  40                  45

His Ile Ile Pro Glu Lys Asp Tyr Ala Ala Val Ala Phe Asp Lys Lys
    50                  55                  60

Ala Ala Thr Phe Arg His Lys Leu Leu Val Ser Asp Lys Ala Gln Arg
65                  70                  75                  80

Pro Lys Thr Pro Ala Leu Leu Val Gln Gln Leu Pro Tyr Ile Lys Arg
                85                  90                  95

Leu Ile Glu Ala Leu Gly Phe Lys Val Leu Glu Leu Glu Gly Tyr Glu
            100                 105                 110

Ala Asp Asp Ile Ile Ala Thr Leu Ala Val Arg Ala Ala Arg Phe Leu
        115                 120                 125

Met Arg Phe Ser Leu Ile Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
                165                 170                 175

His Gln Ile Pro Asp Leu Leu Ala Leu Thr Gly Asp Asp Ile Asp Asn
            180                 185                 190

Ile Pro Gly Val Thr Gly Ile Gly Glu Lys Thr Ala Val Gln Leu Leu
        195                 200                 205

Gly Lys Tyr Arg Asn Leu Glu Tyr Ile Leu Glu His Ala Arg Glu Leu
    210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
                245                 250                 255

Asp Trp Glu Glu Met Lys Tyr Arg Gly Tyr Asp Lys Arg Lys Leu Leu
            260                 265                 270
```

-continued

```
Pro Ile Leu Lys Glu Leu Glu Phe Ala Ser Ile Met Lys Glu Leu Gln
        275                 280                 285
Leu Tyr Glu Glu Ala Glu Pro Thr Gly Tyr Glu Ile Val Lys Asp His
        290                 295                 300
Lys Thr Phe Glu Asp Leu Ile Glu Lys Leu Lys Glu Val Pro Ser Phe
305                 310                 315                 320
Ala Leu Asp Leu Glu Thr Ser Ser Leu Asp Pro Phe Asn Cys Glu Ile
                325                 330                 335
Val Gly Ile Ser Val Ser Phe Lys Pro Lys Thr Ala Tyr Tyr Ile Pro
                340                 345                 350
Leu His His Arg Asn Ala His Asn Leu Asp Glu Thr Leu Val Leu Ser
        355                 360                 365
Lys Leu Lys Glu Ile Leu Glu Asp Pro Ser Ser Lys Ile Val Gly Gln
        370                 375                 380
Asn Leu Lys Tyr Asp Tyr Lys Val Leu Met Val Lys Gly Ile Ser Pro
385                 390                 395                 400
Val Tyr Pro His Phe Asp Thr Met Ile Ala Ala Tyr Leu Leu Glu Pro
                405                 410                 415
Asn Glu Lys Lys Phe Asn Leu Glu Asp Leu Ser Leu Lys Phe Leu Gly
        420                 425                 430
Tyr Lys Met Thr Ser Tyr Gln Glu Leu Met Ser Phe Ser Ser Pro Leu
        435                 440                 445
Phe Gly Phe Ser Phe Ala Asp Val Pro Val Asp Lys Ala Ala Glu Tyr
        450                 455                 460
Ser Cys Glu Asp Ala Asp Ile Thr Tyr Arg Leu Tyr Lys Ile Leu Ser
465                 470                 475                 480
Met Lys Leu His Glu Ala Glu Leu Glu Asn Val Phe Tyr Arg Ile Glu
                485                 490                 495
Met Pro Leu Val Asn Val Leu Ala Arg Met Glu Phe Asn Trp Val Tyr
                500                 505                 510
Val Asp Thr Glu Phe Leu Lys Lys Leu Ser Glu Glu Tyr Gly Lys Lys
        515                 520                 525
Leu Glu Glu Leu Ala Glu Lys Ile Tyr Gln Ile Ala Gly Glu Pro Phe
        530                 535                 540
Asn Ile Asn Ser Pro Lys Gln Val Ser Asn Ile Leu Phe Glu Lys Leu
545                 550                 555                 560
Gly Ile Lys Pro Arg Gly Lys Thr Thr Lys Thr Gly Asp Tyr Ser Thr
                565                 570                 575
Arg Ile Glu Val Leu Glu Glu Ile Ala Asn Glu His Glu Ile Val Pro
                580                 585                 590
Leu Ile Leu Glu Phe Arg Lys Ile Leu Lys Leu Lys Ser Thr Tyr Ile
        595                 600                 605
Asp Thr Leu Pro Lys Leu Val Asn Pro Lys Thr Gly Arg Phe His Ala
        610                 615                 620
Ser Phe His Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
                645                 650                 655
Arg Lys Ala Ile Val Pro Gln Asp Pro Asp Trp Trp Ile Val Ser Ala
                660                 665                 670
Asp Tyr Ser Gln Ile Glu Leu Arg Ile Leu Ala His Leu Ser Gly Asp
        675                 680                 685
```

```
Glu Asn Leu Val Lys Ala Phe Glu Gly Ile Asp Val His Thr Leu
    690             695                 700

Thr Ala Ser Arg Ile Tyr Asn Val Lys Pro Glu Glu Val Asn Glu Glu
705             710              715                  720

Met Arg Arg Val Gly Lys Met Val Asn Phe Ser Ile Ile Tyr Gly Val
                725             730                 735

Thr Pro Tyr Gly Leu Ser Val Arg Leu Gly Ile Pro Val Lys Glu Ala
            740              745             750

Glu Lys Met Ile Ile Ser Tyr Phe Thr Leu Tyr Pro Lys Val Arg Ser
        755              760             765

Tyr Ile Gln Gln Val Val Ala Glu Ala Lys Lys Gly Tyr Val Arg
    770             775              780

Thr Leu Phe Gly Arg Lys Arg Asp Ile Pro Gln Leu Met Ala Arg Asp
785             790              795                  800

Lys Asn Thr Gln Ser Glu Gly Glu Arg Ile Ala Ile Asn Thr Pro Ile
                805             810                 815

Gln Gly Thr Ala Ala Asp Ile Ile Lys Leu Ala Met Ile Asp Ile Asp
            820              825             830

Glu Glu Leu Arg Lys Arg Asn Met Lys Ser Arg Met Ile Ile Gln Val
        835             840              845

His Asp Glu Leu Val Phe Glu Val Pro Asp Glu Glu Lys Glu Glu Leu
    850              855             860

Val Asp Leu Val Lys Asn Lys Met Thr Asn Val Val Lys Leu Ser Val
865             870              875                  880

Pro Leu Glu Val Asp Ile Ser Ile Gly Lys Ser Trp Ser
                885             890

(2) INFORMATION FOR SEQ ID NO: 4:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 4:

Pro Ser Phe Ala Leu Asp Leu Glu Thr Ser Ser
1               5                   10

(2) INFORMATION FOR SEQ ID NO: 5:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 5:

Pro Val Phe Ala Phe Asp Thr Glu Thr Asp Ser
1               5                   10

(2) INFORMATION FOR SEQ ID NO: 6:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant
```

(ii) MOLECULE TYPE: peptide (xi) SEQUENCE DESCRIPTION: SEQ ID NO: 6:

Gly Pro Val Ala Phe Asp Ser Glu Thr Ser Ala
1               5                   10

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 7:

Met Ile Val Ser Asp Ile Glu Ala Asn Ala
1               5                   10

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GACGTTTCAA GCGCTAGGGC AAAAGA                                          26

(2) INFORMATION FOR SEQ ID NO: 9:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 9:

Arg Arg Val Gly Lys Met Val Asn Phe Ser Ile Ile Tyr Gly
1               5                   10

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 10:

Arg Arg Ser Ala Lys Ala Ile Asn Phe Gly Leu Ile Tyr Gly
1               5                   10

(2) INFORMATION FOR SEQ ID NO: 11:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 11:

Arg Gln Ala Ala Lys Ala Ile Thr Phe Gly Ile Leu Tyr Gly
1               5                   10

(2) INFORMATION FOR SEQ ID NO: 12:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO: 12:

Arg Asp Asn Ala Lys Thr Phe Ile Tyr Gly Phe Leu Tyr Gly
1               5                   10

(2) INFORMATION FOR SEQ ID NO: 13:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO: 13:

Arg Arg Ala Ala Lys Thr Ile Asn Phe Gly Val Leu Tyr Gly
1               5                   10

(2) INFORMATION FOR SEQ ID NO: 14:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 14:

GTATATTATA GAGTAGTTAA CCATCTTTCC A                                              31

(2) INFORMATION FOR SEQ ID NO: 15:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 15:

GTAGGCCAGG GCTGTGCCGG CAAAGAGAAA TAGTC                                          35

(2) INFORMATION FOR SEQ ID NO: 16:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 16:

GAAGCATATC CTTGGCGCCG GTTATTATGA AAATC                                    35

(2) INFORMATION FOR SEQ ID NO: 17:

(i) SEQUENCE CHARACTERISTICS:
      (A) LENGTH: 694 base pairs
      (B) TYPE: nucleic acid
      (C) STRANDEDNESS: double
      (D) TOPOLOGY: both (ii) MOLECULE TYPE: cDNA (ix) FEATURE:
      (A) NAME/KEY: CDS
      (B) LOCATION: 2..691

(xi) SEQUENCE DESCRIPTION: SEQ ID NO: 17:

```
G GAT CCA GAC TGG TGG ATC GTC AGT GCG GAT TAT TCC CAA ATA GAA            46
  Asp Pro Asp Trp Trp Ile Val Ser Ala Asp Tyr Ser Gln Ile Glu
      895             900             905

CTC AGA ATC CTC GCT CAT CTC AGT GGT GAT GAG AAC CTT GTG AAG GCC          94
Leu Arg Ile Leu Ala His Leu Ser Gly Asp Glu Asn Leu Val Lys Ala
    910             915             920

TTC GAG GAG GGC ATC GAT GTG CAC ACC TTG ACT GCC TCC AGG ATC TAC         142
Phe Glu Glu Gly Ile Asp Val His Thr Leu Thr Ala Ser Arg Ile Tyr
925             930             935             940

AAC GTA AAG CCA GAA GAA GTG AAC GAA GAA ATG CGA CGG GTT GGA AAG         190
Asn Val Lys Pro Glu Glu Val Asn Glu Glu Met Arg Arg Val Gly Lys
                945             950             955

ATG GTG AAC TTC TCT ATA ATA TAC GGT GTC ACA CCG TAC GGT CTT TCT         238
Met Val Asn Phe Ser Ile Ile Tyr Gly Val Thr Pro Tyr Gly Leu Ser
                960             965             970

GTG AGA CTT GGA ATA CCG GTT AAA GAA GCA GAA AAG ATG ATT ATC AGC         286
Val Arg Leu Gly Ile Pro Val Lys Glu Ala Glu Lys Met Ile Ile Ser
    975             980             985

TAT TTC ACA CTG TAT CCA AAG GTG CGA AGC TAC ATC CAG CAG GTT GTT         334
Tyr Phe Thr Leu Tyr Pro Lys Val Arg Ser Tyr Ile Gln Gln Val Val
    990             995             1000

GCA GAG GCA AAA GAG AAG GGC TAC GTC AGG ACT CTC TTT GGA AGA AAA         382
Ala Glu Ala Lys Glu Lys Gly Tyr Val Arg Thr Leu Phe Gly Arg Lys
1005            1010            1015            1020

AGA GAT ATT CCC CAG CTC ATG GCA AGG GAC AAG AAC ACC CAG TCC GAA         430
Arg Asp Ile Pro Gln Leu Met Ala Arg Asp Lys Asn Thr Gln Ser Glu
                1025            1030            1035

GGC GAA AGA ATC GCG ATA AAC ACC CCC ATT CAG GGA ACT GCG GCA GAT         478
Gly Glu Arg Ile Ala Ile Asn Thr Pro Ile Gln Gly Thr Ala Ala Asp
                1040            1045            1050

ATA ATA AAA TTG GCT ATG ATA GAT ATA GAC GAG GAG CTG AGA AAA AGA         526
Ile Ile Lys Leu Ala Met Ile Asp Ile Asp Glu Glu Leu Arg Lys Arg
            1055            1060            1065

AAC ATG AAA TCC AGA ATG ATC ATT CAG GTT CAT GAC GAA CTG GTC TTC         574
Asn Met Lys Ser Arg Met Ile Ile Gln Val His Asp Glu Leu Val Phe
            1070            1075            1080

GAG GTT CCC GAT GAG GAA AAA GAA GAA CTA GTT GAT CTG GTG AAG AAC         622
Glu Val Pro Asp Glu Glu Lys Glu Glu Leu Val Asp Leu Val Lys Asn
1085            1090            1095            1100

AAA ATG ACA AAT GTG GTG AAA CTC TCT GTG CCT CTT GAG GTT GAC ATA         670
Lys Met Thr Asn Val Val Lys Leu Ser Val Pro Leu Glu Val Asp Ile
            1105            1110            1115
```

```
AGC ATC GGA AAA AGC TGG TCT TGA                                              694
Ser Ile Gly Lys Ser Trp Ser
         1120
```

(2) INFORMATION FOR SEQ ID NO: 18:

(i) SEQUENCE CHARACTERISTICS:
        (A) LENGTH: 230 amino acids
        (B) TYPE: amino acid
        (D) TOPOLOGY: linear (ii) MOLECULE TYPE: protein (xi) SEQUENCE DESCRIPTION: SEQ ID NO: 18:

```
Asp Pro Asp Trp Trp Ile Val Ser Ala Asp Tyr Ser Gln Ile Glu Leu
 1               5                  10                  15

Arg Ile Leu Ala His Leu Ser Gly Asp Glu Asn Leu Val Lys Ala Phe
             20                  25                  30

Glu Glu Gly Ile Asp Val His Thr Leu Thr Ala Ser Arg Ile Tyr Asn
         35                  40                  45

Val Lys Pro Glu Glu Val Asn Glu Glu Met Arg Arg Val Gly Lys Met
 50                  55                  60

Val Asn Phe Ser Ile Ile Tyr Gly Val Thr Pro Tyr Gly Leu Ser Val
 65                  70                  75                  80

Arg Leu Gly Ile Pro Val Lys Glu Ala Glu Lys Met Ile Ile Ser Tyr
             85                  90                  95

Phe Thr Leu Tyr Pro Lys Val Arg Ser Tyr Ile Gln Gln Val Val Ala
             100                 105                 110

Glu Ala Lys Glu Lys Gly Tyr Val Arg Thr Leu Phe Gly Arg Lys Arg
         115                 120                 125

Asp Ile Pro Gln Leu Met Ala Arg Asp Lys Asn Thr Gln Ser Glu Gly
 130                 135                 140

Glu Arg Ile Ala Ile Asn Thr Pro Ile Gln Gly Thr Ala Ala Asp Ile
145                 150                 155                 160

Ile Lys Leu Ala Met Ile Asp Ile Asp Glu Glu Leu Arg Lys Arg Asn
             165                 170                 175

Met Lys Ser Arg Met Ile Ile Gln Val His Asp Glu Leu Val Phe Glu
             180                 185                 190

Val Pro Asp Glu Glu Lys Glu Glu Leu Val Asp Leu Val Lys Asn Lys
         195                 200                 205

Met Thr Asn Val Val Lys Leu Ser Val Pro Leu Glu Val Asp Ile Ser
         210                 215                 220

Ile Gly Lys Ser Trp Ser
225                 230
```

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 19:

```
Phe Leu Phe Asp Gly Thr
 1               5
```

(2) INFORMATION FOR SEQ ID NO: 20:

(i) SEQUENCE CHARACTERISTICS:
    (A) LENGTH: 6 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO: 20:

Leu Leu Val Asp Gly His
1               5

(2) INFORMATION FOR SEQ ID NO: 21:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 21:

Ser Leu Ile Thr Gly Asp Lys Asp Met Leu
1               5                   10

(2) INFORMATION FOR SEQ ID NO: 22:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 22:

Arg Ile Leu Thr Ala Asp Lys Asp Leu Tyr
1               5                   10

(2) INFORMATION FOR SEQ ID NO: 23:

(i) SEQUENCE CHARACTERISTICS:
        (A) LENGTH: 687 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO: 23:

| | | | | | |
|---|---|---|---|---|---|
| TCGTACCNGG | GNTCNCNANA | TCGACTGCAG | CATGCAAGCT | GGCTAATCAT | GGTCATAGCT | 60 |
| GTTTCCTGTG | TGAAATTGTT | ATCCGCTCAC | AATTCCACAC | AACATACGAG | CCGGAAGCAT | 120 |
| AAAGTGTAAA | GCCTGGGGTG | CCTAATGAGT | GAGCTAACTC | ACATTAATTG | CGTTGCGCTC | 180 |
| ACTGCCCGCT | TTCCAGTCGG | GAAACCTGTC | GTGCCAGCTG | CATTAATGAA | TCGGCCAACG | 240 |
| CGCGGGGAGA | GGCGGTTTGC | GTATTGGGCG | CTCTTCCGCT | TCCTCGCTCA | CTGACTCGCT | 300 |
| GCGCTCGGTC | GTTCGGCTGC | GGCGAGCGGT | ATCAGCTCAC | TCAAAGGCGG | TAATACGGTT | 360 |
| ATCCACAGAA | TCAGGGGATA | ACGCAGGAAA | GAACATGTGA | GCAAAAGGCC | AGCAAAAGGC | 420 |
| CAGGAACCGT | AAAAAGGCC | GCGTTGCTGG | CGTTTTTCC | ATAGGCTCCG | CCCCCCTTGA | 480 |
| CGAGCATCAC | AAAAATTCGA | CGCTTCAAGT | TCAGAGGTGG | CGAAACCCG | ACAGGGACTA | 540 |
| TAAAGATTAC | CAGGGCGTTT | CCCCCCTGGG | AAGCTNCCTT | CGTGCGCTCT | CCTGTTCCCG | 600 |

```
AACCTGGCCG GTTTAACCGG GATACCNGNT CGGCCTTTTN TCCCCTTNGG GGGAANCCTT    660

GGGGNTTTTN GNAAAANGCT AAGGGTT                                       687
```

(2) INFORMATION FOR SEQ ID NO: 24:

(i) SEQUENCE CHARACTERISTICS:
        (A) LENGTH: 701 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO: 24:

```
GCTCGTACCG GGGATCTNNN ANATCGACTG CAGCATGCAA GCTTGGCGTA ATCATGGTCA     60

TAGCTGTTTC CTGTGTGAAA TTGTTATCCG CTCACAATTC CACACAACAT ACGAGCCGGA    120

AGCATAAAGT GTAAAGCCTG GGGTGCCTAA TGAGTGAGCT AACTCACATT AATTGCGTTG    180

CGCTCACTGC CCGCTTTCCA GTCGGGAAAC CTGTCGTGCC AGCTGCATTA ATGAATCGGC    240

CAACGCGCGG GGAGAGGCGG TTTGCGTATT GGGCGCTCTT CCGCTTCCTC GCTCACTGAC    300

TCGCTGCGCT CGGTCGTTCG GCTGCGGCGA GCGGTATCAG CTCACTCAAA GGCGGTAATA    360

CGGTTATCCA CAGAATCAGG GGATAACGCA GGAAAGAACA TGTGAGCAAA AGGCCAGCAA    420

AAGGCCAGGA ACCGTAAAAA GGCCGCGTTG CTGGGCGTTT TTTCCATAGG CTCCGCCCCC    480

CTGANGAGCA TCANAAAAAT CGANGCTCAN GTCANAGGTG GCGAAACCCG ACAGGNCTAT    540

TAAAAGATNC CAGGCGTTT TCCCCCCTGG GAAGCTCCCT CGTGGGCTC TCCTGGTTNC      600

GGNNCCCTGN CCGGNTTACC GGGGATAANC TTGTTCCGGN CTTTNTCCCC TTCNGGGAAA    660

ANGGTGGGGG GTTTTNTNNA AAAGGCTCAA AGGCTGGTAN G                        701
```

(2) INFORMATION FOR SEQ ID NO: 25:

(i) SEQUENCE CHARACTERISTICS:
        (A) LENGTH: 717 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO: 25:

```
GNTNTAGNNN GGNCTAANNG GCGGGGAAAT CGAGCTCGGT ACCCGGGGAT CCTCTAGAGT     60

CGACCTGCAG GCATGCAAGC TTGGCGTAAT CATGGTCATA GCTGTTTCCT GTGTGAAATT    120

GTTATCCGCT CACAATTCCA CACAACATAC GAGCCGGAAG CATAAAGTGT AAAGCCTGGG    180

GTGCCTAATG AGTGAGCTAA CTCACATTAA TTGCGTTGCG CTCACTGCCC GCTTTCCAGT    240

CGGGAAACCT GTCGTGCCAG CTGCATTAAT GAATCGGCCA ACGCGCGGGG AGAGGCGGTT    300

TGCGTATTGG GCGCTCTTCC GCTTCCTCGC TCACTGACTC GCTGCGCTCG GTCGTTCGGC    360

TGCGGCGAGC GGTATCAGCT CACTCAAAGG CGGTAATACG GTTATCCACA GAATCAGGG    420

GATAACGCAG GAAAGAACA TGTGAGCAAA AGGCCCAGCA AAAGGCCAGG AACCCGTAAA     480

AAGGCCGCGT TGCCTGGCGT TTTTCCATAG GCTCCGCCCC CCTTGACGAG CAATCACAAA    540

AATCGACGCT CAAAGTCAAG AGGTGGCGAA ACCCCGACAG GACTTATAA AGATACCCAG     600

GCCGTTTCCC CCTGGAAGCT CCCTCCGTG CGCTTCTCCT TGGTTCCCGA CCCTGCCGCT     660

TTACCNGGAT NCCTGTCCGC CCTTTTNTCC CTTTCNGGNA ACCGGGCGCT TTTTTTT       717
```

-continued (2) INFORMATION FOR SEQ ID NO: 26:

(i) SEQUENCE CHARACTERISTICS:
        (A) LENGTH: 713 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO: 26:

```
NNNNCNNNNG GCTGANAGCG ATAAATCGAG CTCGGTACCC GGGGATCCTC TAGAGTCGAC      60

CTGCAGGCAT GCAAGCTTGG CGTAATCATG GTCATAGCTG TTTCCTGTGT GAAATTGTTA     120

TCCGCTCACA ATTCCACACA ACATACGAGC CGGAAGCATA AAGTGTAAAG CCTGGGGTGC     180

CTAATGAGTG AGCTAACTCA CATTAATTGC GTTGCGCTCA CTGCCCGCTT TCCAGTCGGG     240

AAACCTGTCG TGCCAGCTGC ATTAATGAAT CGGCCAACGC GCGGGGAGAG GCGGTTTGCG     300

TATTGGGCGC TCTTCCGCTT CCTCGCTCAC TGACTCGCTG CGCTCGGTCG TTCGGCTGCG     360

GCGAGCGGTA TCAGCTCACT CAAAGGCGGT AATACGGTTA TCCACAGAAT CAGGGGATAA     420

CGCAGGAAAG AACATGTTGA GCAAAAGGCC AGCAAAAGGC CAGGAACCGT AAAAAGGCCG     480

CGTTTGCTGG CGTTTTTCCC ATAGGCTCCG CCCCCCTTGA CGAACCATCA CAAAAATCGA     540

CGCTCAATTC AGAAGTTGGC GAAAACCCGA CAGGACTAAT AAAGATACCC AGCGTTTCCC     600

CCCCTGGAAA CTCCCCTCCG TTGCGCCTCT CCCTGTTCCC GAACCTTGCC CGCTTACCGG     660

GAATACCTTG TCCNCCTTTT CTCCCCTTCC GGGAANCGTT NGCGCCTTTC CCC            713
```

CLONED DNA POLYMERASES FROM THERMOTOGA AND MUTANTS THEREOF

CROSS-REFERENCE TO RELATED APPLICATIONS

This application is a divisional of application Ser. No. 08/706,706, filed Sep. 6, 1996, now U.S. Pat. No. 6,015,668, which is a continuation-in-part of application Ser. No. 08/689,818, filed Aug. 14, 1996, now abandoned, which is a continuation-in-part of application Ser. No. 08/537,400, filed Oct. 2, 1995, now U.S. Pat. No. 5,939,301, which is a continuation-in-part of application Ser. No. 08/370,190, filed Jan. 9, 1995, now U.S. Pat. No. 5,912,155, which is a continuation-in-part of application Ser. No. 08/316,423, filed Sep. 30, 1994, now abandoned. Application Ser. No.08/706,706 is also a continuation-in-part of application Ser. No. 08/576,759, filed Dec. 21, 1995, now abandoned, which is a continuation of application Ser. No. 08/537,397, filed Oct. 2, 1995, now abandoned, which is a continuation-in-part of application Ser. No. 08/525,057, filed Sep. 8, 1995, now abandoned. The contents of each of these applications are incorporated herein by reference.

BACKGROUND OF THE INVENTION

1. Field of the Invention

The present invention relates to a substantially pure thermostable DNA polymerase. Specifically, the DNA polymerase of the present invention is a Thermotoga DNA polymerase and more specifically a *Thermotoga neapolitana* (Tne) DNA polymerase or *Thermotoga maritima* (Tma) DNA polymerase. Preferably, the polymerase has a molecular weight of about 100 kilodaltons. The present invention also relates to the cloning and expression of the Thermotoga DNA polymerase in *E. coli*, to DNA molecules containing the cloned gene, and to hosts which express said genes. The DNA polymerase of the present invention may be used in DNA sequencing, amplification reactions, and cDNA synthesis.

This invention also relates to mutants of the Thermotoga DNA polymerase, including Tne and Tma DNA polymerase. Specifically, the DNA polymerases of the present invention have mutations which substantially reduce 3'→5' exonuclease activity; mutations resulting in the ability of the mutant DNA polymerase to incorporate dideoxynucleotides into a DNA molecule about as efficiently as deoxynucleotides; and mutations which substantially reduce 5'→3' exonuclease activity. The Thermotoga (e.g., Tne and Tma) mutant DNA polymerase of this invention can have one or more of these properties. These DNA polymerase mutants may also be used in DNA sequencing, amplification reactions, and cDNA synthesis.

The present invention is also directed to novel mutants of other DNA polymerases which have substantially reduced 5'→3' exonuclease activity.

BACKGROUND INFORMATION

DNA polymerases synthesize the formation of DNA molecules which are complementary to a DNA template. Upon hybridization of a primer to the single-stranded DNA template, polymerases synthesize DNA in the 5' to 3' direction, successively adding nucleotides to the 3'-hydroxyl group of the growing strand. Thus, in the presence of deoxyribonucleoside triphosphates (dNTPs) and a primer, a new DNA molecule, complementary to the single stranded DNA template, can be synthesized.

A number of DNA polymerases have been isolated from mesophilic microorganisms such as *E. coli*. A number of these mesophilic DNA polymerases have also been cloned. Lin et al. cloned and expressed T4 DNA polymerase in *E. coli* (*Proc. Natl. Acad. Sci. USA* 84:7000–7004 (1987)). Tabor et al. (U.S. Pat. No. 4,795,699) describes a cloned T7 DNA polymerase, while Minkley et al. (*J. Biol. Chem.* 259:10386–10392 (1984)) and Chatterjee (U.S. Pat. No. 5,047,342) described *E. coli* DNA polymerase I and the cloning of T5 DNA polymerase, respectively.

Although DNA polymerases from thermophiles are known, relatively little investigation has been done to isolate and even clone these enzymes. Chien et al., *J. Bacteriol.* 127:1550–1557 (1976) describe a purification scheme for obtaining a polymerase from *Thermus aquaticus* (Taq). The resulting protein had a molecular weight of about 63,000 daltons by gel filtration analysis and 68,000 daltons by sucrose gradient centrifugation. Kaledin et al., *Biokhymiya* 45:644–51 (1980) disclosed a purification procedure for isolating DNA polymerase from *T. aquaticus* YT1 strain. The purified enzyme was reported to be a 62,000 dalton monomeric protein. Gelfand et al. (U.S. Pat. No. 4,889,818) cloned a gene encoding a thermostable DNA polymerase from *Thermus aquaticus*. The molecular weight of this protein was found to be about 86,000 to 90,000 daltons.

Simpson et al. purified and partially characterized a thermostable DNA polymerase from a Thermotoga species (*Biochem. Cell. Biol.* 86:1292–1296 (1990)). The purified DNA polymerase isolated by Simpson et al. exhibited a molecular weight of 85,000 daltons as determined by SDS-polyacrylamide gel electrophoresis and size-exclusion chromatography. The enzyme exhibited half-lives of 3 minutes at 95° C. and 60 minutes at 50° C. in the absence of substrate and its pH optimum was in the range of pH 7.5 to 8.0. Triton X-100 appeared to enhance the thermostability of this enzyme. The strain used to obtain the thermostable DNA polymerase described by Simpson et al. was Thermotoga species strain FjSS3-B.1 (Hussar et al., *FEMS Microbiology Letters* 37:121–127 (1986)). Others have cloned and sequenced a thermostable DNA polymerase from *Thermotoga maritima* (U.S. Pat. No. 5,374,553, which is expressly incorporated herein by reference).

Other DNA polymerases have been isolated from thermophilic bacteria including *Bacillus steraothermophilus* (Stenesh et al., *Biochim. Biophys. Acta* 272:156–166 (1972); and Kaboev et al., *J. Bacteriol.* 145:21–26 (1981)) and several archaebacterial species (Rossi et al., *System. Appl. Microbiol.* 7:337–341 (1986); Klimczak et al., Biochemistry 25:4850–4855 (1986); and Elie et al., *Eur. J. Biochem.* 178:619–626 (1989)). The most extensively purified archaebacterial DNA polymerase had a reported half-life of 15 minutes at 87° C. (Elie et al. (1989), supra). Innis et al., In *PCR Protocol: A Guide To Methods and Amplification*, Academic Press, Inc., San Diego (1990) noted that there are several extreme thermophilic eubacteria and archaebacteria that are capable of growth at very high temperatures (Bergquist et al., *Biotech. Genet. Eng. Rev.* 5:199–244 (1987); and Kelly et al., *Biotechnol. Prog.* 4:47–62 (1988)) and suggested that these organisms may contain very thermostable DNA polymerases.

In many of the known polymerases, the 5'→3' exonuclease activity is present in the N-terminal region of the polymerase. (Ollis, et al., *Nature* 313:762–766 (1985); Freemont et al., *Proteins* 1:66–73 (1986); Joyce, *Cur. Opin. Struct. Biol.* 1:123–129 (1991).) There are some amino acids, the mutation of which are thought to impair the 5'→3' exonuclease activity of *E. coli* DNA polymerase I. (Gutman & Minton, *Nucl. Acids Res.* 21:4406–4407 (1993).) These amino acids include Tyr[77], Gly[103], Gly[184], and Gly[192] in *E. coli* DNA polymerase I. It is known that the 5'-exonuclease domain is dispensable. The best known example is the Klenow fragment of *E. coli* polymerase I. The Klenow fragment is a natural proteolytic fragment devoid of 5'-exonuclease activity (Joyce et. al., *J. Biol. Chem.* 257:1958–64 (1990).) Polymerases lacking this activity are useful for DNA sequencing.

Most DNA polymerases also contain a 3'→5' exonuclease activity. This exonuclease activity provides a proofreading ability to the DNA polymerase. A T5 DNA polymerase that lacks 3'→5' exonuclease activity is disclosed in U.S. Pat. No. 5,270,179. Polymerases lacking this activity are particularly useful for DNA sequencing.

The polymerase active site, including the dNTP binding domain is usually present at the carboxyl terminal region of the polymerase (Ollis et al., *Nature* 313:762–766 (1985); Freemont et al., *Proteins* 1:66–73 (1986)). It has been shown that Phe[762] of *E. coli* polymerase I is one of the amino acids that directly interacts with the nucleotides (Joyce & Steitz, *Ann. Rev. Biochem.* 63:777–822 (1994); Astatke, *J. Biol. Chem.* 270:1945–54 (1995)). Converting this amino acid to a Tyr results in a mutant DNA polymerase that does not discriminate against dideoxynucleotides. See copending U.S. application Ser. No. 08/525,087, of Deb K. Chatterjee, filed Sep. 8, 1995, entitled "Mutant DNA Polymerases and the Use Thereof," which is expressly incorporated herein by reference.

Thus, there exists a need in the art to develop more thermostable DNA polymerases. There also exists a need in the art to obtain wild type or mutant DNA polymerases that are devoid of exonuclease activities and are non-discriminating against dideoxynucleotides.

SUMMARY OF THE INVENTION

The present invention satisfies these needs in the art by providing additional DNA polymerases useful in molecular biology. Specifically, this invention includes a thermostable DNA polymerase. Preferably, the polymerase has a molecular weight of about 100 kilodaltons. Specifically, the DNA polymerase of the invention is isolated from Thermotoga, and more specifically, the DNA polymerase is obtained from *Thermotoga neapolitana* (Tne) and *Thermotoga maritima* (Tma). The Thermotoga species preferred for isolating the DNA polymerase of the present invention was isolated from an African continental solfataric spring (Windberger et al., *Arch. Microbiol.* 151. 506–512, (1989)).

The Thermotoga DNA polymerases of the present invention are extremely thermostable, showing more than 50% of activity after being heated for 60 minutes at 90° C. with or without detergent. Thus, the DNA polymerases of the present invention is more thermostable than Taq DNA polymerase.

The present invention is also directed to cloning a gene encoding a Thermotoga DNA polymerase enzyme. DNA molecules containing the Thermotoga DNA polymerase genes, according to the present invention, can be transformed and expressed in a host cell to produce the DNA polymerase. Any number of hosts may be used to express the Thermotoga DNA polymerase gene of the present invention; including prokaryotic and eukaryotic cells. Preferably, prokaryotic cells are used to express the DNA polymerase of the invention. The preferred prokaryotic host according to the present invention is *E. coli*.

The present invention also relates mutant thermostable DNA polymerases of the PolI type and DNA coding therefor, wherein there is amino acid change in the O-helix which renders the polymerase nondiscriminatory against ddNTPs in sequencing reactions. The O-helix is defined as RXXXKXXXFXXXYX, wherein X is any amino acid.

The present invention also relates to Thermotoga DNA polymerase mutants that lack exonuclease activity and/or which are nondiscriminatory against ddNTPs in sequencing reactions.

The present invention is also directed generally to DNA polymerases that have mutations that result in substantially reduced or missing 5'→3' exonuclease activity.

In particular, the invention relates to a Thermotoga DNA polymerase mutant which is modified at least one way selected from the group consisting of (a) to reduce or eliminate the 3'-5' exonuclease activity of the polymerase;

(b) to reduce or eliminate the 5'-3' exonuclease activity of the polymerase; and (c) to reduce or eliminate discriminatory behavior against a dideoxynucleotide.

The invention also relates to a method of producing a DNA polymerase, said method comprising:

(a) culturing the host cell of the invention;

(b) expressing said gene; and (c) isolating said DNA polymerase from said host cell.

The invention also relates to a method of synthesizing a double-stranded DNA molecule comprising:

(a) hybridizing a primer to a first DNA molecule; and (b) incubating said DNA molecule of step (a) in the presence of one or more deoxy- or dideoxyribonucleoside triphosphates and the DNA polymerase of the invention, under conditions sufficient to synthesize a second DNA molecule complementary to all or a portion of said first DNA molecule. Such deoxy- and dideoxyribonucleoside triphosphates include dATP, dCTP, dGTP, dTTP, dITP, 7-deaza-dGTP, 7-deaza-dATP, dUTP, ddATP, ddCTP, ddGTP, ddITP, ddTTP, [α-S]dATP, [α-S]dTTP, [α-S]dGTP, and [α-S]dCTP.

The invention also relates to a method of sequencing a DNA molecule, comprising:

(a) hybridizing a primer to a first DNA molecule;

(b) contacting said DNA molecule of step (a) with deoxyribonucleoside triphosphates, the DNA polymerase of the invention, and a terminator nucleotide;

(c) incubating the mixture of step (b) under conditions sufficient to synthesize a random population of DNA molecules complementary to said first DNA molecule, wherein said synthesized DNA molecules are shorter in length than said first DNA molecule and wherein said synthesized DNA molecules comprise a terminator nucleotide at their 3' termini; and (d) separating said synthesized DNA molecules by size so that at least a part of the nucleotide sequence of said first DNA molecule can be determined. Such terminator nucleotides include ddTTP, ddATP, ddGTP, ddITP or ddCTP.

The invention also relates to a method for amplifying a double stranded DNA molecule, comprising:

(a) providing a first and second primer, wherein said first primer is complementary to a sequence at or near the 3'-termini of the first strand of said DNA molecule and said second primer is complementary to a sequence at or near the 3'-termini of the second strand of said DNA molecule;

(b) hybridizing said first primer to said first strand and said second primer to said second strand in the presence of the DNA polymerase of the invention, under conditions such that a third DNA molecule complementary to said first strand and a fourth DNA molecule complementary to said second strand are synthesized;

(c) denaturing said first and third strand, and said second and fourth strands; and (d) repeating steps (a) to (c) one or more times.

The invention also relates to a kit for sequencing a DNA molecule, comprising:

(a) a first container means comprising the DNA polymerase of the invention;

(b) a second container means comprising one or more dideoxyribonucleoside triphosphates; and (c) a third container means comprising one or more deoxyribonucleoside triphosphates.

The invention also relates to a kit for amplifying a DNA molecule, comprising:

(a) a first container means comprising the DNA polymerase of the invention; and (b) a second container means comprising one or more deoxyribonucleoside triphosphates.

The present invention also relates to a mutant DNA polymerase having substantially-reduced or eliminated 5'-3' exonuclease activity, wherein at least one of the amino acids corresponding to $Asp^8$, $Glu^{112}$, $Asp^{114}$, $Asp^{115}$, $Asp^{137}$, $Asp^{139}$, $Gly^{102}$, $Gly^{187}$, or $Gly^{195}$ of Tne DNA polymerase has been mutated.

The present invention also relates to a method of producing a mutant DNA polymerase having substantially reduced or eliminated 5'-3' exonuclease activity, wherein at least one of the amino acids corresponding to $Asp^8$, $Glu^{112}$, $Asp^{114}$, $Asp^{115}$, $Asp^{137}$, $Asp^{139}$, $Gly^{102}$, $Gly^{187}$, or $Gly^{195}$ of Tne DNA polymerase has been mutated, comprising:

(a) culturing the host cell of the invention;

(b) expressing the mutant DNA polymerase; and (c) isolating said mutant DNA polymerase.

BRIEF DESCRIPTION OF THE FIGURES

FIGS. 5A and 5B shows the nucleotide and deduced amino acid sequences, in all 3 reading frames, for the carboxyl terminal portion, including the O-helix region, of the *Thermotoga neapolitana* polymerase gene.

FIG. 8 schematically depicts the construction of plasmid pTTQTne5 FY and pTTQTne535FY.

FIG. 14A, supercoiled plasmid DNAs containing inserts with homopolymers were cycle sequenced using the mutant Tne DNA polymerase (set A, RPA1; set B, elf (cap binding protein); and set C, a poly(dC)-tailed 5' RACE-derived insert). FIG. 14B, supercoiled plasmid DNAs containing inserts with homopolymers were cycled sequenced using Taq DNA polymerase (set D), or SequiTherm™ (sets E–G) (set D, RPA; set E, RPA; set F, a poly(dC)-tailed 5' RACE-derived insert; and set G, elf).

FIGS. 17A–17C and 17D–17F depict chromatograms showing a comparison of the mutant Tne DNA polymerase of Example 12 (17A) to AmpliTaq FS™ (17B) in Fluorescent Dye Terminator Sequencing.

DETAILED DESCRIPTION OF THE PREFERRED EMBODIMENTS

Definitions

Figure 1:
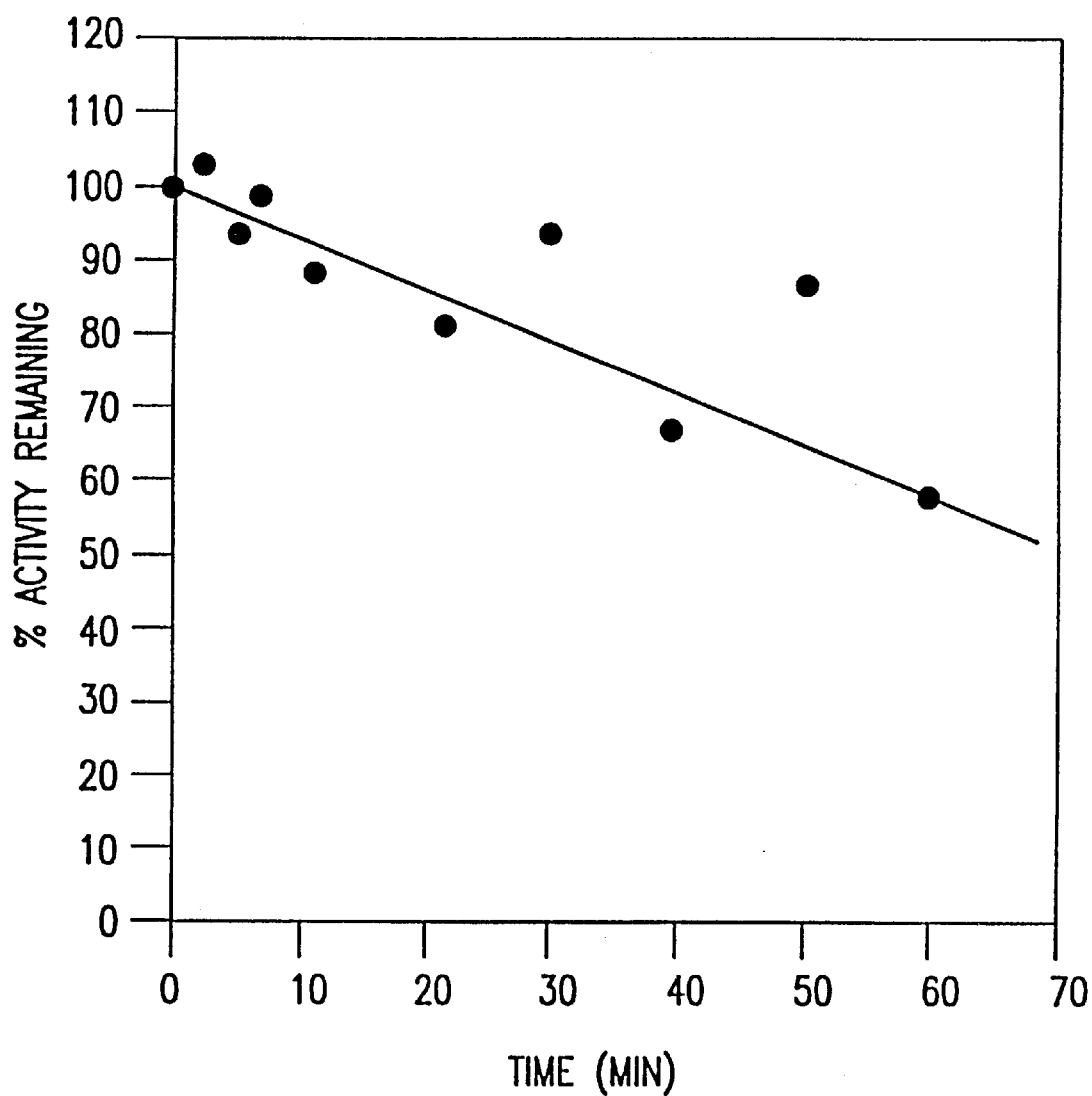
FIG. 1 demonstrates the heat stability of Tne DNA polymerase at 90° C. over time. Partially purified DNA polymerase from the crude extract of *Thermotoga neapolitana* cells was used in the assay.
Figure 2:
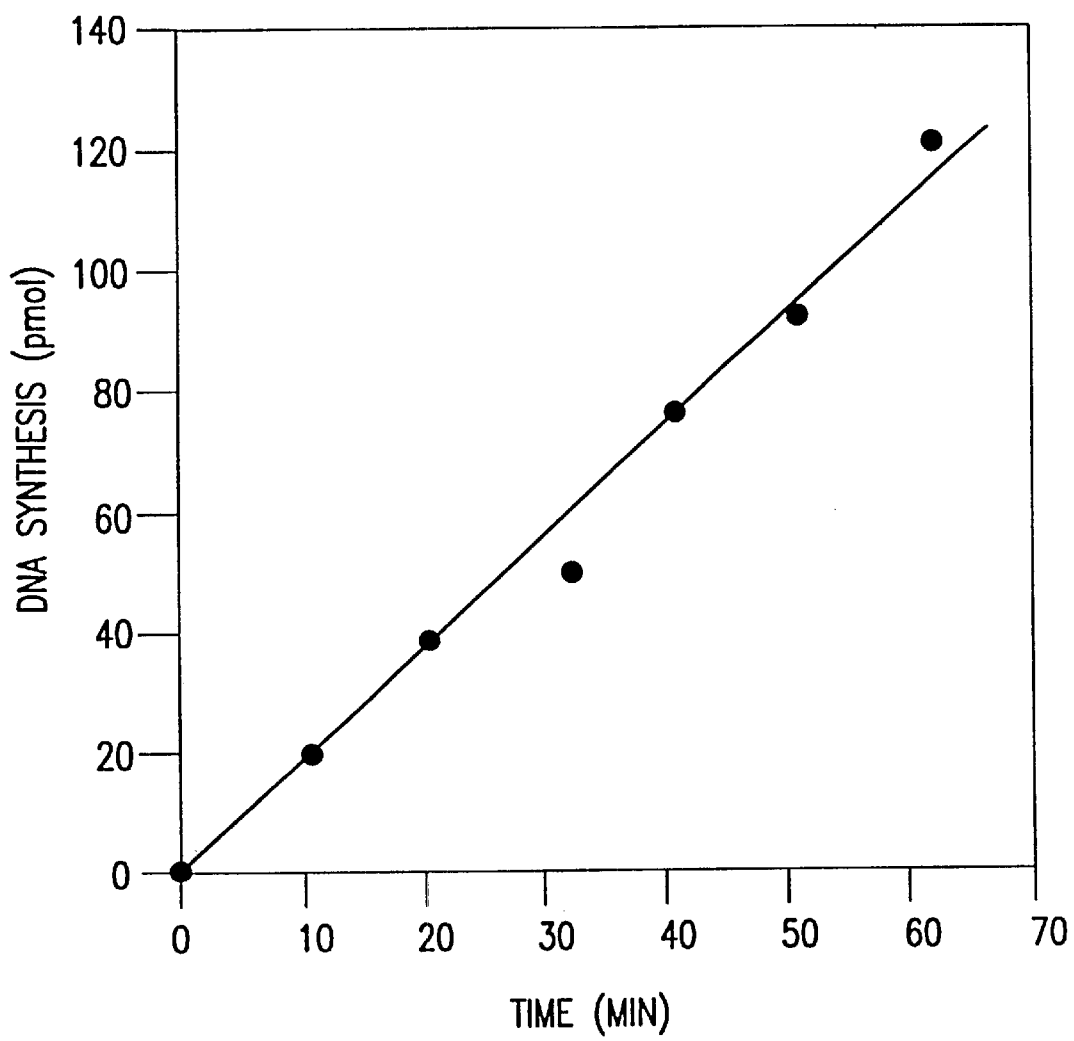
FIG. 2 shows the time-dependent DNA polymerase activity of Tne DNA polymerase isolated from an *E. coli* host containing the cloned Tne DNA polymerase gene.

In the description that follows, a number of terms used in recombinant DNA technology are extensively utilized. In order to provide a clearer and consistent understanding of the specification and claims, including the scope to be given such terms, the following definitions are provided.

Cloning vector. A plasmid, cosmid or phage DNA or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be spliced in order to bring about its replication and cloning. The cloning vector may further contain a marker suitable for use in the identification of cells transformed with the cloning vector. Markers, for example, are tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences.

Recombinant host. Any prokaryotic or eukaryotic or microorganism which contains the desired cloned genes in an expression vector, cloning vector or any DNA molecule. The term "recombinant host" is also meant to include those host cells which have been genetically engineered to contain the desired gene on the host chromosome or genome.

Host. Any prokaryotic or eukaryotic microorganism that is the recipient of a replicable expression vector, cloning vector or any DNA molecule. The DNA molecule may contain, but is not limited to, a structural gene, a promoter and/or an origin of replication.

Promoter. A DNA sequence generally described as the 5' region of a gene, located proximal to the start codon. At the promoter region, transcription of an adjacent gene(s) is initiated.

Gene. A DNA sequence that contains information necessary for expression of a polypeptide or protein. It includes the promoter and the structural gene as well as other sequences involved in expression of the protein.

Structural gene. A DNA sequence that is transcribed into messenger RNA that is then translated into a sequence of amino acids characteristic of a specific polypeptide.

Operably linked. As used herein means that the promoter is positioned to control the initiation of expression of the polypeptide encoded by the structural gene.

Expression. Expression is the process by which a gene produces a polypeptide. It includes transcription of the gene into messenger RNA (mRNA) and the translation of such mRNA into polypeptide(s).

Substantially Pure. As used herein "substantially pure" means that the desired purified protein is essentially free from contaminating cellular contaminants which are associated with the desired protein in nature. Contaminating cellular components may include, but are not limited to, phosphatases, exonucleases, endonucleases or undesirable DNA polymerase enzymes.

Primer. As used herein "primer" refers to a single-stranded oligonucleotide that is extended by covalent bonding of nucleotide monomers during amplification or polymerization of a DNA molecule.

Template. The term "template" as used herein refers to a double-stranded or single-stranded DNA molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to said template or a portion thereof. The newly synthesized DNA molecule, according to the invention, may be equal or shorter in length than the original DNA template. Mismatch incorporation during the synthesis or extension of the newly synthesized DNA molecule may result in one or a number of mismatched base pairs. Thus, the synthesized DNA molecule need not be exactly complementary to the DNA template.

Incorporating. The term "incorporating" as used herein means becoming a part of a DNA molecule or primer.

Amplification. As used herein "amplification" refers to any in vitro method for increasing the number of copies of a nucleotide sequence with the use of a DNA polymerase. Nucleic acid amplification results in the incorporation of nucleotides into a DNA molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 30 to 100 "cycles" of denaturation and synthesis of a DNA molecule.

Oligonucleotide. "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide. As used herein "nucleotide" refers to a base-sugar-phosphate combination. Nucleotides are monomeric units of a nucleic acid sequence (DNA and RNA). The term nucleotide includes deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Thermostable. As used herein "thermostable" refers to a DNA polymerase which is resistant to inactivation by heat. DNA polymerases synthesize the formation of a DNA molecule complementary to a single-stranded DNA template by extending a primer in the 5'-to-3' direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable DNA polymerase activity is more resistant to heat inactivation than a mesophilic DNA polymerase. However, a thermostable DNA polymerase does not mean to refer to an enzyme which is totally resistant to heat inactivation and thus heat treatment may reduce the DNA polymerase activity to some extent. A thermostable DNA polymerase typically will also have a higher optimum temperature than mesophilic DNA polymerases.

Hybridization. The terms "hybridization" and "hybridizing" refers to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

3'-to-5' Exonuclease Activity. "3'-to-5' exonuclease activity" is an enzymatic activity well known to the art. This activity is often associated with DNA polymerases, and is thought to be involved in a DNA replication "editing" or correction mechanism.

A "DNA polymerase substantially reduced in 3'-to-5' exonuclease activity" is defined herein as either (1) a mutated DNA polymerase that has about or less than 10%, or preferably about or less than 1%, of the 3'-to-5' exonuclease activity of the corresponding unmutated, wild-type enzyme, or (2) a DNA polymerase having a 3'-to-5' exonuclease specific activity which is less than about 1 unit/mg protein, or preferably about or less than 0.1 units/mg protein. A unit of activity of 3'-to-5' exonuclease is defined as the amount of activity that solubilizes 10 moles of substrate ends in 60 min. at 37° C., assayed as described in the "BRL 1989 Catalogue & Reference Guide", page 5, with HhaI fragments of lambda DNA 3'-end labeled with [$^3$H]dTTP by terminal deoxynucleotidyl transferase (TdT). Protein is measured by the method of Bradford, *Anal. Biochem.* 72:248 (1976). As a means of comparison, natural, wild-type T5-DNA polymerase (DNAP) or T5-DNAP encoded by pTTQ19-T5-2 has a specific activity of about 10 units/mg protein while the DNA polymerase encoded by pTTQ19-T5-2(Exo$^-$) (U.S. Pat. No. 5,270,179) has a specific activity of about 0.0001 units/mg protein, or 0.001% of the specific activity of the unmodified enzyme, a 10$^5$-fold reduction.

5'-to-3' Exonuclease Activity. "5'-to-3' exonuclease activity" is also an enzymatic activity well known in the art. This activity is often associated with DNA polymerases, such as *E. coli* PolI and PolIII.

A "DNA polymerase substantially reduced in 5'-to-3' exonuclease activity" is defined herein as either (1) a mutated DNA polymerase that has about or less than 10%, or preferably about or less than 1%, of the 5'-to-3' exonuclease activity of the corresponding unmutated, wild-type enzyme, or (2) a DNA polymerase having a 5'-to-3' exonuclease specific activity which is less than about 1 unit mg protein, or preferably about or less than 0.1 units/mg protein.

Both of the 3'-to-5' and 5'-to-3' exonuclease activities can be observed on sequencing gels. Active 5'-to-3' exonuclease activity will produce nonspecific ladders in a sequencing gel by removing nucleotides from the 5'-end of the growing primers. 3'-to-5' exonuclease activity can be measured by following the degradation of radiolabeled primers in a sequencing gel. Thus, the relative amounts of these activities, e.g. by comparing wild-type and mutant polymerases, can be determined with no more than routine experimentation.

1. Cloning and Expression of Thermotoga DNA Polymerases

The Thermotoga DNA polymerase of the invention can be isolated from any strain of Thermotoga which produces a DNA polymerase. The preferred strain to isolate the gene encoding Thermotoga DNA polymerase of the present invention is *Thermotoga neapolitana* (Tne) and *Thermotoga maritima* (Tma). The most preferred *Thermotoga neapolitana* for isolating the DNA polymerase of the invention was isolated from an African continental solfataric spring (Windberger et al., *Arch. Microbiol.* 151:506–512 (1989) and may be obtained from Deutsche Sammalung von Microorganismen und Zellkulturan GmbH (DSM; German Collection of Microorganisms and Cell Culture) Mascheroder Weg 1b D-3300 Braunschweig, Federal Republic of Germany, as Deposit No. 5068 (deposited Dec. 13, 1988).

To clone a gene encoding a Thermotoga DNA polymerase of the invention, isolated DNA which contains the polymerase gene obtained from Thermotoga cells, is used to construct a recombinant DNA library in a vector. Any vector, well known in the art, can be used to clone the wild type or mutant Thermotoga DNA polymerase of the present invention. However, the vector used must be compatible with the host in which the recombinant DNA library will be transformed.

Prokaryotic vectors for constructing the plasmid library include plasmids such as those capable of replication in *E. coli* such as, for example, pBR322, Co1E1, pSC101, pUC-vectors (pUC18, pUC19, etc.: In: *Molecular Cloning, A Laboratory Manual,* Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). Bacillus plasmids include pC194, pC221, pC217, etc. Such plasmids are disclosed by Glyczan, T. In: *The Molecular Biology Bacilli,* Academic Press, York (1982), 307–329. Suitable Streptomyces plasmids include pIJ101 (Kendall et al., *J. Bacteriol* 169:4177–4183 (1987)). Pseudomonas plasmids are reviewed by John et al, (*Rad. Insec. Dis.* 8:693–704 (1986)), and Igaki, (*Jpn. J. Bacteriol.* 33:729–742 (1978)). Broad-host range plasmids or cosmids, such as pCP13 (Darzins and Chakrabarbary, *J. Bacteriol.* 159:9–18, 1984) can also be used for the present invention. The preferred vectors for cloning the genes of the present invention are prokaryotic vectors. Preferably, pCP13 and pUC vectors are used to clone the genes of the present invention.

The preferred host for cloning the wild type or mutant DNA polymerase genes of the invention is a prokaryotic host. The most preferred prokaryotic host is *E. coli.* However, the wild type or mutant DNA polymerase genes of the present invention may be cloned in other prokaryotic hosts including, but not limited to, Escherichia, Bacillus, Streptomyces, Pseudomonas, Salmonella, Serratia, and Proteus. Bacterial hosts of particular interest include *E. coli* DH10B, which may be obtained from Life Technologies, Inc. (LTI) (Gaithersburg, Md.).

Eukaryotic hosts for cloning and expression of the wild type or mutant DNA polymerases of the present invention include yeast, fungi, and mammalian cells. Expression of the desired DNA polymerase in such eukaryotic cells may require the use of eukaryotic regulatory regions which include eukaryotic promoters. Cloning and expressing the wild type or mutant DNA polymerase gene of the invention in eukaryotic cells may be accomplished by well known techniques using well known eukaryotic vector systems.

Once a DNA library has been constructed in a particular vector, an appropriate host is transformed by well known techniques. Transformed colonies are plated at a density of approximately 200–300 colonies per petri dish. Colonies are then screened for the expression of a heat stable DNA polymerase by transferring transformed *E. coli* colonies to nitrocellulose membranes. After the transferred cells are grown on nitrocellulose (approximately 12 hours), the cells are lysed by standard techniques, and the membranes are then treated at 95° C. for 5 minutes to inactivate the endogenous *E. coli* enzyme. Other temperatures may be used to inactivate the host polymerases depending on the host used and the temperature stability of the DNA polymerase to be cloned. Stable DNA polymerase activity is then detected by assaying for the presence of DNA polymerase activity using well known techniques. Sagner et al., *Gene* 97:119–123 (1991), which is hereby incorporated by reference in its entirety. The gene encoding a DNA polymerase of the present invention can be cloned using the procedure described by Sagner et al., supra.

The recombinant host containing the wild type gene encoding Tne DNA polymerase, *E. coli* DH10B (pUC-Tne), was deposited on Sep. 30, 1994, with the Collection, Agricultural Research Culture Collection (NRRL), 1815 North University Street, Peoria, Ill. 61604 USA as Deposit No. NRRL B-21338. The gene encoding Tma DNA polymerase has also been cloned and sequenced (U.S. Pat. No. 5,374,553, which is expressly incorporated by reference in its entirety).

If the Thermotoga (e.g., Tne or Tma) DNA polymerase has 3'-to-5' exonuclease activity, this activity may be reduced, substantially reduced, or eliminated by mutating the DNA polymerase gene. Such mutations include point mutations, frame shift mutations, deletions and insertions. Preferably, the region of the gene encoding the 3'-to-5' exonuclease activity is mutated or deleted using techniques well known in the art (Sambrook et al., (1989) in: *Molecular Cloning, A Laboratory Manual* (2nd Ed.), Cold Spring Harbor Laboratory Press, Cold Spring Harbor, N.Y.).

The 3'-to-5' exonuclease activity can be reduced or impaired by creating site specific mutants within the 3'→5' exonuclease domain. See infra. In a specific embodiment of the invention $Asp^{323}$ of Tne DNA polymerase (SEQ ID NO. 3) is changed to any amino acid, preferably to $Ala^{323}$ to substantially reduce 3'-to-5' exonuclease activity. In another specific embodiment of the invention, $Asp^{323}$ of Tma may be changed to any other amino acid, preferably to Ala to substantially reduce 3'-to-5' exonuclease activity.

The 5'→3' exonuclease activity of the DNA polymerase can be reduced or eliminated by mutating the DNA polymerase gene. Such mutations include point mutations, frame shift mutations, deletions, and insertions. Preferably, the region of the gene encoding the 5'→3' exonuclease activity is deleted using techniques well known in the art. In embodiments of this invention, any one of six conserved amino acids that are associated with the 5'→3' exonuclease activity can be mutated. Examples of these conserved amino acids with respect to Tne DNA polymerase include $Asp^8$, $Glu^{112}$, $Asp^{114}$, $Asp^{115}$, $Asp^{137}$, and $Asp^{139}$. Other possible sites for mutation are: $Gly^{102}$, $Gly^{187}$ and $Gly^{195}$.

The present invention is directed broadly to mutations of DNA polymerases that result in the reduction or elimination of 5'-3' exonuclease activity. Other particular mutations correspond to the following amino acids.

*E. coli* polI: $Asp^{13}$, $Glu^{113}$, $Asp^{115}$, $Asp^{116}$, $Asp^{138}$, and $Asp^{140}$.
Taq pol: $Asp^{18}$, $GluI^{117}$, $Asp^{119}$, $Asp^{120}$, $Asp^{142}$, and $Asp^{144}$.
Tma pol: $Asp^8$, $Glu^{112}$, $Asp^{114}$, $Asp^{115}$, $Asp^{137}$, and $Asp^{139}$.

Amino acid residues of Taq DNA polymerase are as numbered in U.S. Pat. No. 5,079,352.

Amino acid residues of *Thermotoga maritima* (Tma) DNA polymerase are numbered as in U.S. Pat. No. 5,374,553.

By comparison to the amino acid sequence of other DNA polymerases, the corresponding sites can easily be located and the DNA mutanigized to prepare a coding sequence for the corresponding DNA polymerase which lacks the 5'→3' exonuclease activity. Examples of other DNA polymerases that can be so mutated include:

| Enzyme or source | Mutation positions |
|---|---|
| Streptococcus pneumoniae | $Asp^{10}$, $Glu^{114}$, $Asp^{116}$, $Asp^{117}$, $Asp^{139}$, $Asp^{141}$ |
| Thermus flavus | $Asp^{17}$, $Glu^{116}$, $Asp^{118}$, $Asp^{119}$, $Asp^{141}$, $Asp^{143}$ |
| Thermus thermophilus | $Asp^{18}$, $Glu^{118}$, $Asp^{120}$, $Asp^{121}$, $Asp^{143}$, $Asp^{145}$ |
| Deinococcus radiodurans | $Asp^{18}$, $Glu^{117}$, $Asp^{119}$, $Asp^{120}$, $Asp^{142}$, $Asp^{144}$ |
| Bacillus caldotenax | $Asp^9$, $Glu^{109}$, $Asp^{111}$, $Asp^{112}$, $Asp^{134}$, $Asp^{136}$ |

Coordinates of *S. pneumoniae, T. flavus, D. radiodurans, B. caldotenax* were obtained from Gutman and Minton. Coordinates of *T. thermophilus* were obtained from International Patent No. WO 92/06200.

To abolish the 5'-3' exonuclease activity, amino acids are selected which have different properties. For example, an acidic amino acid such as Asp may be changed to a basic, neutral or polar but uncharged amino acid such as Lys, Arg, His (basic); Ala, Val, Leu, Ile, Pro, Met, Phe, Trp (neutral); or Gly, Ser, Thr, Cys, Tyr, Asn or Gln (polar but uncharged). Glu may be changed to Asp, Ala, Val Leu, Ile, Pro, Met, Phe, Trp, Gly, Ser, Thr, Cys, Tyr, Asn or Gln. Specifically, the Ala substitution in the corresponding position is expected to abolish 5'-exo activity.

Preferably, oligonucleotide directed mutagenesis is used to create the mutant DNA polymerase which allows for all possible classes of base pair changes at any determined site along the encoding DNA molecule. In general, this technique involves annealing a oligonucleotide complementary (except for one or more mismatches) to a single stranded nucleotide sequence coding for the DNA polymerase of interest. The mismatched oligonucleotide is then extended by DNA polymerase, generating a double stranded DNA molecule which contains the desired change in sequence on one strand. The changes in sequence can of course result in the deletion, substitution, or insertion of an amino acid. The double stranded polynucleotide can then be inserted into an appropriate expression vector, and a mutant polypeptide can thus be produced. The above-described oligonucleotide directed mutagenesis can of course be carried out via PCR.

In other embodiments, the entire 5'→3' exonuclease domain of the DNA polymerase can be deleted by proteolytic cleavage or by genetic engineering. For example, a unique SphI restriction site can be used to obtain a clone devoid of nucleotides encoding the 219 amino terminal amino acids of Tne DNA polymerase. Examples of such a clone are pTTQTne535FY and pTTQTne5FY. Alternatively, less than the 219 amino terminal amino acids may be removed, for example, by treating the DNA coding for the Tne DNA polymerase with an exonuclease, isolating the fragments, ligating the fragments into a cloning vehicle, transfecting cells with the cloning vehicle, and screening the transformants for DNA polymerase activity and lack of 5'→3' exonuclease activity, with no more than routine experimentation.

Thermotoga DNA polymerase mutants can also be made to render the polymerase non-discriminating against non-natural nucleotides such as dideoxynucleotides. Changes within the O-helix of Thermotoga polymerases, such as other point mutations, deletions, and insertions, can be made to render the polymerase non-discriminating. By way of example, one Tne DNA polymerase mutant having this property substitutes a nonnatural amino acid such as Tyr for Phe at amino acid 67 as numbered in FIGS. 5A and 5B, and 730 of SEQ ID NO:3.

The O-helix region is a 14 amino acid sequence corresponding to amino acids 722–735 of SEQ ID NO:3 or amino acids 59–72 as numbered in FIGS. 5A and 5B. The O-helix may be defined as RXXXKXXXFXXXYX, wherein X is any amino acid. The most important amino acids in conferring discriminatory activity include Arg, Lys and Phe. Amino acids which may be substituted for Arg at positions 722 are selected independently from Asp, Glu, Ala, Val Leu, Ile, Pro, Met, Phe, Trp, Gly, Ser, Thr, Cys, Tyr, Gln, Asn, Lys and His. Amino acids that may be substituted for Phe at position 730 include Lys, Arg, His, Asp, Glu, Ala, Val, Leu, Ile, Pro, Met, Trp, Gly, Ser, Thr, Cys, Tyr, Asn or Gln. Amino acids that may be substituted for Lys at position 726 of SEQ ID NO: 3 include Tyr, Arg, His, Asp, Glu, Ala, Val, Leu, Ile, Pro, Met, Trp, Gly, Ser, Thr, Cys, Phe, Asn or Gln. Preferred mutants include $Tyr^{730}$, $Ala^{730}$, $Ser^{730}$ and $Thr^{730}$. Such Tne mutants may be prepared by well known methods of site directed mutagenesis as described herein. See also Example 10.

The corresponding mutants can also be prepared from Tma DNA polymerase, including $Arg^{722}$, $Lys^{726}$ and $Phe^{730}$. Most prefered mutants include $Phe^{730}$ to $Tyr^{730}$, $Ser^{730}$, $Thr^{730}$ and $Ala^{730}$.

2. Enhancing Expression of Thermotoga DNA Polymerase

To optimize expression of the wild type or mutant Thermotoga DNA polymerases of the present invention, inducible or constitutive promoters are well known and may be used to express high levels of a polymerase structural gene in a recombinant host. Similarly, high copy number vectors, well known in the art, may be used to achieve high levels of expression. Vectors having an inducible high copy number may also be usefull to enhance expression of Thermotoga DNA polymerase in a recombinant host.

To express the desired structural gene in a prokaryotic cell (such as, E. coli, B. subtilis, Pseudomonas, etc.), it is necessary to operably link the desired structural gene to a functional prokaryotic promoter. However, the natural Thermotoga promoter may function in prokaryotic hosts allowing expression of the polymerase gene. Thus, the natural Thermotoga promoter or other promoters may be used to express the DNA polymerase gene. Such other promoters may be used to enhance expression and may either be constitutive or regulatable (i.e., inducible or derepressible) promoters. Examples of constitutive promoters include the int promoter of bacteriophage λ, and the bla promoter of the β-lactamase gene of pBR322. Examples of inducible prokaryotic promoters include the major right and left promoters of bacteriophage λ ($P_R$ and $P_L$), trp, recA, lacZ, lacI, tet, gal, trc, and tac promoters of E. coli. The B. subtilis promoters include α-amylase (Ulmanen et al., J. Bacteriol 162:176–182 (1985)) and Bacillus bacteriophage promoters (Gryczan, T., In: The Molecular Biology Of Bacilli, Academic Press, New York (1982)). Streptomyces promoters are described by Ward et al., Mol. Gen. Genet. 203:468478 (1986)). Prokaryotic promoters are also reviewed by Glick, J. Ind. Microbiol. 1:277–282 (1987); Cenatiempto, Y., Biochimie 68:505–516 (1986); and Gottesman, Ann. Rev. Genet. 18:415–442 (1984). Expression in a prokaryotic cell also requires the presence of a ribosomal binding site upstream of the gene-encoding sequence. Such ribosomal binding sites are disclosed, for example, by Gold et al., Ann. Rev. Microbiol. 35:365404 (1981).

To enhance the expression of Thermotoga (e.g., The and Tma) DNA polymerase in a eukaryotic cell, well known eukaryotic promoters and hosts may be used. Preferably, however, enhanced expression of Thermotoga DNA polymerase is accomplished in a prokaryotic host. The preferred prokaryotic host for overexpressing this enzyme is E. coli.

3. Isolation and Purification of Thermotoga DNA Polymerase

The enzyme(s) of the present invention (Thermotoga DNA polymerases and mutants thereof) is preferably produced by fermentation of the recombinant host containing and expressing the cloned DNA polymerase gene. However, the wild type and mutant DNA polymerases of the present invention may be isolated from any Thermotoga strain which produces the polymerase of the present invention. Fragments of the polymerase are also included in the present invention. Such fragments include proteolytic fragments and fragments having polymerase activity.

Any nutrient that can be assimilated by Thermotoga or a host containing the cloned Thermotoga DNA polymerase gene may be added to the culture medium. Optimal culture conditions should be selected case by case according to the strain used and the composition of the culture medium. Antibiotics may also be added to the growth media to insure maintenance of vector DNA containing the desired gene to be expressed. Culture conditions for Thermotoga neapolitana have, for example, been described by Huber et al., Arch. Microbiol. 144:324–333 (1986). Media formulations are also described in DSM or ATCC Catalogs and Sambrook et al., In: Molecular Cloning, a Laboratory Manual (2nd ed.), Cold Spring Harbor Laboratory Press, Cold Spring Harbor, N.Y. (1989).

Thermotoga and recombinant host cells producing the DNA polymerase of this invention can be separated from liquid culture, for example, by centrifugation. In general, the collected microbial cells are dispersed in a suitable buffer, and then broken down by ultrasonic treatment or by other well known procedures to allow extraction of the enzymes by the buffer solution. After removal of cell debris by ultracentrifugation or centrifugation, the DNA polymerase can be purified by standard protein purification techniques such as extraction, precipitation, chromatography, affinity chromatography, electrophoresis or the like. Assays to detect the presence of the DNA polymerase during purification are well known in the art and can be used during conventional biochemical purification methods to determine the presence of these enzymes.

4. Uses of Thermotoga DNA Polymerase

The wild type and mutant Thermotoga DNA polymerases (e.g., Tma and Tne) of the present invention may be used in well known DNA sequencing, DNA labeling, DNA amplification and cDNA synthesis reactions. Thermotoga DNA polymerase mutants devoid of or substantially reduced in 3'→5' exonuclease activity, devoid of or substantially reduced in 5'→3' exonuclease activity, or containing one or mutations in the O-helix that make the enzyme nondiscriminatory for dNTPs and ddNTPs (e.g., a $Phe^{730} \rightarrow Tyr^{730}$ mutation of SEQ ID NO: 3) are especially useful for DNA sequencing, DNA labeling, and DNA amplification reactions and cDNA synthesis. Moreover, Thermotoga DNA polymerase mutants containing two or more of these properties are also especially useful for DNA sequencing, DNA labeling, DNA amplification or cDNA synthesis reactions. As is well known, sequencing reactions (isothermal DNA sequencing and cycle sequencing of DNA) require the use of DNA polymerases. Dideoxy-mediated sequencing involves the use of a chain-termination technique which uses a specific polymer for extension by DNA polymerase, a base-specific chain terminator and the use of polyacrylamide gels to separate the newly synthesized chain-terminated DNA molecules by size so that at least a part of the nucleotide sequence of the original DNA molecule can be determined. Specifically, a DNA molecule is sequenced by using four separate DNA sequence reactions, each of which contains different base-specific terminators. For example, the first reaction will contain a G-specific terminator, the second reaction will contain a T-specific terminator, the third reaction will contain an A-specific terminator, and a fourth reaction may contain a C-specific terminator. Preferred terminator nucleotides include dideoxyribonucleoside triphosphates (ddNTPs) such as ddATP, ddTTP, ddGTP, ddITP and ddCTP. Analogs of dideoxyribonucleoside triphosphates may also be used and are well known in the art.

When sequencing a DNA molecule, ddNTPs lack a hydroxyl residue at the 3' position of the deoxyribose base and thus, although they can be incorporated by DNA polymerases into the growing DNA chain, the absence of the 3'-hydroxy residue prevents formation of the next phosphodiester bond resulting in termination of extension of the DNA molecule. Thus, when a small amount of one ddNTP is included in a sequencing reaction mixture, there is competition between extension of the chain and base-specific termination resulting in a population of synthesized DNA molecules which are shorter in length than the DNA template to be sequenced. By using four different ddNTPs in four separate enzymatic reactions, populations of the synthesized DNA molecules can be separated by size so that at least a part of the nucleotide sequence of the original DNA molecule can be determined. DNA sequencing by dideoxynucleotides is well known and is described by Sambrook et al., In: *Molecular Cloning, a Laboratory Manual,* Cold Spring Harbor Laboratory Press, Cold Spring Harbor, N.Y. (1989). As will be readily recognized, the Thermotoga DNA polymerases and mutants thereof of the present invention may be used in such sequencing reactions.

As is well known, detectably labeled nucleotides are typically included in sequencing reactions. Any number of labeled nucleotides can be used in sequencing (or labeling) reactions, including, but not limited to, radioactive isotopes, fluorescent labels, chemiluminescent labels, bioluminescent labels, and enzyme labels. It has been discovered that the wild type and mutant DNA polymerase of the present invention may be useful for incorporating αS nucleotides ([αS]dATP, [αS]dTTP, [αS]dCTP and [αS]dGTP) during sequencing (or labeling) reactions. For example, [$\alpha^{35}$S] dATP, a commonly used detectably labeled nucleotide in sequencing reactions, is incorporated three times more efficiently with the Tne DNA polymerase of the present invention, than with Taq DNA polymerase. Thus, the enzyme of the present invention is particularly suited for sequencing or labeling DNA molecules with [$\alpha^{35}$S]dNTPs.

Polymerase chain reaction (PCR), a well known DNA amplification technique, is a process by which DNA polymerase and deoxyribonucleoside triphosphates are used to amplify a target DNA template. In such PCR reactions, two primers, one complementary to the 3' termini (or near the 3'-termini) of the first strand of the DNA molecule to be amplified, and a second primer complementary to the 3' termini (or near the 3'-termini) of the second strand of the DNA molecule to be amplified, are hybridized to their respective DNA strands. After hybridization, DNA polymerase, in the presence of deoxyribonucleoside triphosphates, allows the synthesis of a third DNA molecule complementary to the first strand and a fourth DNA molecule complementary to the second strand of the DNA molecule to be amplified. This synthesis results in two double stranded DNA molecules. Such double stranded DNA molecules may then be used as DNA templates for synthesis of additional DNA molecules by providing a DNA polymerase, primers, and deoxyribonucleoside triphosphates. As is well known, the additional synthesis is carried out by "cycling" the original reaction (with excess primers and deoxyribonucleoside triphosphates) allowing multiple denaturing and synthesis steps. Typically, denaturing of double stranded DNA molecules to form single stranded DNA templates is accomplished by high temperatures. The wild type and mutant Thermotoga DNA polymerases of the present invention are heat stable DNA polymerases, and thus will survive such thermal cycling during DNA amplification reactions. Thus, the wild type and mutant DNA polymerases of the invention are ideally suited for PCR reactions, particularly where high temperatures are used to denature the DNA molecules during amplification.

The Thermotoga DNA polymerase and mutants of the present invention (e.g. Tne and Tma) may also be used to prepare cDNA from mRNA templates. See, U.S. Pat. Nos. 5,405,776 and 5,244,797, the disclosures of which are explicitly incorporated by reference herein. Thus, the invention also relates to a method of preparing cDNA from mRNA, comprising (a) contacting mRNA with an oligo(dT) primer or other complementary primer to form a hybrid, and (b) contacting said hybrid formed in step (a) with the Thermotoga DNA polymerase or mutant of the invention and the four dNTPs, whereby a cDNA-RNA hybrid is obtained.

If the reaction mixture is step (b) further comprises an appropriate oligonucleotide which is complementary to the cDNA being produced, it is also possible to obtain dsDNA following first strand synthesis. Thus, the invention is also directed to a method of preparing dsDNA with the Thermotoga DNA polymerases and mutants thereof of the present invention.

5. Kits

The wild type and mutant Thermotoga DNA polymerases of the invention are suited for the preparation of a kit. Kits comprising the wild type or mutant DNA polymerase(s) may be used for detectably labeling DNA molecules, DNA sequencing, amplifying DNA molecules or cDNA synthesis by well known techniques, depending on the content of the kit. See U.S. Pat. Nos. 4,962,020, 5,173,411, 4,795,699, 5,498,523, 5,405,776 and 5,244,797. Such kits may comprise a carrying means being compartmentalized to receive in close confinement one or more container means such as vials, test tubes and the like. Each of such container means comprises components or a mixture of components needed to perform DNA sequencing, DNA labeling, DNA amplification, or cDNA synthesis.

A kit for sequencing DNA may comprise a number of container means. A first container means may, for example, comprise a substantially purified sample of Thermotoga DNA polymerases or mutants thereof. A second container means may comprise one or a number of types of nucleotides needed to synthesize a DNA molecule complementary to DNA template. A third container means may comprise one or a number of different types of dideoxynucleoside triphosphates. A fourth container means may comprise pyrophosphatase. In addition to the above container means, additional container means may be included in the kit which comprise one or a number of DNA primers.

A kit used for amplifying DNA will comprise, for example, a first container means comprising a substantially pure mutant or wild type Thermotoga DNA polymerase of the invention and one or a number of additional container means which comprise a single type of nucleotide or mixtures of nucleotides. Various primers may or may not be included in a kit for amplifying DNA.

Kits for cDNA synthesis will comprise a first container means containing the wild type or mutant Tne DNA polymerase of the invention, a second container means will contain the four dNTPs and the third container means will contain oligo(dT) primer. See U.S. Pat. Nos. 5,405,776 and 5,244,797. Since the Thermotoga DNA polymerases of the present invention are also capable of preparing dsDNA, a fourth container means may contain an appropriate primer complementary to the first strand cDNA.

Of course, it is also possible to combine one or more of these reagents in a single tube. A detailed description of such formulations at working concentrations is described in the patent application entitled "Stable Compositions for Nucleic Acid Amplification and Sequencing" filed on Aug. 14, 1996, which is expressly incorporated by reference herein in its entirety.

When desired, the kit of the present invention may also include container means which comprise detectably labeled nucleotides which may be used during the synthesis or sequencing of a DNA molecule. One of a number of labels may be used to detect such nucleotides. Illustrative labels include, but are not limited to, radioactive isotopes, fluorescent labels, chemiluminescent labels, bioluminescent labels and enzyme labels.

6. Advantages of the Thermotoga DNA Polymerase

Thermotoga DNA polymerases of the invention have distinct advantages in DNA sequencing. For example, when using the Tne DNA polymerase mutants of the invention in single-extension sequencing, they generate strong, clear $^{35}$S-labeled sequence, increase sequence signal to background ratio, generate $\geq 500$ bases of sequence, reduce false stops in the sequencing ladder, and permit high temperature sequencing reactions. The efficient $^{35}$S incorporation by the Tne DNA polymerase mutants of the invention can reduce template requirement 10-fold, give sharper bands than $^{32}$P, emit lower energy radiation than $^{32}$P, and have a longer shelf life than $^{32}$P. Further, the Tne polymerase mutants produce longer sequence reads and gives more accurate sequence interpretation. In addition, the use of a 70° C. reaction temperature with this thermophilic polymerase increases sequencing efficiency of structure-containing and GC-rich templates.

Compared to modified T7 DNA polymerase (Sequenase™), Tne DNA polymerase mutants allow improved sequencing efficiency of structure containing and GC-rich templates, are more forgiving in incubation times for labeling and extensions, and allow one to obtain full length sequence from one-tenth the amount of template. With regard to other polymerases, the Tne DNA polymerase mutants provide, under appropriate reaction conditions, more even band intensities and give longer, more accurate sequence reads, exhibit no weak or absent "dropout" bands, exhibit improved sequencing efficiency of structure containing and GC-rich templates, exhibit no sequence artifacts from templates containing homopolymers, and provide for shorter film exposure and/or less template input due to the efficient $^{35}$S-dNTP incorporation.

With regard to cycle sequencing, the Tne DNA polymerase mutants generate strong, clear $^{35}$S-labeled sequence, they increase sequence signal to background ratio, generate $\geq 500$ bases of sequence, reduce false stops in the sequencing ladder under appropriate conditions, and permit high temperature reactions. The Tne DNA polymerase mutants also allow for highly efficient $^{35}$S dATP incorporation and therefore shorter film exposures and/or less template input, give sharper bands than $^{32}$P, give off lower energy radiation than $^{32}$P and have a longer shelf life than 32P. The Tne DNA polymerase mutants also produce longer sequence reads and give more accurate sequence interpretation. $^{32}$P end labeling of primers generates data with less background from less pure DNA and requires as little as 5 fmole (0.01 µg) of DNA.

With regard to cycle sequencing, compared to the mutant Taq DNA polymerase (ThermoSequenase™), the Tne DNA polymerase mutants generate three times stronger $^{35}$S-labeled sequence without an extra 2 hour cycled labeling step, require no special primer design for $^{35}$S labeling, and allow for sequencing of PCR products directly using any primer. Compared to SequiTherm™, the mutants of Tne DNA polymerase generate three times stronger $^{35}$S-labeled sequence, give more even band intensities, gives longer and more accurate sequence reads, require less template and less primer, and give no sequence artifacts from templates containing homopolymers. Compared to various other polymerases (e.g. Tth DNA polymerase), the Tne DNA polymerase mutants under appropriate reaction conditions generate three times stronger $^{35}$S-labeled sequence, give more even band intensities, give longer and more accurate sequence reads, give no weak or absent "dropout" bands, improve sequencing efficiency of structure-containing and GC-rich templates, and reduce false stops in sequencing ladders, including through homopolymer regions.

With regard to fluorescent sequencing, the mutants of Tne DNA polymerase readily accept dye primers and dye terminators, increase sequence signal to background ratio, produce fewer ambiguous calls, and generate $\geq 500$ bases of sequence. The Tne DNA polymerase mutants also produce longer sequence read lengths, give more accurate sequence interpretation, and allow for quantitation of bases in heterologous mixtures. Since the Tne DNA polymerase mutants provide for good incorporation of dye terminators, such dye terminators can be reduced 500-fold. Further, increased signal improves bases calling, reduces cost and time to sequence, eliminates the need to remove excess dye terminators before gel loading, and produces more even band intensities. The efficient use of dye primers generates data with less background from impure DNA and requires as little as 0.6 µg of dsDNA (double-stranded DNA).

With regard to the use of Thermo Sequenase™ and AmpliTaq FS™ in fluorescent sequencing, the Tne DNA polymerase mutants provide more even band intensities in dye terminator sequencing and give comparable results with dye primers. With regard to SequiTherm™, the Tne DNA polymerase mutants give more even band intensities that give longer, more accurate sequencing reads with both dye terminators and dye primers, use 500-fold less dye terminators, eliminate post reaction clean up of dye terminators, require 10-fold less template, and allow for quantitation of bases in heterologous mixtures using dye primers.

With regard to the use of various other enzymes in fluorescent sequencing, such as AmpliTaq™ and AmpliTaqCS™, mutant Tne DNA polymerases under appropriate reaction conditions provide more even band intensities and more accurate sequence reads with both dye terminators and dye primers, give no weak or absent "dropout" bands, have lower background and fewer false stops, use 500-fold less dye terminators, eliminate post reaction clean up of dye terminators, require 10-fold less template, and allow for quantitation of bases in heterologous mixtures.

Figure 3:
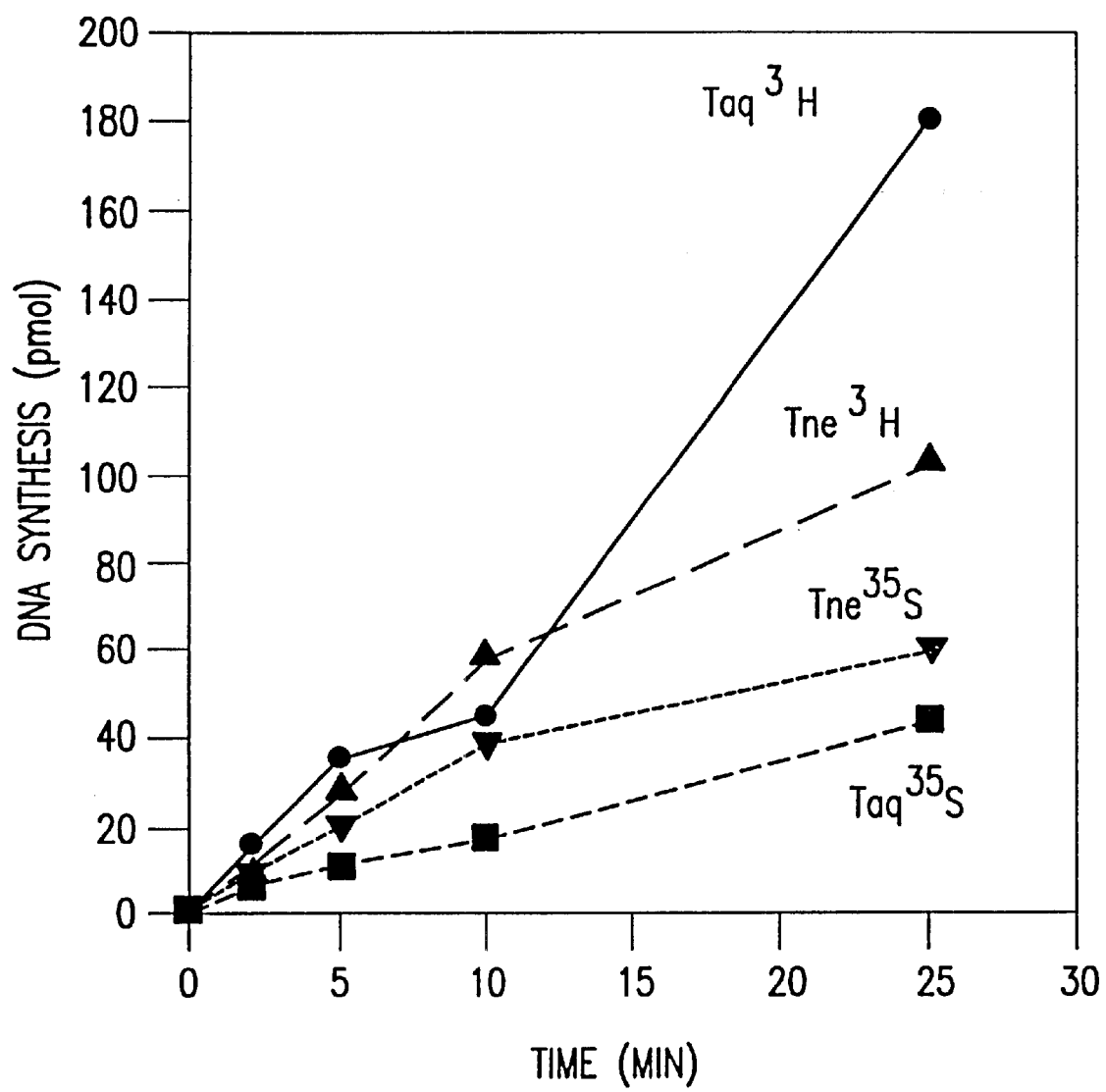
FIG. 3 compares the ability of various DNA polymerases to incorporate radioactive dATP and [αS]dATP. Tne DNA polymerase is more effective at incorporating [αS]dATP than was Taq DNA polymerase.

As shown in FIG. 3, Tne DNA polymerase incorporates α-thio dATP at three times the rate of Taq DNA polymerase. However, surprisingly, when α-thio dATP is used in place of dATP in sequencing reactions using [α-$^{35}$S]dATP and mutants of Tne DNA polymerase, the resulting sequencing band signal intensity is increased by approximately 8–10 fold. The weak signal seen when dATP is used reflects the mutant DNA polymerase's strong preference for incorporating dATP over α-thio dATP from a mixed pool. Attempts to improve signal intensity by merely decreasing the amount of dATP resulted in very poor quality sequence with many false stops. Parallel experiments with [α-$^{32}$P]dATP and low concentrations of dATP produced similar poor quality sequence, indicating that the nucleotide concentration imbalance was causing the enzyme to perform poorly. By using α-thio dATP mixed with [α-$^{35}$S]dATP, the four nucleotide concentrations kept constant without diminishing signal or sequence quality.

Having now generally described the invention, the same will be more readily understood through reference to the following Examples which are provided by way of illustration, and are not intended to be limiting of the present invention, unless specified.

EXAMPLE 1
Bacterial Strains And Growth Conditions

*Thermotoga neapolitana* DSM No. 5068 was grown under anaerobic conditions as described in the DSM catalog (addition of resazurin, Na$_2$S, and sulfur granules while sparging the media with nitrogen) at 85° C. in an oil bath from 12 to 24 hours. The cells were harvested by filtering the broth through Whatman #1 filter paper. The supernatant was collected in an ice bath and then centrifuged in a refrigerated centrifuge at 8,000 rpms for twenty minutes. The cell paste was stored at −70° C. prior to total genomic DNA isolation.

*E. coli* strains were grown in 2× LB broth base (Lennox L broth base: GIBCO/BRL) medium. Transformed cells were incubated in SOC (2% tryptone, 0.5% yeast extract, yeast 10 mM NaCl, 2.5 mM KCl, 20 mM glucose, 10 mM MgCl$_2$, and 10 mM MgSO$_4$ per liter) before plating. When appropriate antibiotic supplements were 20 mg/l tetracycline and 100 mg/l ampicillin. *E. coli* strain DH10B (Lorow et al., *Focus* 12:19–20 (1990)) was used as host strain. Competent DH10B may be obtained from Life Technologies, Inc. (LTI) (Gaithersburg, Md.).

EXAMPLE 2
DNA Isolation

*Thermotoga neapolitana* chromosomal DNA was isolated from 1.1 g of cells by suspending the cells in 2.5 ml TNE (50 mM Tris-HCl, pH 8.0, 50 mM NaCl, 10 mM EDTA) and treated with 1% SDS for 10 minutes at 37° C. DNA was extracted with phenol by gently rocking the lysed cells overnight at 4° C. The next day, the lysed cells were extracted with chloroform:isoamyl alcohol. The resulting chromosomal DNA was further purified by centrifugation in a CsCl density gradient. Chromosomal DNA isolated from the density gradient was extracted three times with isopropanol and dialyzed overnight against a buffer containing 10 mM Tris-HCl (pH 8.0) and 1 mM EDTA (TE).

EXAMPLE 3
Construction of Genomic Libraries

The chromosomal DNA isolated in Example 2 was used to construct a genomic library in the plasmid pCP13. Briefly, 10 tubes each containing 10 μg of *Thermotoga neapolitana* chromosomal DNA was digested with 0.01 to 10 units of Sau3Al for 1 hour at 37° C. A portion of the digested DNA was tested in an agarose (1.2%) gel to determine the extent of digestion. Samples with less than 50% digestion were pooled, ethanol precipitated and dissolved in TE. 6.5 μg of partially digested chromosomal DNA was ligated into 1.5 μg of pCP13 cosmid which had been digested with BamHI restriction endonuclease and dephosphorylated with calf intestinal alkaline phosphatase. Ligation of the partially digested Thermotoga DNA and BamHI cleaved pCP13 was carried out with T4 DNA ligase at 22° C. for 16 hours. After ligation, about 1 μg of ligated DNA was packaged using λ-packaging extract (obtained from Life Technologies, Inc., Gaithersburg, Md.). DH10B cells (Life Tech. Inc.) were then infected with 100 μl of the packaged material. The infected cells were plated on tetracycline containing plates. Serial dilutions were made so that approximately 200 to 300 tetracycline resistant colonies were obtained per plate.

EXAMPLE 4
Screening for Clones Expressing *Thermotoga neapolitana* DNA Polymerase Identification of the *Thermotoga neapolitana* DNA polymerase gene of the invention was cloned using the method of Sagner et al., *Gene* 97:119–123 (1991) which reference is herein incorporated in its entirety. Briefly, the *E. coli* tetracycline resistant colonies from Example 3 were transferred to nitrocellulose membranes and allowed to grow for 12 hours. The cells were then lysed with the fumes of chloroform:toluene (1:1) for 20 minutes and dried for 10 minutes at room temperature. The membranes were then treated at 95° C. for 5 minutes to inactivate the endogenous *E. coli* enzymes. Surviving DNA polymerase activity was detected by submerging the membranes in 15 ml of polymerase reaction mix (50 mM Tris-HCl (pH 8.8), 1 mM MgCl$_2$, 3 mM β-mercaptoethanol, 10 μM dCTP, dGTP, dTTP, and 15 μCi of 3,000 Ci/mmol [α$^{32}$P]dATP) for 30 minutes at 65° C.

Using autoradiography, three colonies were identified that expressed a *Thermotoga neapolitana* DNA polymerase. The cells were grown in liquid culture and the protein extract was made by sonication. The presence of the cloned thermostable polymerase was confirmed by treatment at 90° C. followed by measurement of DNA polymerase activity at 72° C. by incorporation of radioactive deoxyribonucleoside triphosphates into acid insoluble DNA. One of the clones, expressing Tne DNA polymerase, contained a plasmid designated pCP13-32 and was used for further study.

EXAMPLE 5
Subcloning of Tne DNA Polymerase

Figure 4:
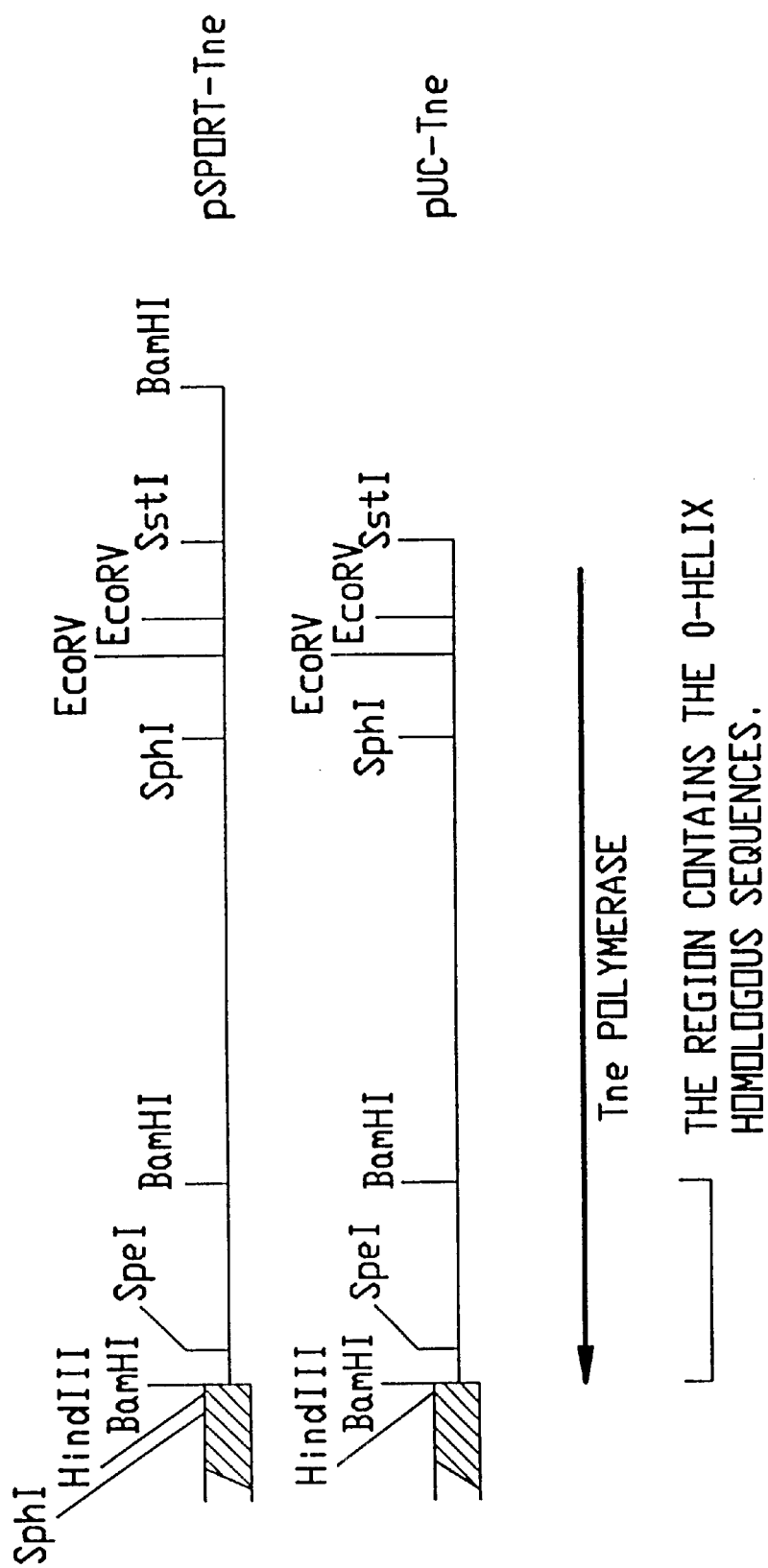
FIG. 4 shows the restriction map of the approximate DNA fragment which contains the Tne DNA polymerase gene in pSport 1 and pUC19. This figure also shows the region containing the O-helix homologous sequences.

Since the pCP13-32 clone expressing the Tne DNA polymerase gene contains about 25 kb of *T. neapolitana* DNA, subcloning a smaller fragment of the Tne polymerase gene was attempted. The molecular weight of the Tne DNA polymerase purified from *E. coli*/pCP13-32 was about 100 kd. Therefore, a 2.5–3.0 kb DNA fragment will be sufficient to code for full-length polymerase. A second round of Sau3A partial digestion similar to Example 3 was done using pCP13-32 DNA. In this case, a 3.5 kb region was cut out from the agarose gel, purified by Gene Clean (BIO 101, La Jolla, Calif.) and ligated into plasmid pSport 1 (Life Technologies, Inc.) which had been linearized with BamHI and dephosphorylated with calf intestinal alkaline phosphatase. After ligation, DH10B was transformed and colonies were tested for DNA polymerase activity as described in Example 4. Several clones were identified that expressed Tne DNA polymerase. One of the clones (pSport-Tne) containing about 3 kb insert was further characterized. A restriction map of the DNA fragment is shown in FIG. 4. Further, a 2.7 Kb HindIII-SstI fragment was subcloned into pUC19 to generate pUC19-Tne. *E. coli*/pUC19-Tne also produced Tne DNA polymerase.

The Tne polymerase clone was sequenced by methods known in the art. The nucleotide sequence obtained of the 5' end prior to the start ATG is shown in SEQ ID NO:1. The nucleotide sequence obtained which encodes carboxy-terminal region of the Tne polymerase is shown in FIGS. 5A and 5B (SEQ ID NO:17). When SEQ ID NO:17 is translated it does not produce the entire amino acid sequence of the Tne polymerase due to frame shift errors generated during the determination of the nucleotide sequence. However, an amino acid sequence of the Tne polymerase was obtained by translating all three reading frames of SEQ ID NO:17, comparing these sequences with known polymerase amino acid sequences, and splicing the Tne polymerase sequence together to form the amino acid sequence set forth in SEQ ID NO:18. The complete nucleotide sequence coding for Tne is shown in SEQ ID NO:2 and the complete amino acid sequence is shown in SEQ ID NO:3.

SEQ ID NO:3 shows that the Tne sequence has an N-terminal methionine. It is not known with certainty whether the wild type Tne protein comprises an N-terminal methionine. It is possible to remove this N-terminal methionine according to methods well known to those of ordinary skill in the art, e.g. with a methionine amino peptidase.

EXAMPLE 6
Purification of *Thermotoga neapolitana* DNA Polymerase from *E. coli*

Twelve grams of *E. coli* cells expressing cloned Tne DNA polymerase (DH10B/pSport-Tne) were lysed by sonication (four thirty-second bursts with a medium tip at the setting of nine with a Heat Systems Ultrasonics Inc., model 375 sonicator) in 20 ml of ice cold extraction buffer (50 mM Tris HCl (pH 7.4), 8% glycerol, 5 mM mercaptoethanol, 10 mM NaCl, 1 mM EDTA, 0.5 mM PMSF). The sonicated extract was heated at 80° C. for 15 min. and then cooled in ice for 5 min. 50 mM KCl and PEI (0.4%) was added to remove nucleic acids. The extract was centrifuged for clarification. Ammonium sulfate was added to 60%, the pellet was collected by centrifugation and resuspended in 10 ml of column buffer (25 mM Tris-HCl (pH 7.4), 8% glycerol, 0.5% EDTA, 5 mM 2-mercaptoethanol, 10 mM KCl). A Blue-Sepharose (Pharmacia) column, or preferably a Toso heparin (Tosohaas) column, was washed with 7 column volumes of column buffer and eluted with a 15 column volume gradient of buffer from 10 mM to 2 M KCl. Fractions containing polymerase activity were pooled. The fractions were dialyzed against 20 volumes of column buffer. The pooled fractions were applied to a Toso650Q column (Tosohaas). The column was washed to baseline $OD_{280}$ and elution effected with a linear 10 column volume gradient of 25 mM Tris (pH 7.4), 8% glycerol, 0.5 mM EDTA, 10 mM KCl, 5 mM β-mercaptoethanol to the same buffer plus 650 mM KCl. Active fractions were pooled.

EXAMPLE 7
Characterization of Purified Tne DNA Polymerase
1. Determination of the Molecular Weight of *Thermotoga neapolitana* DNA Polymerase The molecular weight of 100 kilodaltons was determined by electrophoresis in a 12.5% SDS gel by the method of Laemmli, U.K., *Nature* (Lond.) 227:680–685 (1970). Proteins were detected by staining with Coomassie brilliant blue. A 10 kd protein ladder (Life Technologies, Inc.) was used as a standard.

2. Method for Measuring Incorporation of [$\alpha^{35}$S]-dATP Relative to $^3$H-dATP Incorporation of [αS]dATP was evaluated in a final volume of 500 μl of reaction mix, which was preincubated at 72° C. for five minutes, containing either a [$^3$H]TTP nucleotide cocktail (100 μM each TTP, dATP, dCTP, dGTP with [$^3$H]TTP at 90.3 cpm/pmol), a nucleotide cocktail containing [αS]dATP as the only source of dATP (100 μM each [αS]dATP, dCTP, dGTP, TTP with [$\alpha^{35}$S]dATP at 235 cpm/pmol), or a mixed cocktail (50 μM [αS]dATP, 50 μM dATP, 100 μM TTP, 100 μM dCTP, 100 μM dGTP with [$^{35}$αS] dATP at 118 cpm/pmol and [$^3$H]TTP at 45.2 cpm/pmol) and 50 mM bicine, pH 8.5, 30 mM $MgCl_2$, 0.25 mg/ml activated salmon sperm DNA, 20% glycerol. The reaction was initiated by the addition of 0.3 units of *T. neapolitana* DNA polymerase or *T. aquaticus* DNA polymerase. At the times indicated a 25 μl aliquot was removed and quenched by addition of ice cold EDTA to a final concentration of 83 mM. 20 μl aliquots of the quenched reaction samples were spotted onto GF/C filters. Rates of incorporation were compared and expressed as a ratio of *T. neapolitana* to *T. aquaticus*. The incorporation of [$\alpha^{35}$S] dATP by *T. neapolitana* DNA polymerase was three-fold higher than that of *T. aquaticus* DNA polymerase.

EXAMPLE 8
Reverse Transcriptase Activity $(A)_n{:}(dT)_{12-18}$ is the synthetic template primer used most frequently to assay for reverse transcriptase activity of DNA polymerases. It is not specific for retroviral-like reverse transcriptase, however, being copied by many prokaryotic and eukaryotic DNA polymerases (Modak and Marcus, *J. Biol. Chem.* 252:11–19 (1977); Gerard et al., *Biochem.* 13:1632–1641 (1974); Spadari and Weissbach, *J. Biol. Chem.* 249:5809–5815 (1974)). $(A)_n{:}(dT)_{12-18}$ is copied particularly well by cellular, replicative DNA polymerases in the presence of $Mn^{++}$, and much less efficiently in the presence of $Mg^{++}$ (Modak and Marcus, *J. Biol. Chem.* 252:11–19 (1977); Gerard et al., *Biochem.* 13:1632–1641 (1974); Spadari and Weissbach, *J. Biol. Chem.* 249:5809–5815 (1974)). In contrast, most cellular, replicative DNA polymerases do not copy the synthetic template primer $(C)_n{:}(dG)_{12-18}$ efficiently in presence of either $Mn^{++}$ or $Mg^{++}$, but retroviral reverse transcriptases do. Therefore, in testing for the reverse transcriptase activity of a DNA polymerase with synthetic template primers, the stringency of the test increases in the following manner from least to most stringent: $(A)_n{:}(dT)_{12-18}$ ($Mn^{++}$)<$(A)_n{:}(dT)_{12-18}$ ($Mg^{++}$) <<$(C)_n{:}(dG)_{12-18}$ ($Mn^{++}$)<$(C)_n{:}(dG)_{12-18}$ ($Mg^{++}$).

The reverse transcriptase activity of Tne DNA polymerase was compared with *Thermus thermophilus* (Tth) DNA polymerase utilizing both $(A)_n{:}(dT)_{20}$ and $(C)_n{:}(dG)_{12-18}$. Reaction mixtures (50 μl) with $(A)_n{:}(dT)_{20}$ contained 50 mM Tris-HCl (pH 8.4), 100 μM $(A)_n$, 100 μM $(dT)_{20}$, and either 40 mM KCl, 6 mM $MgCl_2$, 10 mM dithiothreitol, and 500 μM [$^3$H]dTTP (85 cpm/pmole), or 100 mM KCl, 1 mM $MnCl_2$, and 200 μM [$^3$H]dTTP (92 cpm/pmole). Reaction mixtures (50 μl) with $(C)_n{:}(dG)_{12-18}$ contained 50 mM Tris-HCl (pH 8.4), 60 μM $(C)_n$, 24 μM $(dG)_{12-18}$, and either 50 mM KCl, 10 mM $MgCl_2$, 10 mM dithiothreitol, and 100 μM [$^3$H]dGTP (132 cpm/pmole), or 100 mM KCl, 0.5 mM $MnCl_2$, and 200 μM [$^3$H]dGTP (107 cpm/pmole). Reaction mixtures also contained either 2.5 units of the Tth DNA polymerase (Perkin-Elmer) or 2.5 units of the Tne DNA polymerase. Incubations were at 45° C. for 10 min followed by 75° C. for 20 min.

The table shows the results of determining the relative levels of incorporation of Tne and Tth DNA polymerase with $(A)_n{:}(dT)_{20}$ and $(C)_n{:}(dG)_{12-18}$ in the presence of $Mg^{++}$ and $Mn^{++}$. Tne DNA polymerase appears to be a better reverse transcriptase than Tth DNA polymerase under reaction conditions more specific for reverse transcriptase, i.e., in the presence of $(A)_n{:}(dT)_{20}$ with $Mg^{++}$ and $(C)_n{:}(dG)_{12-18}$ with $Mn^{++}$ or $Mg^{++}$.

DNA Polymerase Activity of Tth and Tne
DNA Polymerase with $(A)_n:(dT)_{20}$ and $(C)_n:(dG)_{12-18}$

| Enzyme | DNA Polymerase Activity (pMoles Complementary [$^3$H]dNTP Incorporated) | | | |
|---|---|---|---|---|
| | $(A)_n:(dT)_{20}$ | | $(C)_n:(dG)$ | |
| | $Mg^{++}$ | $Mn^{++}$ | $Mg^{++}$ | $Mn^{++}$ |
| Tne | 161.8 | 188.7 | 0.6 | 4.2 |
| Tth | 44.8 | 541.8 | 0 | 0.9 |

EXAMPLE 9
Construction of *Thermotoga Neapolitana* 3'-to-5' Exonuclease Mutant The amino acid sequence of portions of the Tne DNA polymerase was compared with other known DNA polymerases such as *E. coli* DNA polymerase 1, Taq DNA polymerase, T5 DNA polymerase, and T7 DNA polymerase to localize the regions of 3'-to-5' exonuclease activity, and the dNTP binding domains within the DNA polymerase. One of the 3'-to-5' exonuclease domains was determined based on the comparison of the amino acid sequences of various DNA polymerases (Blanco, L., et al. *Gene* 112: 139–144 (1992); Braithwaite and Ito, *Nucleic Acids Res.* 21: 787–802 (1993)) is as follows:

| Tne | 318 | PSFALD*LETSS | 328 | (SEQ ID NO: 4) |
|---|---|---|---|---|
| Pol I | 350 | PVFAFDTETDS | 360 | (SEQ ID NO:5; Braithwaite and Ito, supra) |
| T5 | 133 | GPVAFDSETSA | 143 | (SEQ ID NO:6; Braithwaite and Ito, supra) |
| T7 | 1 | MIVSDIEANA | 10 | (SEQ ID NO:7; Braithwaite and Ito, supra). |

As a first step to make the Tne DNA polymerase devoid of 3'-5' exonuclease activity, a 2 kb Sph fragment from pSport-Tne was cloned into M13mp19 (LTI, Gaithersburg, Md.). The recombinant clone was selected in *E. coli* DH5αF'IQ (LTI, Gaithersburg, Md.). One of the clones with the proper insert was used to isolate uracilated single-stranded DNA by infecting *E. coli* CJ236 (Biorad, Calif.) with the phage particle obtained from *E. coli* DH5αF'IQ. An oligonucleotide, GA CGT TTC AAG CGC TAG GGC AAA AGA (SEQ ID NO:8) was used to perform site directed mutagenesis. This site-directed mutagenesis converted $Asp^{323}$ (indicated as * above) to $Ala^{323}$. An Eco47III restriction site was created as part of this mutagenesis to facilitate screening of the mutant following mutagenesis. The mutagenesis was performed using a protocol as described in the Biorad manual (1987) except T7 DNA polymerase was used instead of T4 DNA polymerase (USB, Cleveland, Ohio). The mutant clones were screened for the Eco47III restriction site that was created in the mutagenic oligonucleotide. One of the mutants having the created Eco47III restriction site was used for further study. The mutation $Asp^{323}$ to $Ala^{323}$ has been confirmed by DNA sequencing.

Figure 6A:
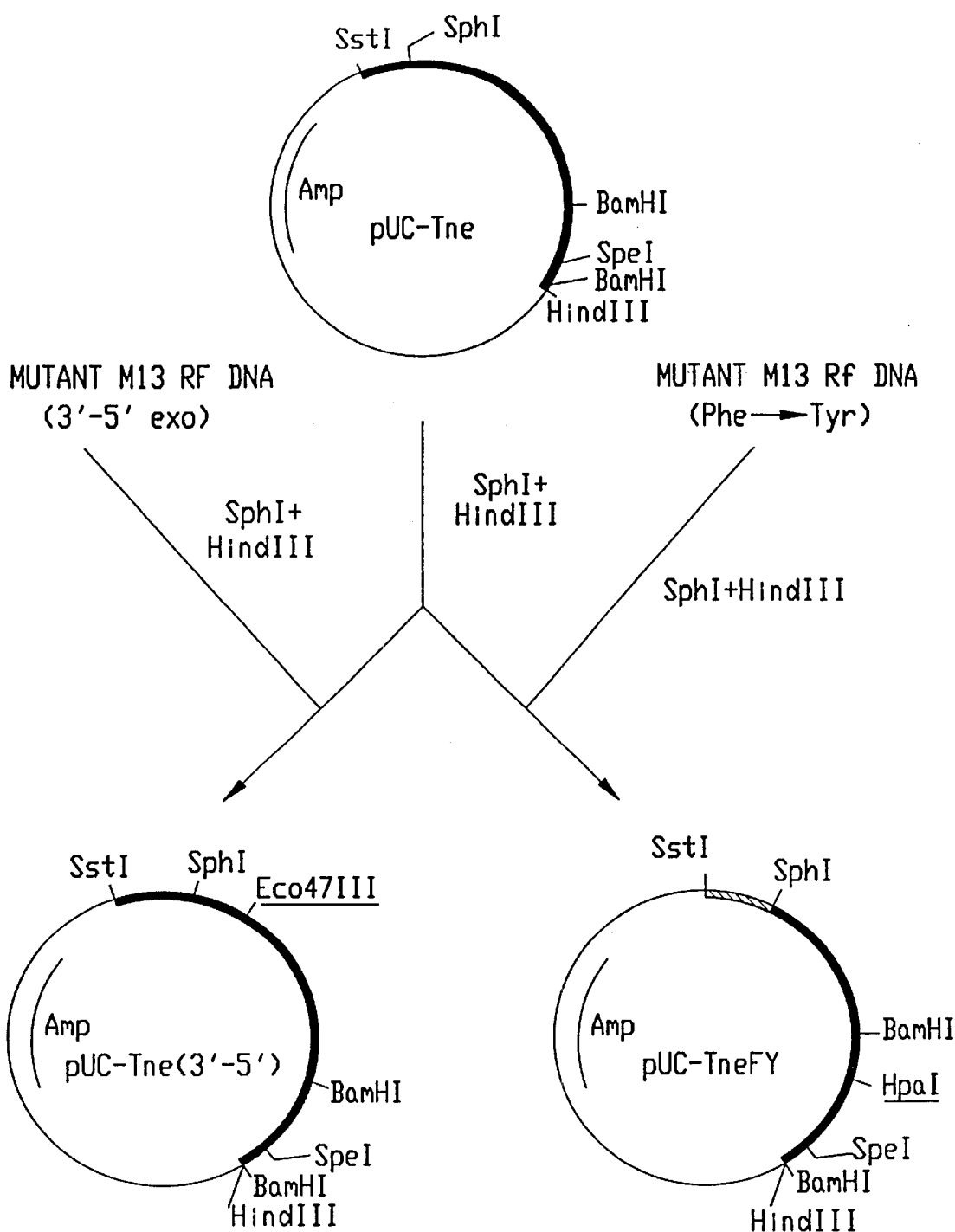
FIG. 6A schematically depicts the construction of plasmids pUC-Tne (3'→5') and pUC-Tne FY.

To incorporate the 3'-to-5' exonuclease mutation in an expression vector, the mutant phage was digested with SphI and HindIII. A 2 kb fragment containing the mutation was isolated. This fragment was cloned in pUC-Tne to replace the wild type fragment. See FIG. 6A. The desired clone, pUC-Tne (3'→5'), was isolated. The presence of the mutant sequence was confirmed by the presence of the unique Eco47III site. The plasmid was then digested with SstI and HindIII. The entire mutant polymerase gene (2.6 kb) was purified and cloned into SstI and HindIII digested pTrc99 expression vector (Pharmacia, Sweden). The clones were selected in DH10B (LTI, Gaithersburg, Md.). The resulting plasmid was designated pTrcTne35. See FIG. 6B. This clone produced active heat stable DNA polymerase.

EXAMPLE 10
Phenylalanine to Tyrosine Mutant

As discussed supra, the polymerase active site including the dNTP binding domain is usually present at the carboxyl terminal region of the polymerase. The sequence of the Tne polymerase gene suggests that the amino acids that presumably contact and interact with the dNTPs are present within the 694 bases starting at the internal BamHI site. See FIG. 4 and FIGS. 5A and 5B. This conclusion is based on homology with a prototype polymerase *E. coli* DNA polymerase 1. See Polisky et al., *J. Biol. Chem.* 265:14579–14591 (1990). The sequence of the carboxyl terminal portion of the polymerase gene is shown in FIGS. 5A and 5B. Based upon this sequence, it is possible to compare the amino acid sequence within the O-helix for various polymerases. The complete sequence of the DNA polymerase is shown in SEQ ID NO:3. The corresponding O-helix region band on the sequence in FIGS. 5A and 5B includes amino acids 59 to 72.

| Tne | 722 | RRVGKMVNFSIIYG | 735 | (SEQ ID NO:9) |
|---|---|---|---|---|
| Pol I | 754 | RRSAKAINFGLIYG | 767 | (SEQ ID NO:10) |
| T5 | 562 | RQAAKAITFGILYG | 575 | (SEQ ID NO:11) |
| T7 | 518 | RDNAKTFIYGFLYG | 531 | (SEQ ID NO:12) |
| Taq | 659 | RRAAKTINFGVLYG | 672 | (SEQ ID NO:13) |

It was shown that by replacing the phenylalanine residue of Taq DNA polymerase, the polymerase becomes non-discriminating against non-natural nucleotides such as dideoxynucleotides. See application Ser. No. 08/525,087 entitled "Mutant DNA Polymerases and Use Thereof" of Deb K. Chatterjee, filed Sep. 8, 1995, specifically incorporated herein by reference. The mutation was based on the assumption that T7 DNA polymerase contains a tyrosine residue in place of the phenylalanine, and T7 DNA polymerase is non-discriminating against dideoxynucleotides. The corresponding residue, $Phe^{762}$ of *E. coli* PolI is an amino acid that directly interacts with nucleotides. (Joyce and Steitz, *Ann. Rev. Biochem.* 63:777–822 (1994); Astake, M. J., *J. Biol. Chem.* 270:1945–1954 (1995)). A similar mutant of Tne DNA polymerase was prepared.

In order to change $Phe^{730}$ of the Tne polymerase to a $Tyr^{730}$ as numbered in SEQ ID NO:3, site directed mutagenesis was performed using the oligonucleotide GTA TAT TAT AGA GTA GTT AAC CAT CTT TCC A. (SEQ ID NO:14). As part of this oligonucleotide directed mutagenesis, a HpaI restriction site was created in order to screen mutants easily. The same uracilated single-stranded DNA and mutagenesis procedure described in Example 9 were used for this mutagenesis. Following mutagenesis, the mutants were screened for the HpaI site. Mutants with the desired HpaI site were used for further study. The mutation has been confirmed by DNA sequencing.

Figure 6B:
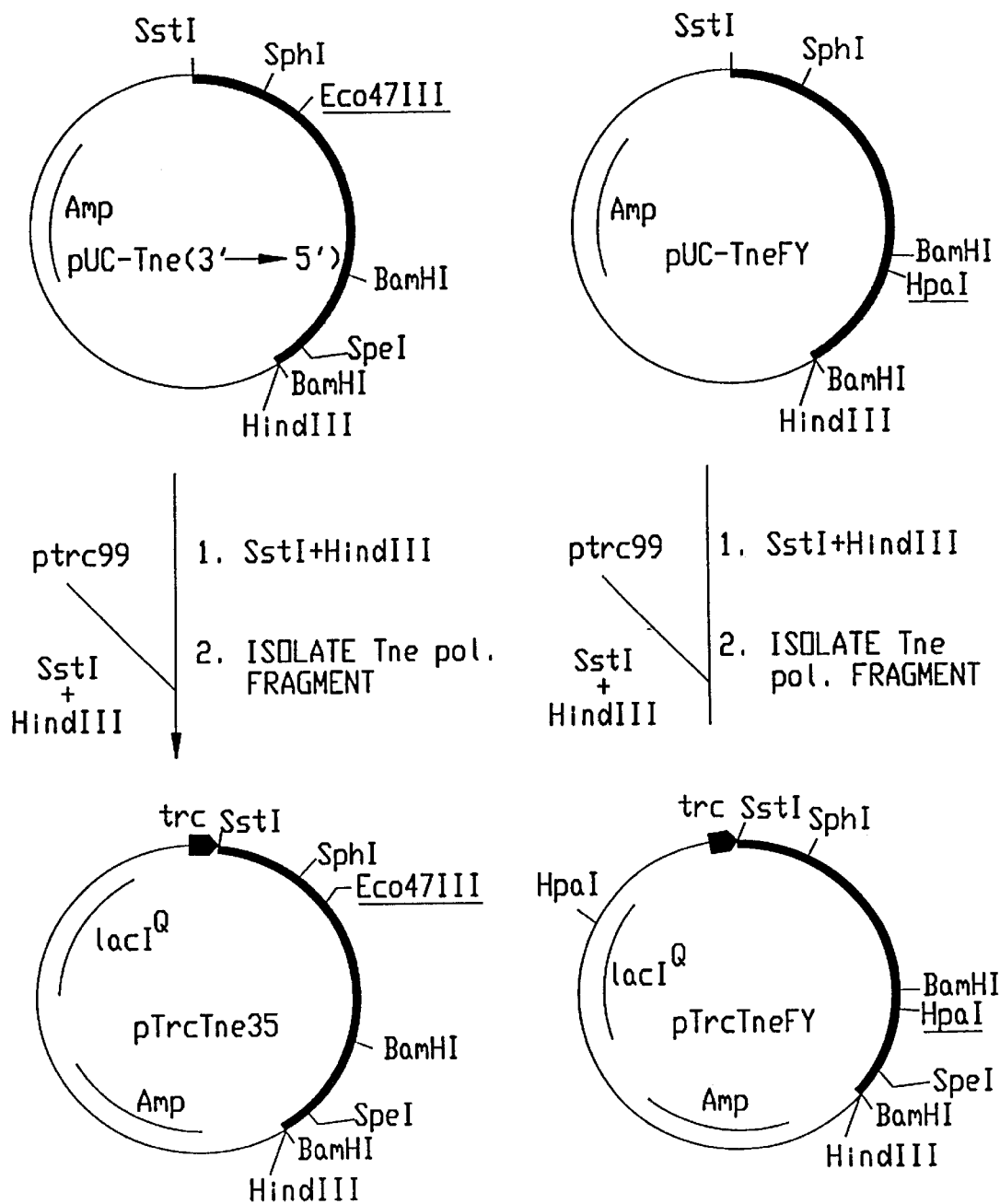
FIG. 6B schematically depicts the construction of plasmids pTrc Tne35 and pTrcTne FY.

The $Phe^{730}$ to $Tyr^{730}$ mutation was incorporated into pUC-Tne by replacing the wild type SphI-HindIII fragment with the mutant fragment obtained from the mutant phage DNA. The presence of the desired clone, pUC-TneFY, was confirmed by the presence of the unique HpaI site, see FIG. 6A. The entire mutant polymerase gene was subcloned into pTrc99 as an SstI-HindIII fragment as described above in DH10B. The resulting plasmid was designated pTrcTneFY. (FIG. 6B). The clone produced active heat stable polymerase.

EXAMPLE 11
3'-to-5' Exonuclease and Phe$^{730}$→Tyr$^{730}$ Double Mutants

Figure 7:
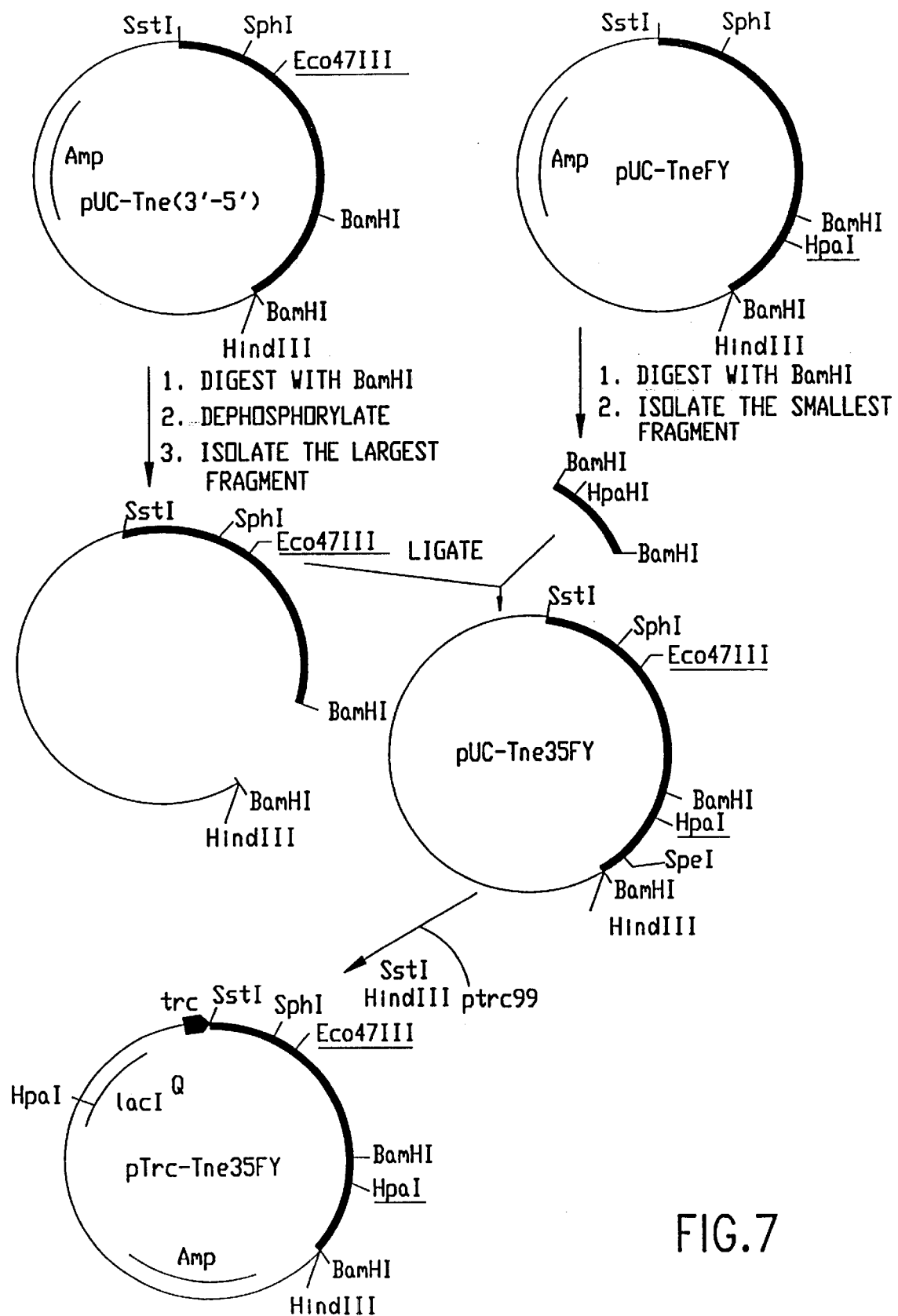
FIG. 7 schematically depicts the construction of plasmid pTrcTne35 FY.

In order to introduce the 3'→5' exonuclease mutation and the Phe$^{730}$→Tyr$^{730}$ mutation in the same expression vector, pTrc99, it was necessary to first reconstitute both mutations in the pUC-Tne clone. See FIG. 7. Both the pUC-Tne (3'→5') and the pUC-TneFY were digested with BamHI. The digested pUC-Tne (3'→5') was dephosphorylated to avoid recirculation in the following ligations. The resulting fragments were purified on a 1% agarose gel. The largest BamHI fragment (4.4 kb) was purified from pUC-Tne (3'→5') digested DNA and the smallest BamHI fragment (0.8 kb) containing the Phe$^{730}$→Tyr$^{730}$ mutation was purified and ligated to generate pUC-Tne35FY. The proper orientation and the presence of both mutations in the same plasmid was confirmed by Eco47III, HpaI, and SphI-HindIII restriction digests. See FIG. 7.

The entire polymerase containing both mutations was subcloned as a SstI-HindIII fragment in pTrc99 to generate pTrcTne35FY in DH10B. The clone produced active heat stable polymerase.

EXAMPLE 12
3'-to-5' Exonuclease, 5'-to-3' Exonuclease, and Phe$^{730}$→Tyr$^{730}$ Triple Mutants In most of the known polymerases, the 5'-to-3' exonuclease activity is present at the amino terminal region of the polymerase (Ollis, D. L., et al., *Nature* 313, 762–766, 1985; Freemont, P. S., et al., *Proteins* 1, 66–73, 1986; Joyce, C. M., *Curr. Opin. Struct. Biol.* 1: 123–129 (1991). There are some conserved amino acids that are implicated to be responsible for 5'-to-3' exonuclease activity (Gutman and Minton, *Nucl. Acids Res.* 21, 4406–4407, 1993). See supra. It is known that 5'-to-3' exonuclease domain is dispensable. The best known example is the Klenow fragment of *E. coli* Pol I. The Klenow fragment is a natural proteolytic fragment devoid of 5'-to-3' exonuclease activity (Joyce, C. M., et al., *J. Biol. Chem.* 257, 1958–1964, 1990). In order to generate an equivalent mutant for Tne DNA polymerase devoid of 5'-to-3' exonuclease activity, the presence of a unique SphI site present 680 bases from the SstI site was exploited. pUC-Tne35FY was digested with HindIII, filled-in with Klenow fragment to generate a blunt-end, and digested with SphI. The 1.9 kb fragment was cloned into an expression vector pTTQ19 (Stark, M. J. R., *Gene* 51, 255–267, 1987) at the SphI-SmaI sites and was introduced into DH10B. This cloning strategy generated an in-frame polymerase clone with an initiation codon for methionine from the vector. The resulting clone is devoid of 219 amino terminal amino acids of Tne DNA polymerase. This clone is designated as pTTQTne535FY. The clone produced active heat stable polymerase. No exonuclease activity could be detected in the mutant polymerase as evidenced by lack of presence of unusual sequence ladders in the sequencing reaction. This particular mutant polymerase is highly suitable for DNA sequencing.

EXAMPLE 13
5'-to-3' Exonuclease Deletion and Phe$^{730}$→Tyr$^{730}$ Substitution Mutant In order to generate the 5'→3' exonuclease deletion mutant of the Tne DNA polymerase Phe$^{730}$Tyr$^{730}$ mutant, the 1.8 kb SphI-SpeI fragment of pTTQTne535FY was replaced with the identical fragment of pUC-Tne FY. See FIG. 8. A resulting clone, pTTQTne5FY, produced active heat stable DNA polymerase. As measured by the rate of degradation of a labeled primer, this mutant has a modulated, low but detectable, 3'→5' exonuclease activity compared to wild type Tne DNA polymerase. M13/pUC Forward 23-Base Sequencing Primer™, obtainable from LTI, Gaithersburg, Md., was labeled at the 5' end with [P$^{32}$] ATP and T4 kinase, also obtainable from LTI, Gaithersburg, Md., as described by the manufacturer. The reaction mixtures contained 20 units of either wild-type or mutant Tne DNA polymerase, 0.25 pmol of labeled primer, 20 mM tricine, pH 8.7, 85 mM potassium acetate, 1.2 mM magnesium acetate, and 8% glycerol. Incubation was carried out at 70° C. At various time points, 10 μl aliquots were removed to 5 μl cycle sequencing stop solution and were resolved in a 6% polyacrylamide sequencing gel followed by andoradiography. While the wild-type polymerase degraded the primer in 5 to 15 minutes, it took the mutant polymerase more than 60 minutes for the same amount of degradation of the primer. Preliminary results suggest that this mutant polymerase is able to amplify more than 12 kb of genomic DNA when used in conjunction with Taq DNA polymerase. Thus, the mutant polymerase is suitable for large fragment PCR.

EXAMPLE 14
Purification of the Mutant Polymerases

The purification of the mutant polymerases was done essentially as described in U.S. patent application Ser. No. 08/370,190, filed Jan. 9, 1995, entitled "Cloned DNA Polymerases for *Thermotoga neapolitana,*" and as in Example 6, supra, with minor modifications. Specificaly, 5 to 10 grams of cells expressing cloned mutant Tne DNA polymerase were lysed by sonication with a Heat Systems Ultrasonic, Inc. Model 375 machine in a sonication buffer comprising 50 mM Tris-HCl (pH 7.4); 8% glycerol; 5 mM 2-mercaptoethanol, 10 mM NaCl, 1 mM EDTA, and 0.5 mM PMSF. The sonication sample was heated at 75° C. for 15 minutes. Following heat treatment, 200 mM NaCl and 0.4% PEI was added to remove nucleic acids. The extract was centrifuged for clarification. Ammonium sulfate was added to 48%, the pellet was resuspended in a column buffer consisting of 25 mM Tris-HCl (pH 7.4); 8% glycerol; 0.5% EDTA; 5 mM 2-mercaptoethanol; 10 mM KCl and loaded on a heparin agarose (LTI) column. The column was washed with 10 column volumes using the loading buffer and eluted with a 10 column volume buffer gradient from 10 mM to 1 M KCl. Fractions containing polymerase activity were pooled and dialyzed in column buffer as above with the pH adjusted to 7.8. The dialyzed pool of fractions were loaded onto a MonoQ (Pharmacia) column. The column was washed and eluted as described above for the heparin column. The active fractions are pooled and a unit assay was performed.

The unit assay reaction mixture contained 25 mM TAPS (pH 9.3), 2 mM MgCl$_2$, 50 mM KCl, 1 mM DTT, 0.2 mM dNTPs, 500 μg/ml DNAse I treated salmon sperm DNA, 21 mCi/ml [αP$^{32}$] dCTP and various amounts of polymerase in a final volume of 50 μl. After 10 minutes incubation at 70° C., 10 μl of 0.5 M EDTA was added to the tube. TCA precipitable counts were measured in GF/C filters using 40 μl of the reaction mixture.

EXAMPLE 15
DNA Sequencing with the Mutant Polymerases

M13/pUC 23-base forward sequencing primer was $^{32}$P-end-labeled for use in sequencing by incubating the following mixture at 37° C. for 10 minutes: 60 mM Tris-HCl (pH 7.8), 10 mM MgCl$_2$, 200 mM KCl, 0.2 μM primer, 0.4 μM (2 μCi/μl) [γ-$^{32}$P]ATP, 0.2 U/μl T4 polynucleotide kinase. Labeling was terminated by incubating at 55° C. for 5 minutes.

Four 10 μl base-specific sequencing reactions were set up for each test. The polymerase and the ddNTP concentrations were varied as follows:

| Test | Tne DNA polymerase | [ddATP] | [ddCTP] | [ddGTP] | [ddTTP] |
|---|---|---|---|---|---|
| 1 | wild-type | 0.4 mM | 0.2 mM | 0.04 mM | 0.4 mM |
| 2 | TneFY | 0.4 mM | 0.2 mM | 0.04 mM | 0.4 mM |
| 3 | TneFY | 0.04 mM | 0.02 mM | 0.004 mM | 0.04 mM |
| 4 | TneFY | 0.004 mM | 0.002 mM | 0.0004 mM | 0.004 mM |
| 5 | Tne35FY | 0.4 mM | 0.2 mM | 0.04 mM | 0.4 mM |
| 6 | Tne35FY | 0.04 mM | 0.02 mM | 0.004 mM | 0.04 mM |
| 7 | Tne35FY | 0.004 mM | 0.002 mM | 0.0004 mM | 0.004 mM |
| 8 | Tne535FY | 0.4 mM | 0.2 mM | 0.04 mM | 0.4 mM |
| 9 | Tne535FY | 0.04 mM | 0.02 mM | 0.004 mM | 0.04 mM |
| 10 | Tne535FY | 0.004 mM | 0.002 mM | 0.0004 mM | 0.004 mM |

Other components of the reaction were held constant: 1.1 nM pUC 18 DNA, 22 nM $^{32}$P-end-labeled primer, 30 mM Tris-HCl (pH 9.0), 5 mM MgCl$_2$, 50 mM KCl, 0.05% (w/v) W-1, 0.056 U/μl DNA polymerase (see table), 20 μM dATP, 20 μM dCTP, 20 μM 7-deaza-dGTP, 20 μM dTTP. Samples were incubated in a thermal cycler at 95° C. for 3 minutes, followed by 20 cycles of (30 seconds at 95° C., 30 seconds at 55° C., 60 seconds at 70° C.) and 10 cycles of (30 seconds at 95° C., 60 seconds at 70° C.). Reactions were terminated with 5 μl of stop solution (95% (v/v) formamide, 10 mM EDTA (pH 8.0), 0.1% (w/v) bromophenol blue, 0.1% (w/v) xylene cyanol and denatured for two minutes at 70° C. Three μl aliquots were separated on a 6% TBE/urea sequencing gel. The dried gel was exposed to BioMAX-MR x-ray film for 16 hours.

Results

Cycle sequencing reactions using P$^{32}$ end-labeled primers were prepared using wild-type Tne DNA polymerase and each of the three mutants, TneFY, Tne35FY, and Tne535FY. All four of the polymerases produced sequencing ladders. The TneFY mutant gave only a 9 base sequencing ladder when the Taq cycle sequencing reaction conditions were used. This is suggestive of premature termination due to efficient ddNTP incorporation. Diluting the dideoxynucleotides by a factor of 100 extended the ladder to about 200 bases. The F→Y mutation in the TneFY polymerase therefore allowed dideoxynucleotides to be incorporated at a much higher frequency than for wild-type polymerase. The Tne35FY mutant demonstrated a similar ability to incorporate dideoxynucleotides. In this case, the sequence extended to beyond 400 bases and the excess P$^{32}$ end-labeled M13/pUC forward 23-Base sequencing primer band remained at the 23-base position in the ladder. The persistence of the 23-base primer band confirmed that the 3'→5' exonuclease activity had been significantly reduced. The Tne535FY mutant performed similarly to the Tne35FY mutant except that the signal intensity increased by at least fivefold. The background was very low and relative band intensities were extremely even, showing no patterns of sequence-dependent intensity variation.

EXAMPLE 16

Generation of 5'→3' Exonuclease Mutant of Full Length Tne DNA Polymerase

1. Identification of Two Amino Acids Responsible for 5'-3' Exonuclease Activity

Tne DNA polymerase contains three enzymatic activities similar to E. coli DNA polymerase I: 5'-3' DNA polymerase activity, 3'-5' exonuclease activity and 5'-3' exonuclease activity. This example is directed to the elimination of the 5'-3' exonuclease activity in full length Tne DNA polymerase. Gutman and Minton (Nucleic Acids Res. 1993, 21, 4406–4407) identified six (A–F) conserved 5'-3' exonuclease domains containing a total of 10 carboxylates in various DNA polymerases in the polI family. Seven out of 10 carboxylates (in domains A, D and E) have been implicated to be involved in divalent metal ions binding as judged from the crystal structure (Kim et al. Nature, 1995, 376, 612–616) of Taq DNA polymerase. However, there was no clear demonstration that these carboxylates are actually involved 5'-3' exonuclease activity. In order to find out the biochemical characteristics of some of these carboxylates, two of the aspartic acids in domains A and E were chosen for mutagenesis. The following aspartic acids in these two domains were identified:

Tne DNA polymerase: 5 F L F D$^8$ G T 10 (domain A)
Taq DNA polymerase: 15 L L V D$^{18}$ G H 20
and
Tne DNA polymerase: 132 S L I T G D$^{137}$ K D M L 141 (domain E)
Taq DNA polymerase: 137 R I L T A D$^{142}$ K D L Y 146

2. Isolation of Single Stranded DNA for Mutagenesis

Single stranded DNA was isolated from pSportTne (see infra). pSportTne was introduced into DH5αF'IQ (LTI, Gaithersburg, Md.) by transformation. A single colony was grown in 2 ml Circle Grow (Bio 101, CA) medium with ampicillin at 37° C. for 16 hrs. A 10 ml fresh media was inoculated with 0.1 ml of the culture and grown at 37° C. until the A590 reached approximately 0.5. At that time, 0.1 ml of M13KO7 helper phage (1×10$^{11}$ pfu/ml, LTI) was added to the culture. The infected culture was grown for 75 min. Kanamycin was then added at 50 μg/ml, and the culture was grown overnight (16 hrs.). The culture was spun down. 9 ml of the supernatant was treated with 50 μg each of RNaseA and DNaseI in the presence of 10 mM MgCl$_2$ for 30 min. at room temperature. To this mixture, 0.25 volume of a cocktail of 3M ammonium acetate plus 20% polyethylene glycol was added and incubated for 20 min. on ice to precipitate phage. The phage was recovered by centrifugation. The phage pellet was dissolved in 200 μl of TE (10 mM Tris-HCl (pH 8) and 1 mM EDTA). The phage solution was extracted twice with equal volume of buffer saturated phenol (LTI, Gaithersburg, Md.), twice with equal volume of phenol:chloroform:isoamyl alcohol mixture (25:24:1, LTI, Gaithersburg, Md.) and finally, twice with chloroform:isoamyl alcohol (24:1). To the aqueous layer, 0.1 volume of 7.5 M ammonium acetate and 2.5 volume of ethanol were added and incubated for 15 min. at room temperature to precipitate single stranded DNA. The DNA was recovered by centrifugation and suspended in 200 μl TE.

3. Mutagenesis of D$^8$ and D$^{137}$

Two oligos were designed to mutagenize D$^8$ and D$^{137}$ to alanine. The oligos are: 5' GTAGGCCAGGGCTGT GCCGGCAAAGAGAAATAGTC 3' (SEQ ID NO:15) (D8A) and 5' G A A G C A T A T C C T T GGCGCCGGTTATTATGAAAATC 3' (SEQ ID NO:16) (D137A). In the D8A oligo a NgoAIV (bold underlined) and in the oligo D137A a KasI (bold underlined) site was created for easy identification of clones following mutagenesis. 200 pmol of each oligo was kinased according to the Muta-gene protocol (Bio-Rad, CA) using 5 units of T4 Kinase (LTI, Gaithersburg, Md.). 200 ng of single stranded DNA was annealed with 2 pmol of oligo according to the Muta-gene protocol. The reaction volume was 10 µl. Following the annealing step, complementary DNA synthesis and ligation was carried out using 5 units of wild-type T7 DNA polymerase (USB, Ohio) and 0.5 unit T4 ligase (LTI). 1 µl of the reaction was used to transform a MutS E. coli (obtainable from Dr. Paul Modrich at the Duke University, NC) and selected in agar plates containing ampicillin. A control annealing and synthesis reaction was carried out without addition of any oligo to determine the background. There were 50–60 fold more colonies in the transfomation plates with the oligos than without any oligo. Six colonies from each mutagenic oligo directed synthesis were grown and checked for respective restriction site (NgoAIV or KasI). For D8A (NgoAIV), 4 out of 6 generated two fragments (3 kb and 4.1 kb). Since pSportTne has an NgoAIV site near the f1 intergenic region, the new NgoAIV site within the Tne DNA polymerase produced the expected fragments. The plasmid was designated as pSportTneNgoAIV. For D137A (KasI), 5 out of 6 clones produced two expected fragments of 1.1 kb and 6 kb in size. Since pSportTne has another KasI site, the newly created KasI site generated these two expected fragments. The plasmid was designated as pSportTneKasI. Both D8A and D137A mutations have been confirmed by DNA sequencing.

4. Reconstruction of the Mutant Polymerase into Expression Vector

During the course of expression of Tne DNA polymerase or mutant Tne DNA polymerase, a variety of clones were constructed. One such clone was designated as pTTQTne SeqS1. This plasmid was constructed as follows: first, similar to above mutagenesis technique glycine 195 was changed to an aspartic acid in pSportTne. A mutation in the corresponding amino acid in E. coli DNA polymerasei (polA214, domain F) was found to have lost the 5'-3' exonuclease activity (Gutman and Minton, see above). An SspI site was created in the mutant polymerase. Second, a 650 bp SstI-SphI fragment containing the G195D mutation was subcloned in pUCTne35FY (see infra) to replace the wild type fragment. This plasmid was called pUCTne3022. Finally, the entire mutant Tne DNA polymerase was subcloned from pUCTne3022 into pTTQ18 as SstI-HindIII fragment to generate pTTQTneSeqS1. To introduce the mutation D8A or D137A in this expression vector, the 650 bp SstI-SphI was replaced with the same SstI-SphI fragment from pSportTneNgoAIV or pSportTneKasI. The plasmids were designated as pTTQTneNgo(D8A) and pTTQTneKas (D137A), respectively.

5. Confirmation of the Mutations by DNA Sequencing

DNA sequencing of both mutant polymerases confirmed the presence of the restriction site NgoAIV as well as the mutation D8A; and KasI site as well as the mutation D137A. Also confirmed by DNA sequencing was the presence of the mutation D323A and the Eco47III restriction site in the 3'-5' exonuclease region. In addition, confirmed by DNA sequencing was the F730Y mutation and the HpaI restriction site in the O-helix region of the mutant Tne DNA polymerase.

6. 5'-3' Exonuclease Activity of the Mutant Tne DNA Polymerases

The full length mutant DNA polymerase was purified as described above. The 5'-3' exonuclease activity was determined as described in the LTI catalog. Briefly, 1 pmol of labeled ($^{32}$P) HaeIII digested λ DNA (LTI) was used for the assay. The buffer composition is: 25 mM Tris-HCl (pH 8.3), 5 mM MgCl$_2$, 50 mM NaCl, 0.01% gelatin. The reaction was initiated by the addition of 0, 2, 4, 6 and 10 units of either wild type or mutant Tne DNA polymerase in a 50 µl reaction. The reaction mix was incubated for 1 hr at 72° C. A 10 µl aliquot was subjected to PEI-cellulose thin layer chromatography and the label released was quantitated by liquid scintillation. In this assay, both D8A and D137A mutants showed less than 0.01% label release compared to the wild type Tne DNA polymerase. The result demonstrates that in both D8A and D137A mutants the 5'-3' exonuclease activity has been considerably diminished. Thus, it has been confirmed for the first time that these two aspartates are involved with the 5'-3' exonuclease activity.

7. DNA Sequencing Characteristics of the Mutant DNA Polymerases

Four separate base-specific reactions of the following composition were setup for each Tne polymerase mutant. 6.5 nM pUC 18, 111 nM M13/pUC 23 base forward sequencing primer, 30 mM Tris-HCl (pH 9.0), 5 mM MgCl$_2$, 10 mM NaCl, 10 mM DTT, 0.05% (w/v) W-1, 0.00185 U/µl inorganic pyrophosphatase, 0.37 µCi/µl (0.37 µM) [α-$^{35}$S] dATP, 16.7 µM α-thio-dATP, 16.7 µM dCTP, 16.7 µM 7-deaza-dGTP, 16.7 µM dTTP, and either 0.042 µM ddATP, 0.3 µM ddCTP, 0.255 µM ddGTP or 0.375 µM ddTTP. In these reactions, the concentrations of the various mutants were: 0.185 U/µl Tne535FY, or 0.170 U/µl D8A, or 0.185 U/µl D137A. Reaction volumes were 6 µl each. Sample tubes were incubated in an MJ Research DNA Engine thermal cycler at 95° C. for 3 minutes, followed by 20 cycles of (30 seconds at 95° C., 30 seconds at 55° C. and 60 seconds at 70° C.), and 10 cycles of (30 seconds at 95° C. and 60 seconds at 70° C.). Reactions were terminated with 3 µl of stop solution (95% (v/v) formamide, 10 mM EDTA (H 8.0), 0.1% (w/v) bromophenol blue, 0.1% (w/v) xylene cyanol) and denatured for two minutes at 70° C. Three µl aliquots were separated on a 6% TBE/urea sequencing gel. The dried gel was exposed to Kodak BioMAX x-ray film at room temperature approximately 18 hours.

The results of the sequencing data suggest that both D8A and D137A mutants of Tne DNA polymerase produced equivalent sequence ladders with equal band intensity in all 4 lanes comparable to another Tne DNA polymerase where the 5'-exonuclease domain was deleted (Tne535FY). This result also suggests that both D8A and D137A mutants are devoid of 5'-exonuclease activity since no false bands are seen in the sequencing ladder, a characteristic of 5'-3' exonuclease containing DNA polymerase.

EXAMPLE 17

Advantages of Tne DNA Polymerase Mutant in Sequencing Reactions

In this example, the Tne DNA polymerase of Example 12 was used which has the Phe$^{730}$→Tyr$^{730}$ mutation (making it non-discriminatory for dNTPs over ddNTPs), the Asp$^{323}$→Ala$^{323}$ mutation (which substantially reduces 3'-to-5' exonuclease activity), and the N-terminal 219 amino acid deletion mutation (which eliminates 5'-to-3' exonuclease activity).

Sequenase Ver 2.0™ is a modified T7 DNA polymerase sold by Amersham International plc, Little Chalfont, England.

Taq DNA polymerase was purchase from LTI, Gaithersburg, Md.

Thermo Sequenase™ is a Taq F→Y mutant containing a 5'-exonuclease deletion sold by Amersham International plc, Little Chalfont, England.

AmpliTaq FS™ is a Taq F→Y mutant believed to contain a Gly$^{37}$ mutation sold by Perkin Elmer ABI, Foster City, Calif.

Sequitherm™ is a thermophilic DNA polymerase sold by Epicenter, Madison, Wis.

Methods $^{35}$cycle Sequencing with Tne DNA Polymerase

Four separate base-specific reactions of the following composition are set up for each template: 6.5 nM dsDNA, 111 nM primer, 30 mM Tris-HCl (pH 9.0), 5 mM MgCl$_2$, 10 mM NaCl mM DTT, 0.05% (w/v) W-1, 0.185 U/μL Tne DNA polymerase mutant, 0.00185 U/μl thermophilic inorganic pyrophosphatase, 0.37 μCi/μl (0.37 μM) [α-$^{35}$S]dATP, 16.7 μM α-thio-dATP, 16.7 μM dCTP, 16.7 μM 7-deaza-dGTP, 16.7 μM dTTP, and either 0.042 μM ddATP, 0.3 μM ddCTP, 0.255 μM ddGTP or 0.375 μM ddTTP. Reaction volumes are 6 μl each. Sample tubes are incubated in an MJ Research DNA Engine thermal cycler at 95° C. for 3 minutes, followed by 20 cycles of (30 seconds at 95° C., 30 seconds at 55° C. and 60 seconds at 70° C.), and 10 cycles of (30 seconds at 95° C. and 60 seconds at 70° C). Reactions are terminated with 3 μl of stop solution (95% (v/v) formamide, 10 mM EDTA (pH 8.0), 0.1% (w/v) bromophenol blue, 0.1% (w/v) xylene cyanol) and denatured for 2 minutes at 70° C. Three microliter aliquots are separated on a 6% TBE/urea sequencing gel. The dried gel is exposed to Kodak BioMAX x-ray film at room temperature for approximately 18 hours, unless otherwise specified.

$^{32}$P-end Labeled Primer Cycle Sequencing with Tne DNA Polymerase

The sequencing primer is labeled by incubating the following 5 μl reaction for 10 minutes at 37° C.: 60 mM Tris-HCl, 10 mM MgCl$_2$, 200 mM KCl, 0.6 μM primer, 0.4 μM (2 μCi/μl) [γ-$^{32}$P]ATP, 0.2 U/μl T4 polynucleotide kinase. The reaction is stopped by incubating 5 minutes at 55° C. Four separate base-specific reactions of the following composition are then set up for each template: 1.1 nM dsDNA, 67 nM $^{32}$P-end-labeled primer, 30 mM Tris-HCl (pH 9.0), 5 mM MgCl$_2$, 50 mM KCl, 0.05% (w/v) W-1, 0.185 U/μl Tne DNA polymerase, 0.00185 U/μl thermophilic inorganic pyrophosphatase, 20 μM dATP, 20 μM dCTP, 20 μM 7-deaza-dGTP, 20 μM dTTP, and either 0.4 μM ddATP, 0.4 μM ddCTP, 0.4 μM ddGTP or 0.4 μM ddTTP. Reaction volumes are 10 μl each. Sample tubes are incubated in an MJ Research DNA Engine thermal cycler at 95° C. for 3 minutes, followed by 20 cycles of (30 seconds at 95° C., 30 seconds at 55° C. and 60 seconds at 70° C.), and 10 cycles of (30 seconds at 95° C. and 60 seconds at 70° C.). Reactions are terminated with 5 μl of stop solution (95% (v/v) formamide, 10 mM EDTA (pH 8.0), 0.1% (w/v) bromophenol blue, 0.1% (w/v) xylene cyanol) and denatured for 2 minutes at 70° C. Three μl aliquots are separated on a 6% TBE/urea sequencing gel. The dried gel is exposed to Kodak BioMAX x-ray film at room temperature for approximately 18 hours, unless otherwise specified.

Single-extension Sequencing with Tne DNA Polymerase

This reaction requires either ssDNA or denatured dsDNA. The DNA is annealed to primer in a 10 μl volume by heating for five minutes at 50° C. under the following reaction conditions: 150 nM dsDNA and 150 nM primer or 50 nM ssDNA and 50 nM primer with 60 mM Tris-HCl (pH 9.0), 60 mM KCl, 10 mM MgCl$_2$, 0.1% (w/v) W-1. The following labeling reaction is then incubated for five minutes at 50° C. in a 15.5 μl volume: 10 μl annealed DNA-primer 0.32 μCi/μl (0.32 μM) [α-$^{35}$S]dATP, 48.4 mM Tris HCl (pH 9.0), 48.4 mM KCl, 8.1 mM MgCl$_2$, 194 nM dCTP, 194 nM 7-deaza-dGTP, 194 nM dTTP, 6.5 nM DTT, 0.081% (w/v) W-1, 0.32 U/μl Tne DNA polymerase, 0.0032 U/μl thermophilic inorganic pyrophosphatase. The label mixture is then dispensed into four base-specific reaction tubes. Each tube contains a total reaction volume of 6 μl and is incubated for 5 minutes at 70° C. under the following conditions: DNA-labeled primer 0.19 μCi/μl (0.19 μM) [α-$^{35}$S]dATP, 28 mM Tris-HCl (pH 9.0), 28 mM KCl, 4.7 mM MgCl$_2$, 42 μM dATP, 42 μM dCTP, 42 μM 7-deaza-dGTP, 42 μM dTTP, 3.8 mM DTT, 0.047% (w/v) W-1, 0.19 U/μl Tne DNA polymerase, 0.0019 U/μl thermophilic inorganic pyrophosphatase and either 0.83 μM ddATP, 0.83 μM ddCTP, 0.83 μM ddGTP or 0.83 μM ddTTP. Reactions are terminated by adding 4 μl of stop solution (95% (v/v) formamide, 10 mM EDTA (pH 8.0), 0.1% (w/v) bromophenol blue, 0.1% (w/v) xylene cyanol) and denatured for 2 minutes at 70° C. Two μl aliquots are separated on a 6% TBE/urea sequencing gel. The dried gel is exposed to Kodak BioMAX x-ray film at room temperature for approximately 2 hours, unless otherwise specified.

Fluorescent Dye Primer Sequencing with Tne DNA Polymerase

Four base-specific reactions are set up for each template. The A and C reaction volumes are 5 μl and the G and T reaction volumes are 10 μl. The composition of the reactions are as follows: 20 nM dsDNA or 10 nM ssDNA, with 30 mM Tris-HCl (pH 9.0), 30 mM KCl, 5 mM MgCl$_2$, 0.05% (w/v) W-1, 20 μM dATP, 20 μM dCTP, 20 μM 7-deaza-dGTP, 20 μM dTTP, 0.29 U/μl Tne DNA polymerase, 0.0029 U/μl thermophilic inorganic pyrophosphatase. Each of the four tubes also contains a base-specific dye primer and ddNTP as follows:

A: 0.4 μM JOE dye primer, 0.4 μM ddATP
C: 0.4 μM FAM dye primer, 0.4 μM ddCTP
G: 0.4 μM TAMRA dye primer, 0.4 μM ddGTP
T: 0.4 μM ROX dye primer, 0.4 μM ddTTP Sample tubes are incubated in a thermal cycler at 95° C. for 3 minutes, followed by 20 cycles of (30 seconds at 95° C., 30 seconds at 55° C. and 60 seconds at 70° C.), and 10 cycles of (30 seconds at 95° C. and 60 seconds at 70° C.). Reactions are pooled, purified over a CentriSep spin column, and dried. The dried pellet is dissolved in 3 μl of 83% formamide, 4.2 mM EDTA (pH 8.0) and heated for 2 minutes at 90° C. just before loading the entire sample on a 4.75% polyacrylamide/TBE/urea gel in an ABI 373 Stretch machine. The gel is run at 32 watts for 14 hours.

Fluorescent Dye Terminator Sequencing with Tne DNA Polymerase

One 20 μl reaction is set up for each template. The composition of the reaction is an follows: 12.5 nM dsDNA or 6.25 nM ssDNA, with 0.16 μM primer, 30 mM Tris-HCl (pH 9.0), 30 mM KCl, 5 mM MgCl$_2$, 0.05% (w/v) W-1, 0.6 mM dATP, 0.6 mM dCTP, 1.8 mM dITP, 0.6 mM dTTP, 0.5 U/ml Tne DNA polymerase, 0.005 U/μl thermophilic inorganic pyrophosphatase. The reaction also includes four base-specific dye terminators at a final concentration 16-fold lower than the original concentration supplied by ABI. The sample tube is incubated in a thermal cycler for 25 cycles of (30 seconds at 96° C., 15 seconds at 50° C. and 4 minutes at 60° C. The reaction is purified over a CentriSep spin column, and dried. The dried pellet is dissolved in 3 μl of 83% formamide, 4.2 mM EDTA (pH 8.0) and heated for 2 minutes at 90° C. just before loading the entire sample on a 4.75% polyacrylamide/TBE/urea gel in an ABI 373 Stretch machine. The gel is run at 32 watts for 14 hours.

Results

Single-extension Sequencing

Figure 9:
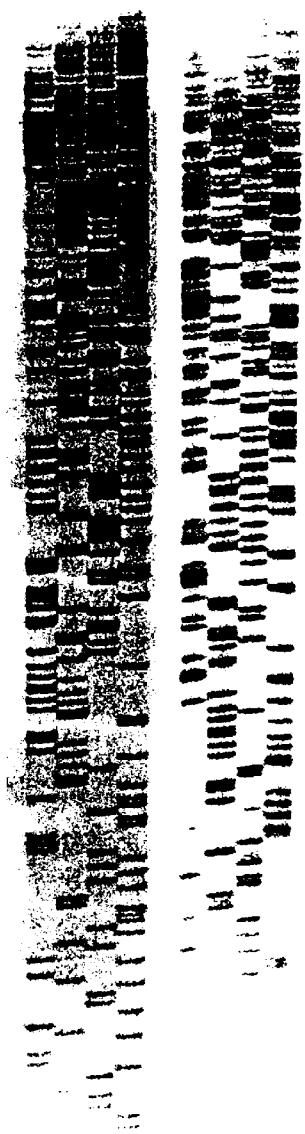
FIG. 9 depicts a gel containing two sequencing reaction sets showing the efficient $^{35}S$ incorporation by Tne DNA polymerase of Example 12. Alkali-denatured pUC19 DNA was sequenced with Tne DNA polymerase in set A. M13 mp19(+) DNA was sequenced in set B.

FIG. 9 shows that the efficient $^{35}$S incorporation by Tne DNA polymerase mutant provides strong signals in single- and double-strand DNA sequencing. Alkali-denatured pUC19 DNA (1.5 pmol) was sequenced using single-extension sequencing with Tne DNA polymerase of Example 12 as described above (set A); film was exposed for only2 hours. M13 mp19(+) DNA was used at one-tenth the normal amount of template (40 pmol) in the Tne DNA polymerase single-extension sequencing reactions as described (set B); film exposed for 20 hours. Since the Tne mutant produces such a strong signal, templates can be used more economically without sacrificing sequence quality.

Figure 10:
FIG. 10 depicts a gel containing three sequencing reaction sets showing that the mutant Tne DNA polymerase of Example 12 generates clear sequence from plasmids containing cDNAs with poly(da) tails. Alkali-denatured plasmid DNAs containing cDNA inserts were sequenced using either Tne DNA polymerase (sets A and B), or Sequenase Ver 2.0 (set C).

FIG. 10 shows that the Tne DNA polymerase mutant generates clear sequence from plasmids containing cDNAs with poly(dA) tails. Alkali-denatured plasmid DNAs containing cDNA inserts (1.5 pmol) were sequenced using either the Tne DNA polymerase mutant in single-extension sequencing (sets A and B) as described, or Sequenase Ver 2.0™ (set C) following the standard kit protocol. Set A, β-actin cDNA; set B, RPA1 cDNA (a replication protein); and set C, RPA2 cDNA (a replication protein).

Figure 11:
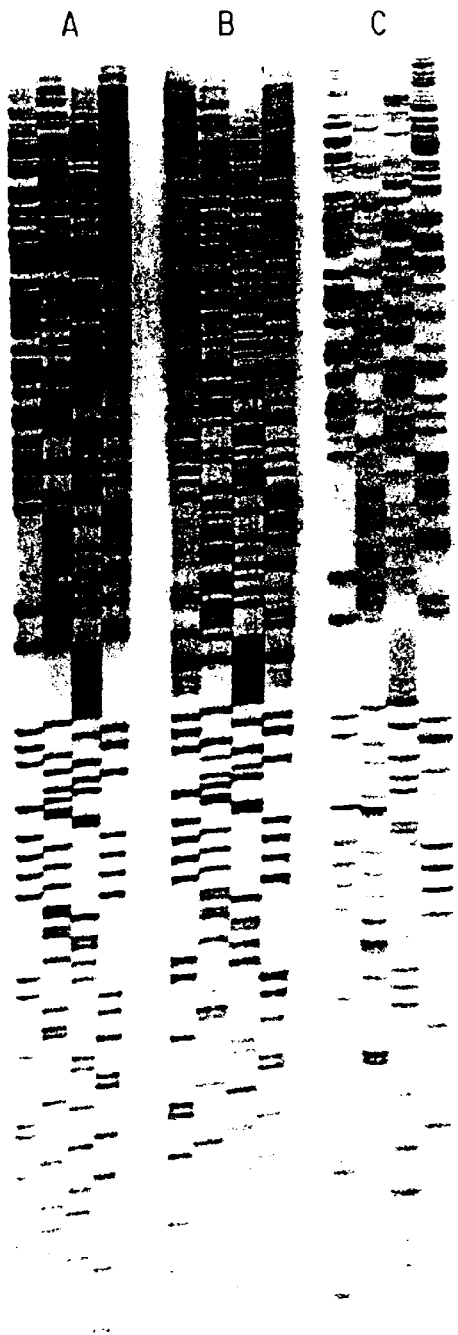
FIG. 11 depicts a gel containing three sequencing reaction sets that compare the mutant Tne DNA polymerase of Example 12 (set A), Sequenase™ (set B) and Taq DNA polymerase (set C) generated sequences from a plasmid containing poly(dC).

FIG. 11 compares the Tne DNA polymerase mutant, Sequenase™ and Taq DNA polymerase generated sequences from a plasmid containing poly(dC). Plasmid DNA (1.5 pmol) containing a poly(dC)-tailed 5' RACE-derived insert was alkali denatured. The DNA was sequenced using Tne DNA polymerase mutant in single-extension sequencing (set A) as described, Sequenase Ver 2.0™ (set B) as described in the kit manual, and by Taq DNA polymerase (set C) following the recommended protocol in the TaqTrack kit (Promega, Madison, Wis.).

Cycle Sequencing

Figure 12:
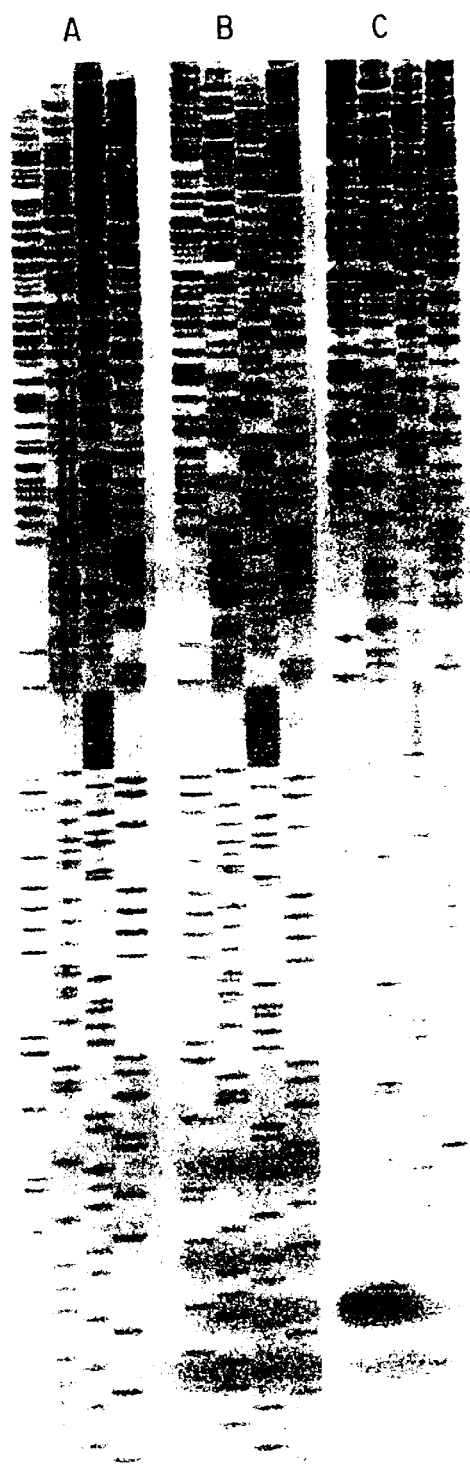
FIG. 12 depicts a gel containing three sequencing reaction sets showing that the mutant Tne DNA polymerase of Example 12 (set A) produces $^{35}S$-labeled sequence 3-fold stronger than Thermo Sequenase™ (set B) and without the uneven band intensities obtained with Taq DNA polymerase (set C).

FIG. 12 shows that the Tne DNA polymerase mutant in cycle sequencing produces $^{35}$S-labeled sequence 3-fold stronger than Thermo Sequenase™ and without the 60-cycle labeling step. Plasmid DNA (0.5 μg) containing a poly(dC)-tailed 5' RACE-derived insert was cycled sequenced using Tne DNA polymerase mutant (set A) as described; film exposure was 6 hours. Using Thermo Sequenase™ as described in the kit manual, the plasmid DNA (0.5 μg) was labeled with $^{35}$S by partial primer extension using an incubation of 60 cycles. This was followed by the standard cycle sequencing protocol in the presence of chain terminators (set B); film exposure was 18 hours. The plasmid DNA (0.5 μg) was cycle sequenced using Taq DNA polymerase (set C) as described in the fmol kit manual; film exposure was 18 hours. Note, uneven band intensities in set C.

Figure 13:
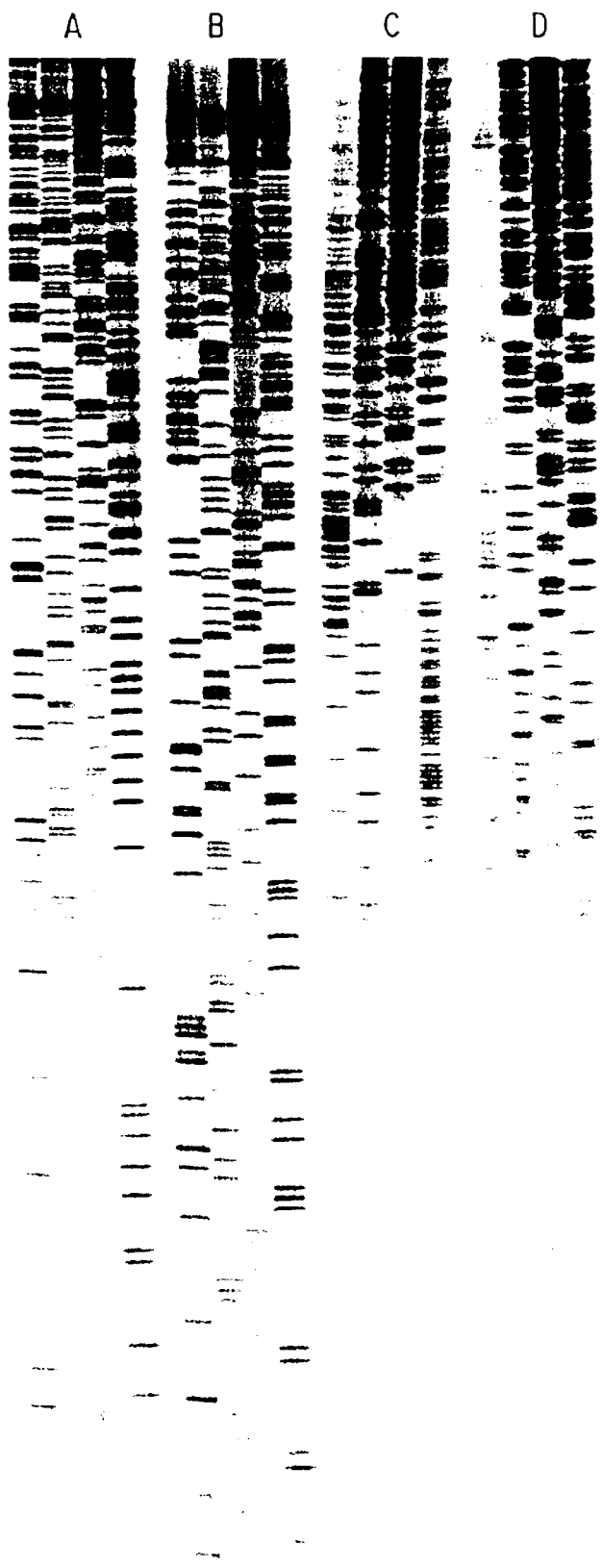
FIG. 13 depicts a gel containing four sequencing reaction sets demonstrating that the mutant Tne DNA polymerase of Example 12 produces high quality sequences of in vitro amplified DNA (set A, *E. coli* β polI (~450 bp); set B, *E. coli* rrsE (~350 bp); set C, ori from pSC101 (~1.5 kb); and set D, an exon from human HSINF gene (~750 bp).

FIG. 13 shows that the Tne DNA polymerase mutant produces high quality sequences of in vitro amplified DNA. Templates were in vitro amplified directly from E. coli chromosomal DNA, from plasmid pSC101 and from human genomic DNA, purified by simple isopropanol precipitation and quantitated. DNAs (100 fmol) were cycle sequenced as described using the Tne DNA polymerase mutant and one of the amplification primers. Set A, E. coli βpolI (~450 bp); set B, E. coli rrsE (~350 bp); set C, ori from pSC101 (~1.5 kb); and set D, an exon from human HSINF gene (~750 bp); amplified product sizes in parentheses. Note, these DNAs could not be sequenced using Thermo Sequenase™ because the primers did not meet the extra requirements for the labeling reaction.

Figure 14A:
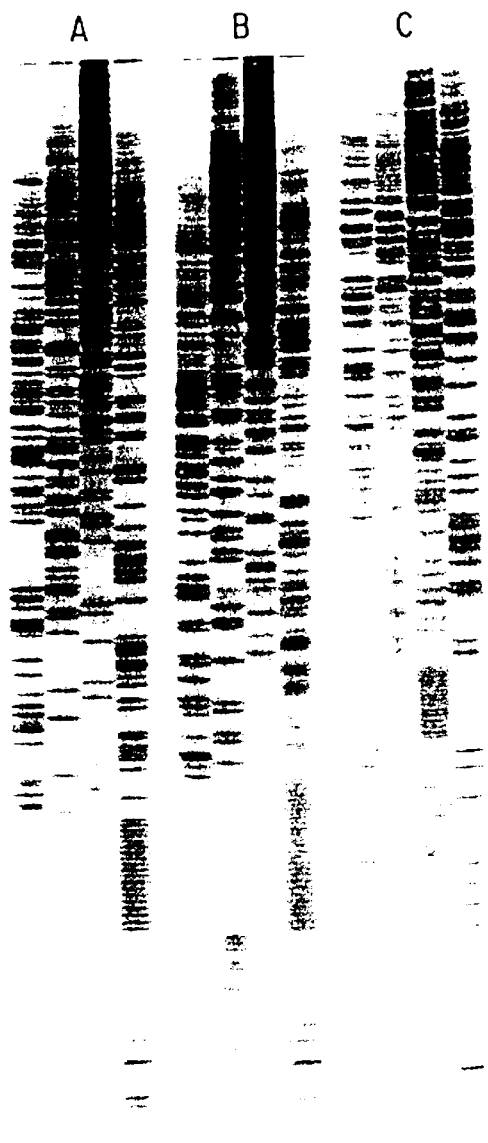
FIGS. 14A and 14B depict gels containing three and four sequencing reaction sets, respectively, showing that the mutant Tne DNA polymerase of Example 12 provides superior sequence from double-stranded DNA clones containing poly(dA) or poly(dC) stretches.
Figure 14B:
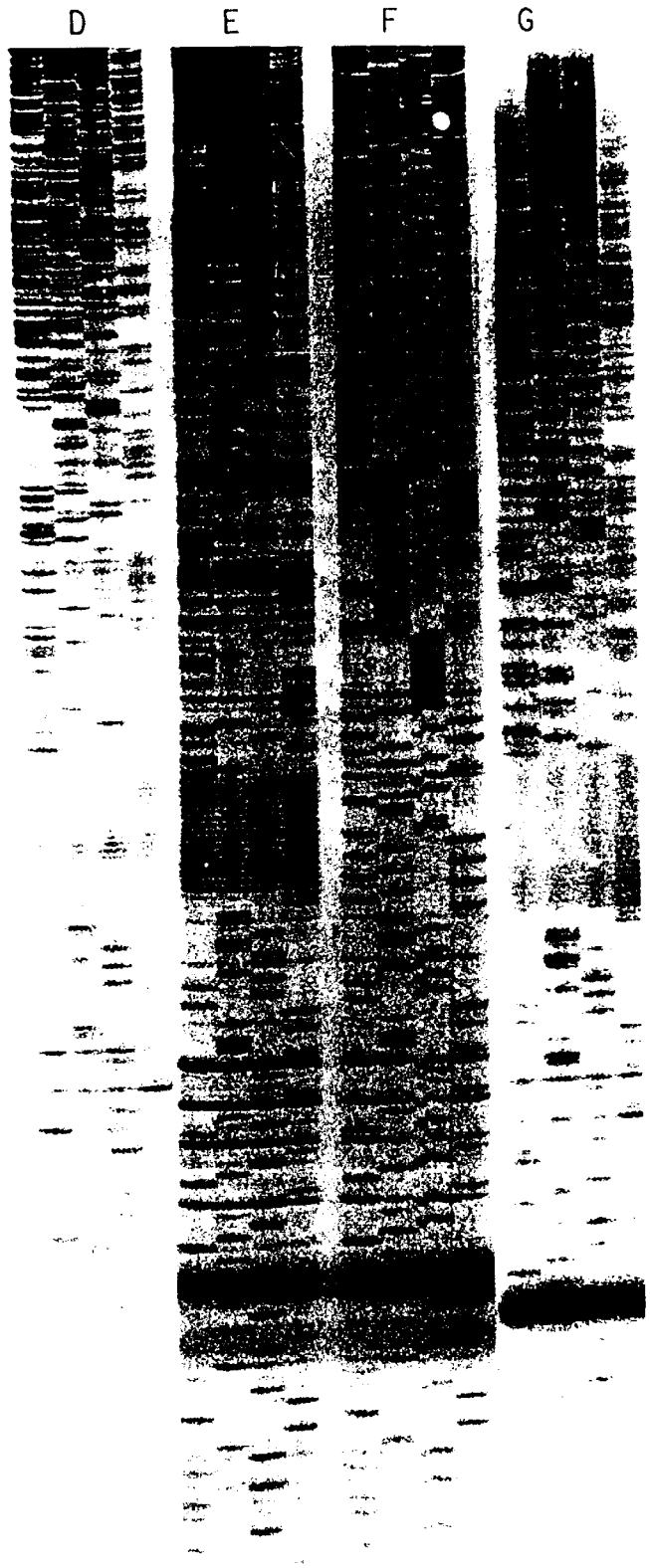

FIGS. 14A and 14B show that the Tne DNA polymerase mutant provides superior sequence from double-stranded DNA clones containing poly(dA) or poly(dC) stretches. FIG. 14A, supercoiled plasmid DNAs containing inserts with homopolymers were cycle sequenced using the Tne DNA polymerase mutant as described; film exposure was 6 hours. Set A, RPA1; set B, elf (cap binding protein); and set C, a poly(dC)-tailed 5' RACE-derived insert.

FIG. 14B, supercoiled plasmid DNAs containing inserts with homopolymers were cycled sequenced using Taq DNA polymerase (set D) in the fmol kit manual, or SequiTherm™ (sets E–G) following the kit manual; film exposure was 18 hours. Set D, RPA; set E, RPA; set F, a poly(dC)-tailed 5' RACE-derived insert; and set G, elf. Note, the many false stops, especially in the homopolymer region.

Figure 15:
FIG. 15 depicts a gel containing two sequencing reaction sets showing cycle sequencing using the mutant Tne DNA polymerase of Example 12 and $^{32}P$ end-labeled primer.
Figure 16A:
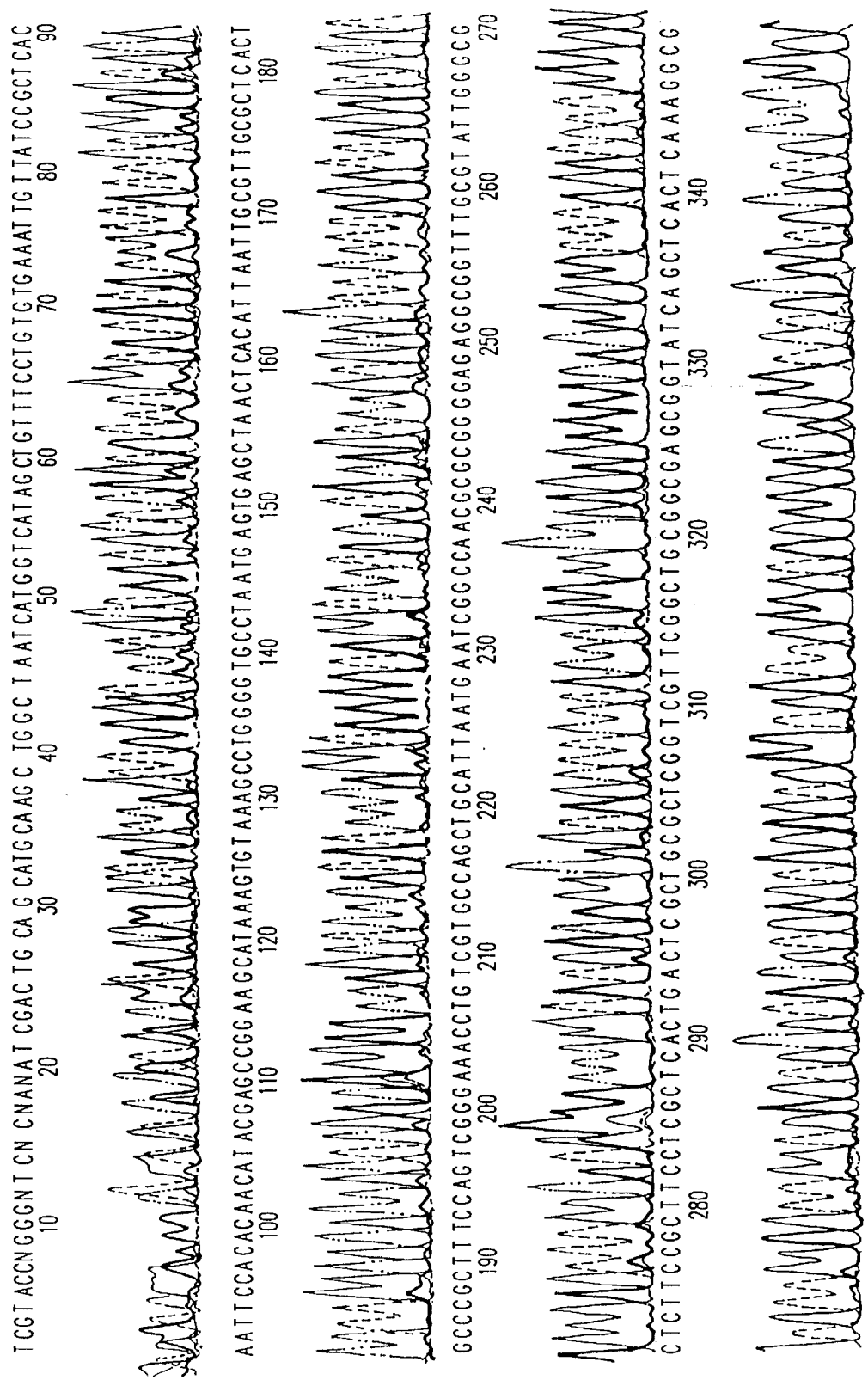
FIGS. 16A–16C and 16D–16F depict two sets of chromatograms showing comparison of the mutant Tne DNA polymerase of Example 12 (16A–16C) to AmpliTaq FS™ (16–16F) in Fluorescent Dye Primer Sequencing.
Figure 16B:
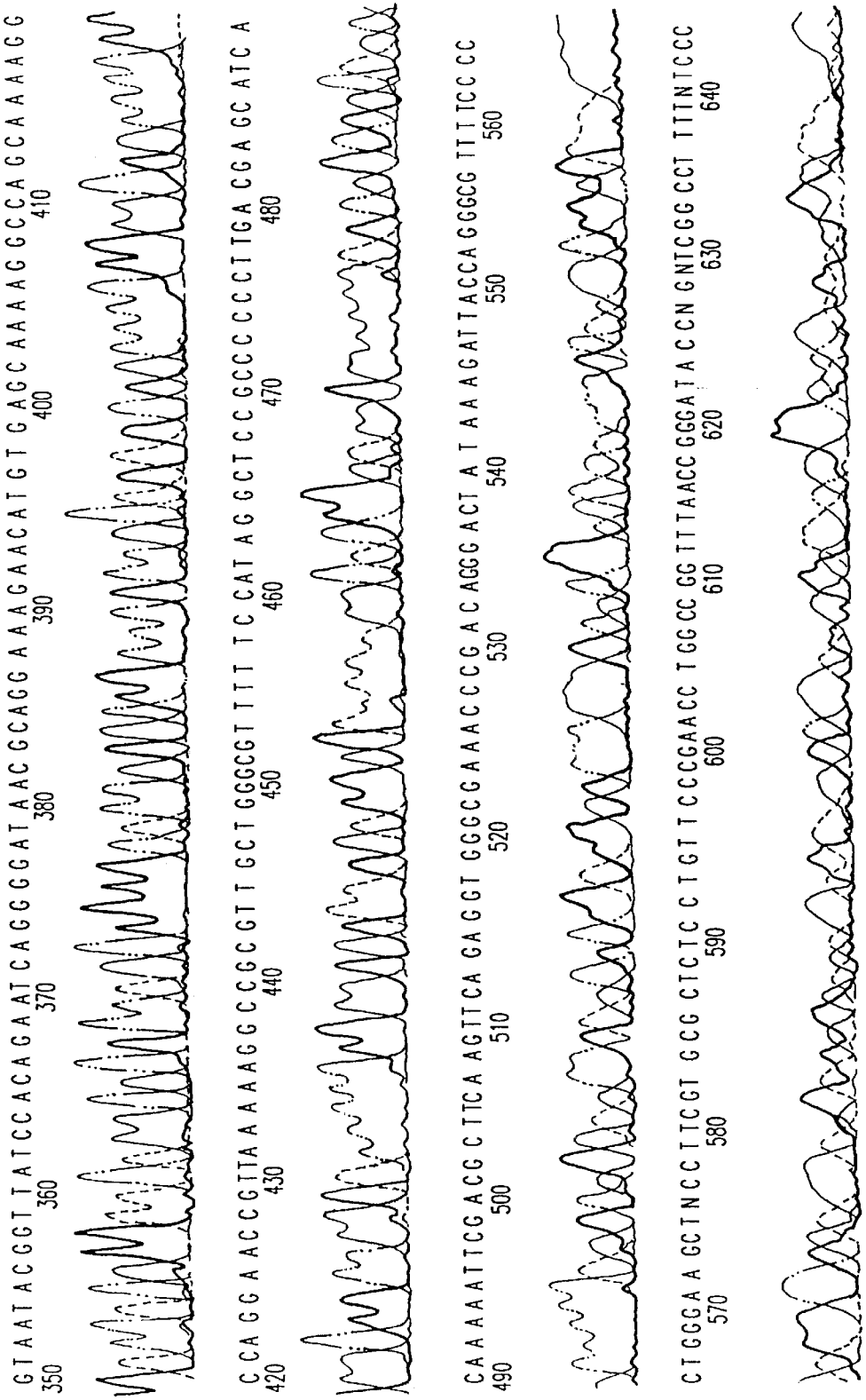
Figure 16C:
Figure 16D:
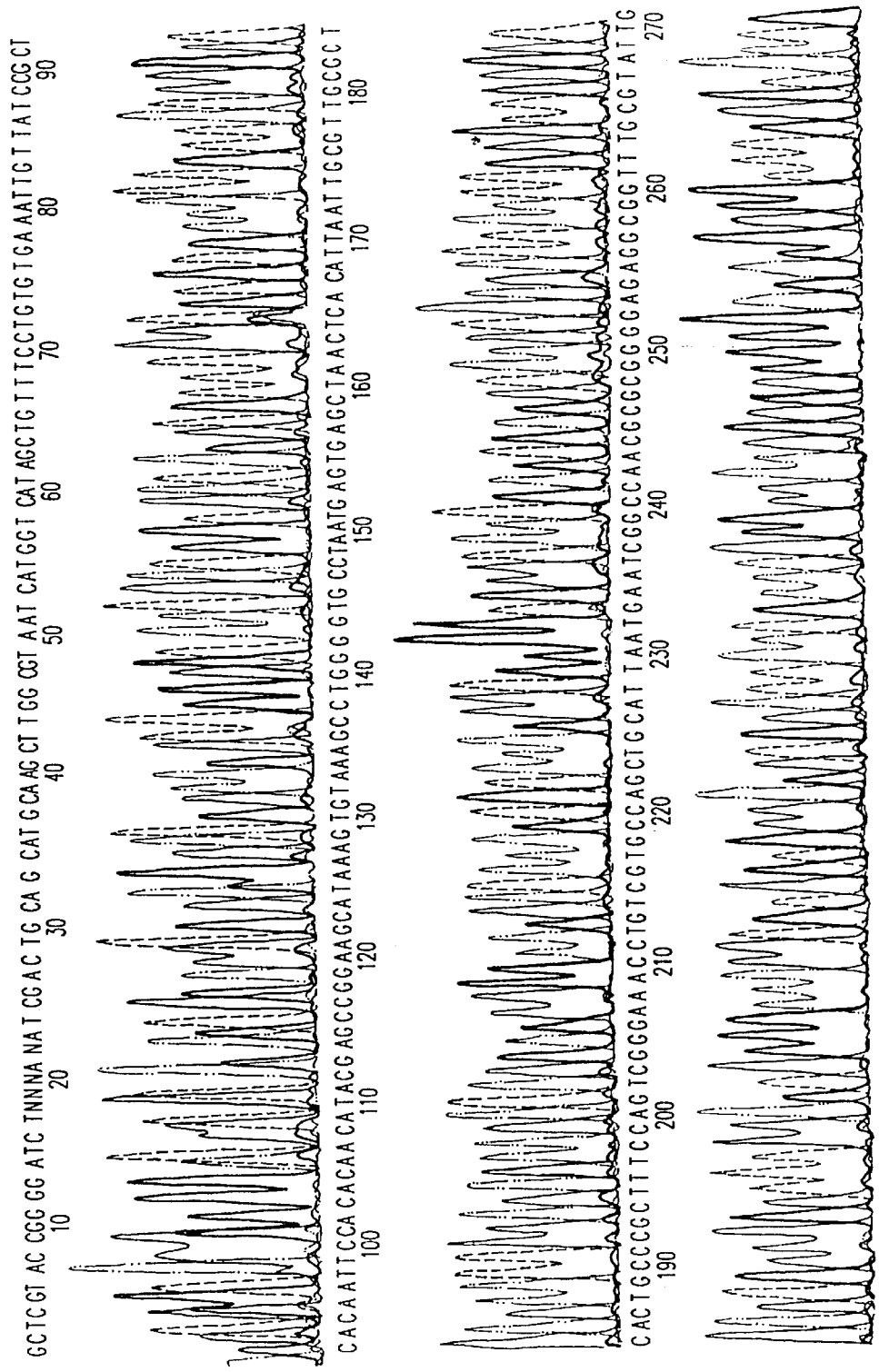
Figure 16E:
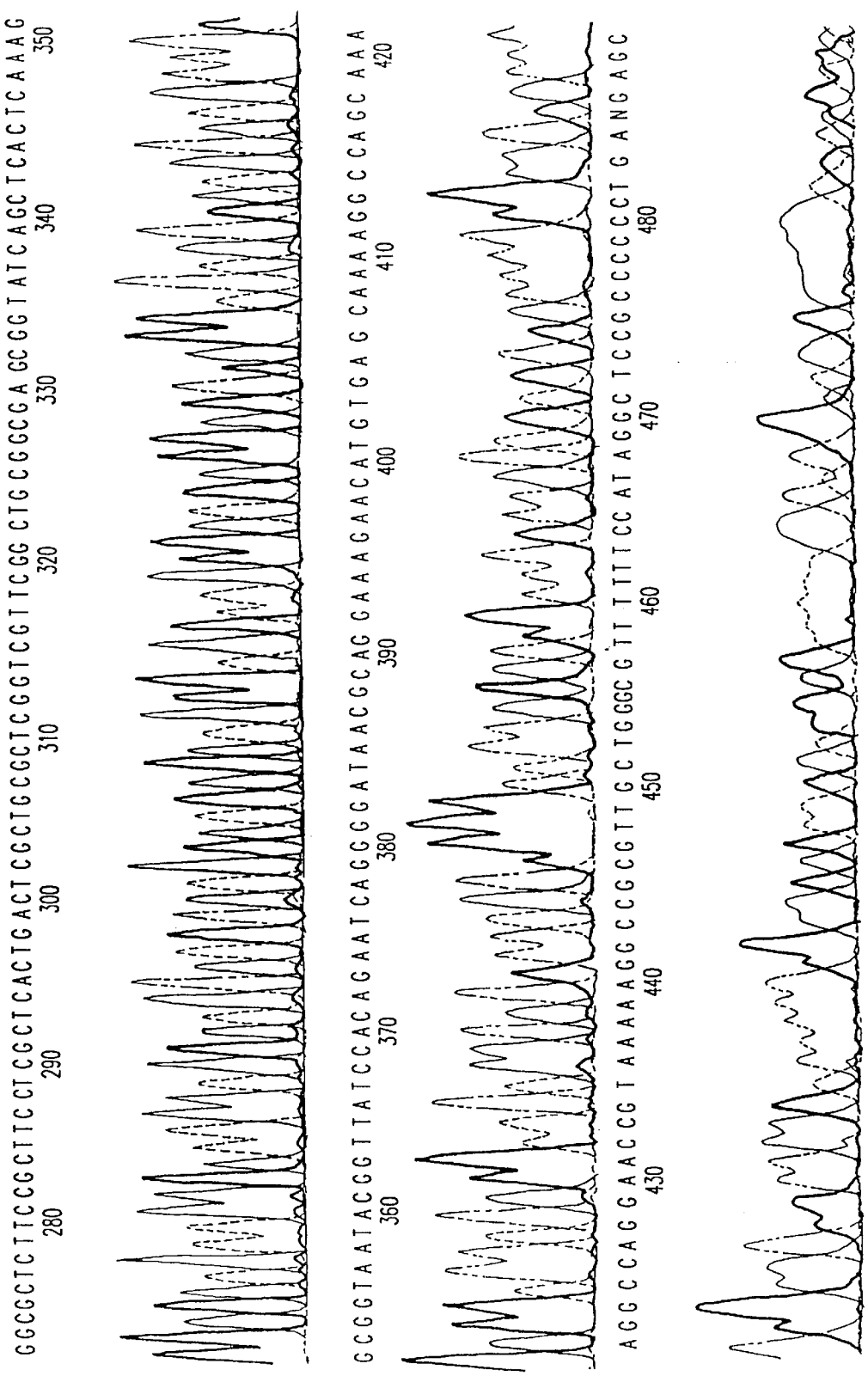
Figure 16F:
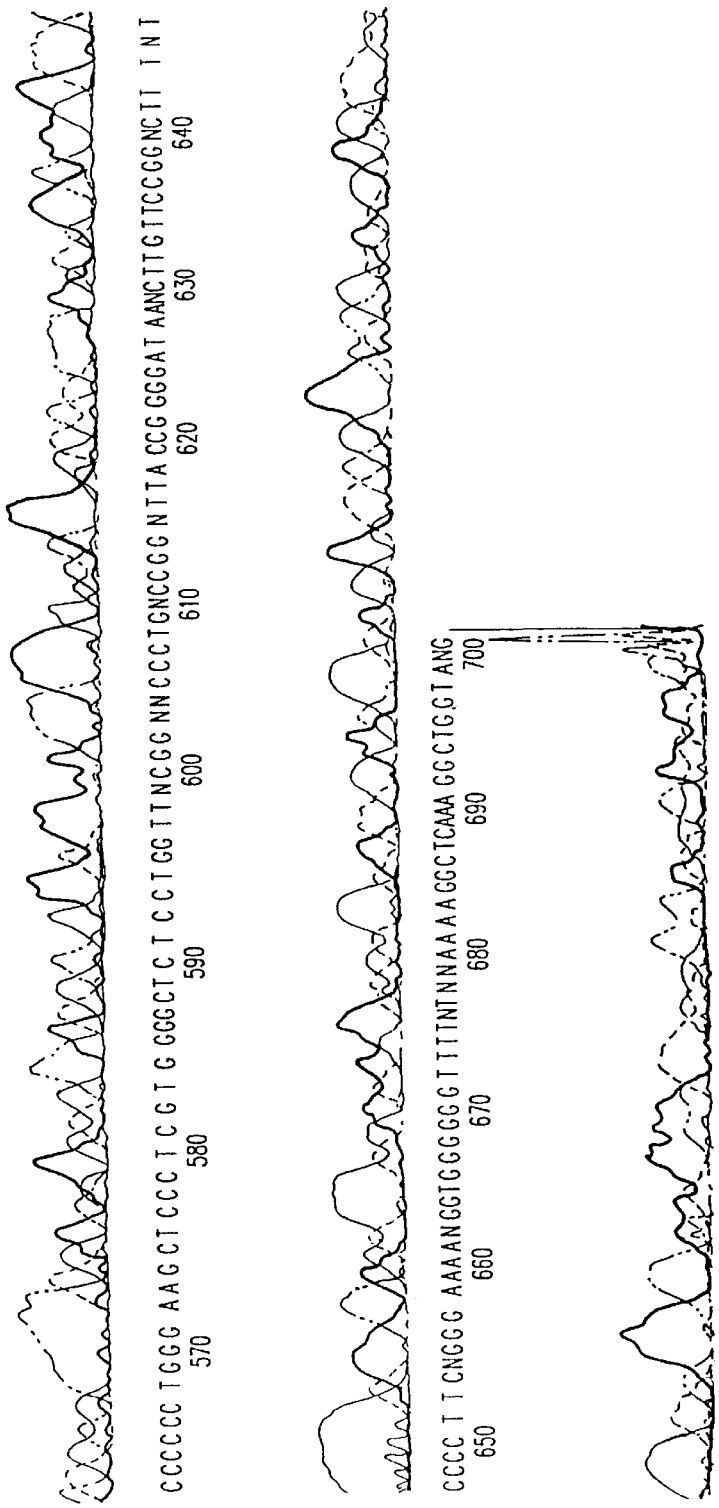
Figure 17A:
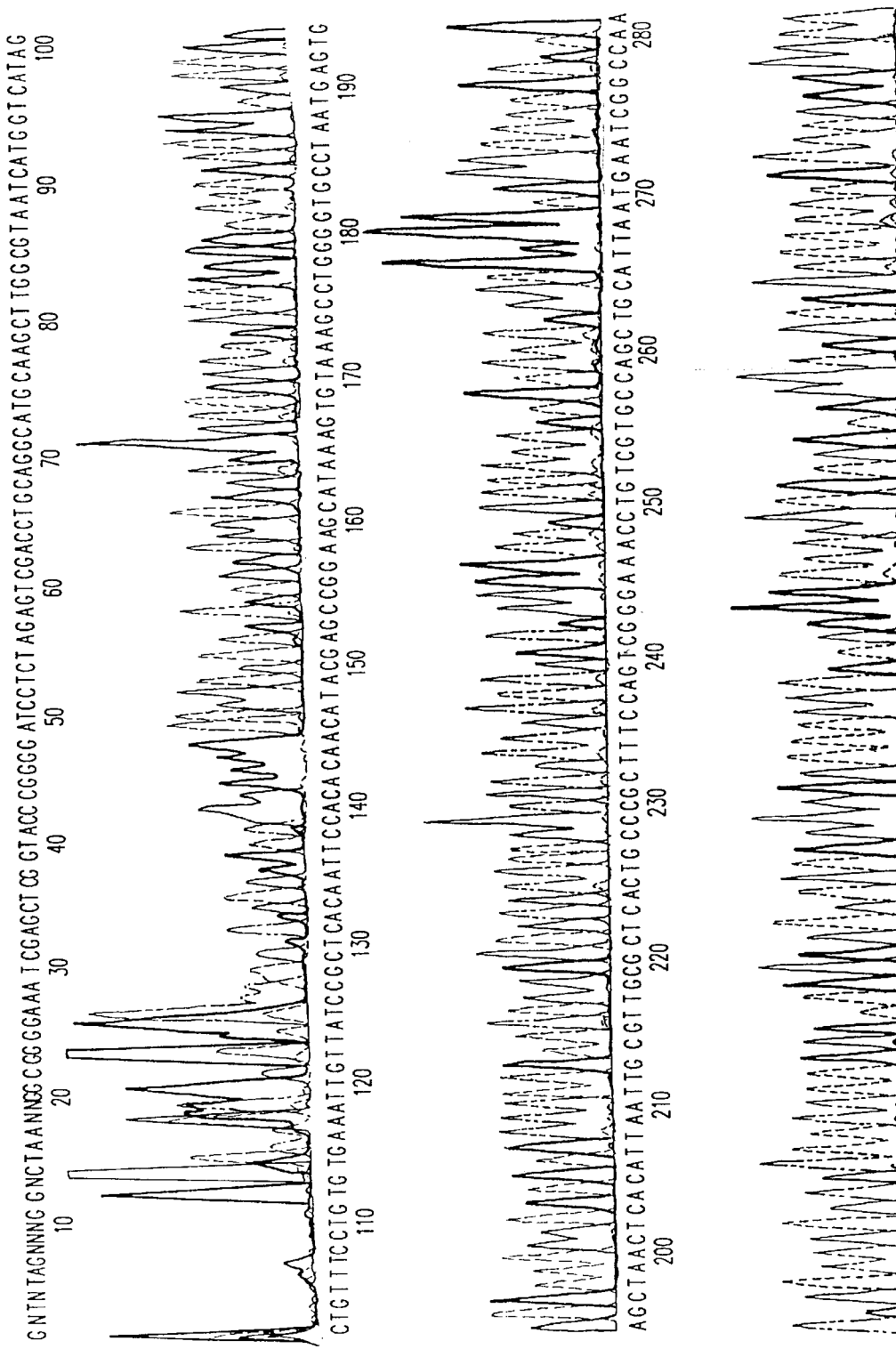
Figure 17B:
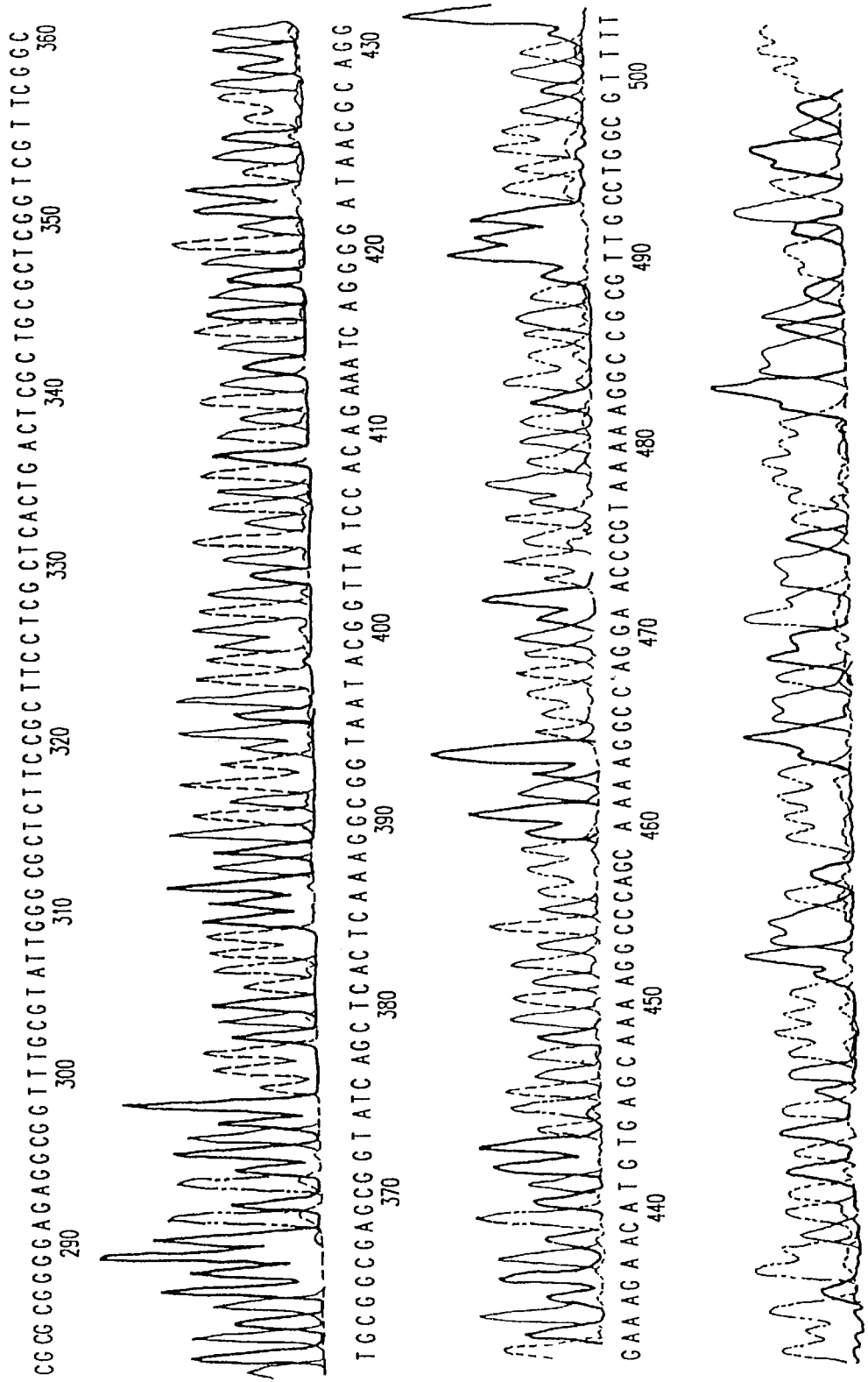
Figure 17C:
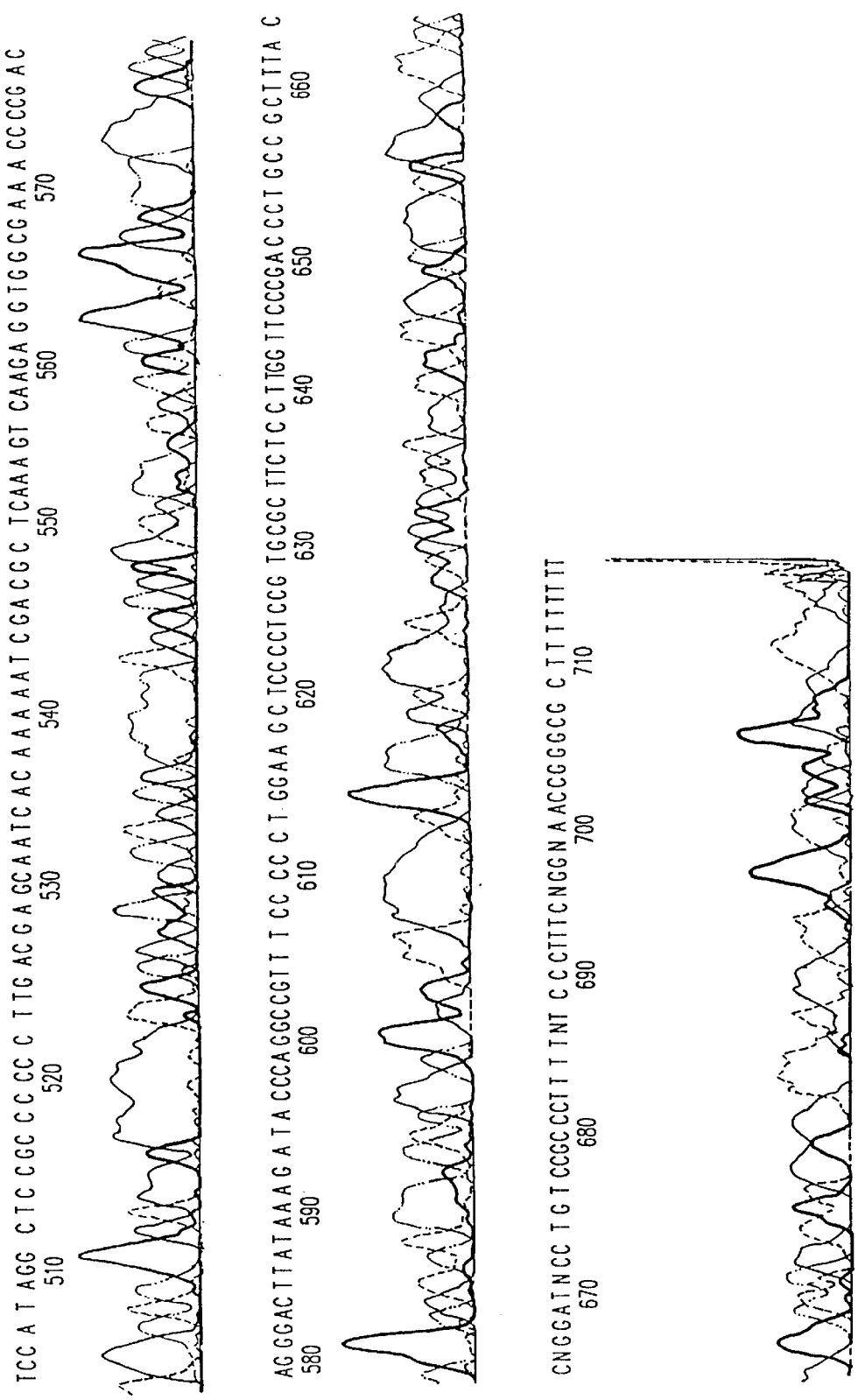
Figure 17D:
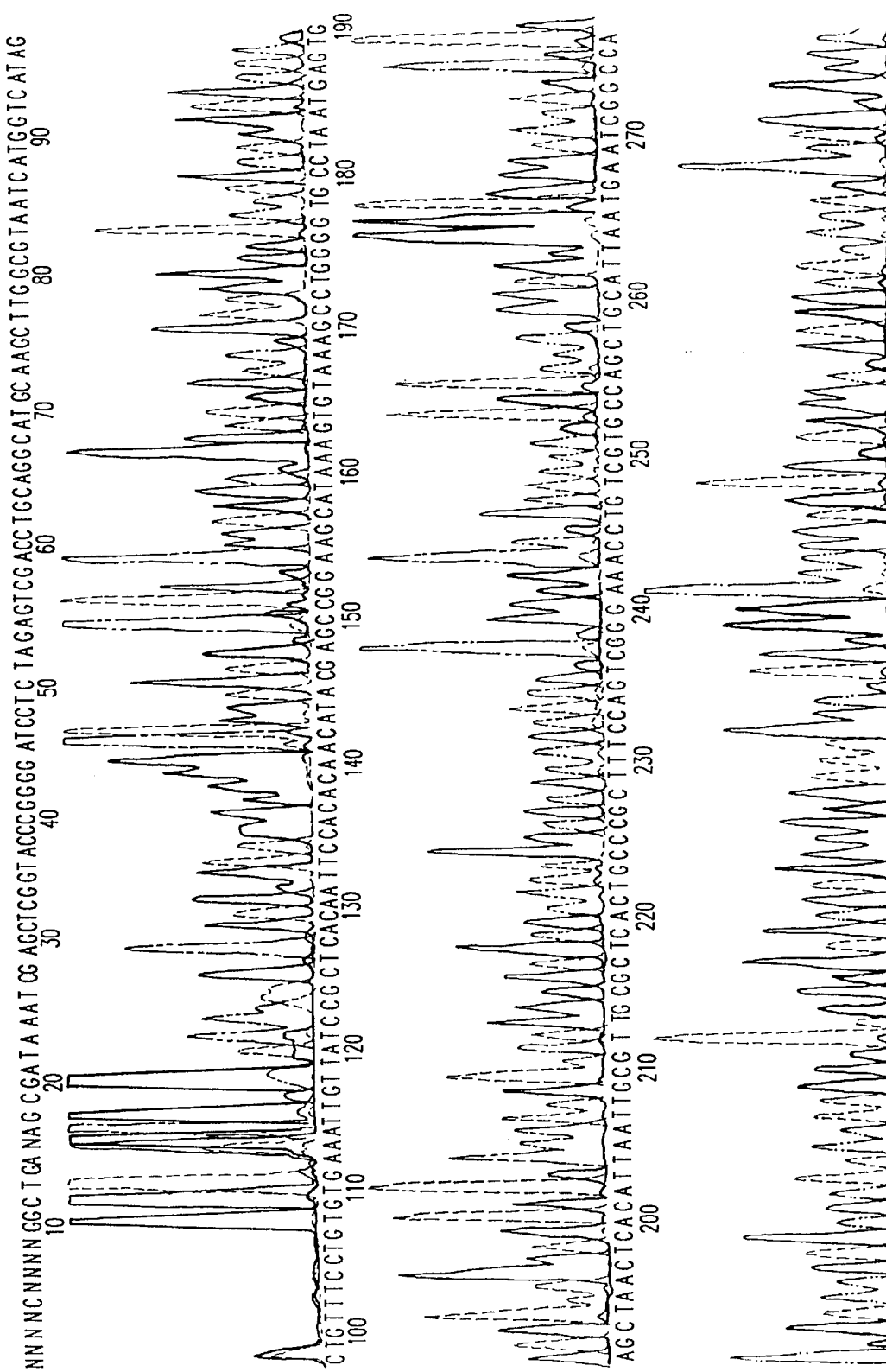
Figure 17E:
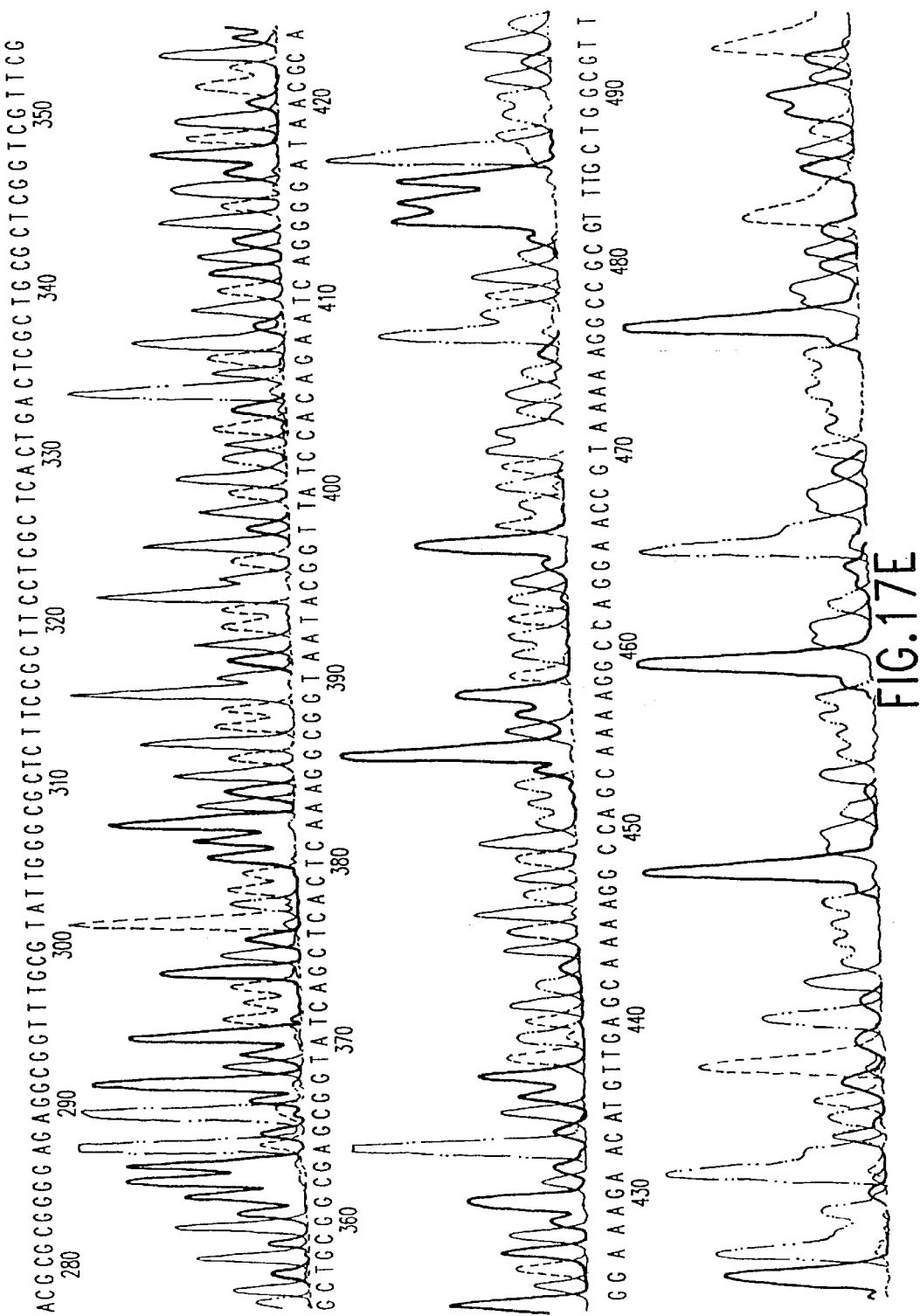

FIG. 15 shows cycle sequencing using the Tne DNA polymerase mutant and $^{32}$P end-labeled primer. A sequencing primer was first 5'-end labeled with $^{32}$P using T4 kinase. A supercoiled plasmid DNA (50 fmol) was cycle sequenced using the Tne DNA polymerase mutant as described; film exposure was 18 hours. The left and right sets are aliquots of the same reaction, the right set loaded on the gel 45 minutes after the left.

Fluorescent Automated Sequencing

FIGS. 16A–16C and 16D–16F show a comparison of the Tne DNA polymerase mutant (16A–16C) to AmpliTaq FS™ (16D–16F) in fluorescent dye primer sequencing. pUC19 DNA was sequenced with dye primers (ABI, Foster City, Calif.) using either the Tne DNA polymerase mutant or AmpliTaq FS™ as described.

FIGS. 17A–17C and 17D–17F show a comparison of the Tne DNA polymerase mutant (17A–17C) to AmpliTaq FS™ (17D–17F) in fluorescent dye terminator sequencing. pUC19 DNA was sequenced with dye terminators (ABI, Foster City, Calif.) using either the Tne DNA polymerase mutant or AmpliTaq FS™ as described. Note, greater evenness of peak heights with Tne.

These results demonstrate that the Tne DNA polymerase mutant gives unexpectedly better results in DNA sequencing compared to other DNA polymerases, whether they are similar mutants or not.

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

What is claimed is:

1. An isolated *Thermotoga neopolitana* (Tne) DNA polymerase, wherein said Tne DNA polymerase is a Pol I-type DNA polymerase.

2. The DNA polymerase of claim 1, which is isolated from *Thermotoga neapolitana*.

3. The DNA polymerase of claim 2, which is isolated from *Thermotoga neapolitana* DSM 5068 and said DNA polymerase has a molecular weight of about 100 kilodaltons.

4. An isolated *Thermotoga neopolitana* (Tne) DNA polymerase having the amino acid sequence of SEQ ID NO:3.

5. A vector comprising a gene encoding the DNA polymerase of claim 1.

6. The vector of claim 5, wherein said gene is operably linked to a promoter.

7. The vector of claim 6, wherein said promoter is selected from the group consisting of a λ-$P_L$ promoter, a tac promoter, a trp promoter, and a trc promoter.

8. A host cell comprising the vector of claim 5.

9. A method of producing a DNA polymerase, said method comprising:

(a) culturing the host cell of claim 8;

(b) expressing said gene; and (c) isolating said DNA polymerase from said host cell.

10. The method of claim 9, wherein said host cell is *E. coli*.

11. A method of synthesizing a double-stranded DNA molecule comprising:

(a) hybridizing a primer to a first DNA molecule; and (b) incubating said DNA molecule of step (a) in the presence of one or more deoxy- or dedioxy ribonucleoside triphosphates and the DNA polymerase of claim 4, under conditions sufficient to synthesize a second DNA molecule complementary to all or a portion of said first DNA molecule.

12. The method of claim 11, wherein said deoxy- or dideoxyribonucleoside triphosphates are selected from the group consisting of dATP, dCTP, dGTP, dTTP, dITP, 7-deaza-dGTP, dUTP, ddATP, ddCTP, ddGTP, ddITP, ddTTP, [α-S]dATP, [α-S]dTTP, [α-S]dGTP, and [α-S]dCTP.

13. A method for amplifying a double stranded DNA molecule, comprising:

(a) providing a first and second primer, wherein said first primer is complementary to a sequence at or near the 3'-termini of the first strand of said DNA molecule and said second primer is complementary to a sequence at or near the 3'-termini of the second strand of said DNA molecule;

(b) hybridizing said first primer to said first strand and said second primer to said second strand in the presence of the DNA polymerase of claim 4, under conditions such that a third strand complementary to said first strand and a fourth strand complementary to said second strand are synthesized;

(c) denaturing said first and third strand and said second and fourth strands; and (d) repeating steps (a) to (c) one or more times.

14. A kit for sequencing a DNA molecule, comprising:

(a) a first container means comprising the DNA polymerase of claim 4;

(b) a second container means comprising one or more dideoxyribonucleoside triphosphates; and (c) a third container means comprising one or more deoxyribonucleoside triphosphates.

15. A kit for amplifying a DNA molecule, comprising:

(a) a first container means comprising the DNA polymerase of claim 4; and (b) a second container means comprising one or more deoxyribonucleoside triphosphates.

16. A method of preparing cDNA from mRNA, comprising
(a) contacting mRNA with an oligo(dT) primer or other complementary primer to form a hybrid, and
contacting said hybrid formed in step (a) with the Tne DNA polymerase of claim 1 and dATP, dCTP, dGTP and dTTP, whereby a cDNA-RNA hybrid is obtained.

17. A method of preparing dsDNA from mRNA, comprising:
(a) contacting mRNA with an oligo (dT) primer or other complementary primer to form a hybrid; and
(b) contacting said hybrid formed in step (a) with the Tne DNA polymerase of claim 1, dATP, dCTP, dGTP and dTTP, and an oligo nucleotide or primer which is complementary to the first strand cDNA;
whereby dsDNA is obtained.

* * * * *

UNITED STATES PATENT AND TRADEMARK OFFICE
CERTIFICATE OF CORRECTION

PATENT NO. : 6,506,560 B1
DATED : January 14, 2003
INVENTOR(S) : Hughes et al.

It is certified that error appears in the above-identified patent and that said Letters Patent is hereby corrected as shown below:

Column 59,
Lines 35 and 43, please delete "*neopolitana*" and insert therein -- *neapolitana* --;
Line 35, please delete "(Tne)" and insert therein -- (*Tne*) --;
Lines 36 and 43, please delete "Tne" and insert therein -- *Tne* --;
Line 50, please delete "tac" and insert therein -- *tac* --;
Line 51, please delete "trp" and insert therein -- *trp* --;
Line 51, please delete "trc" and insert therein -- *trc* --;
Lines 65-66, please delete "dedioxy ribonucleoside" and insert therein
-- dideoxyribonucleoside --;

Column 60,
Line 38, please delete "ddlTP" and insert therein -- ddITP --;

Column 61,
Line 5, please delete "contacting" and insert therein -- (b) contacting --;
Line 5, please delete "Tne" and insert therein -- *Tne* --;

Column 62,
Line 3, please delete "Tne" and insert therein -- *Tne* --.

Signed and Sealed this

Sixteenth Day of December, 2003

JAMES E. ROGAN
*Director of the United States Patent and Trademark Office*